United States Patent
Stone et al.

(10) Patent No.: US 8,992,558 B2
(45) Date of Patent: Mar. 31, 2015

(54) LATERAL ACCESS SYSTEM FOR THE LUMBAR SPINE

(75) Inventors: Corbett Stone, San Diego, CA (US); Ephraim Akyuz, Logan, UT (US); Stuart Goble, Logan, UT (US); Bryan Howard, Smith Field, UT (US); Daniel J. Triplett, Providence, UT (US); Douglas M. Lorang, North Logan, UT (US); Andrew Fauth, River Heights, UT (US)

(73) Assignee: OsteoMed, LLC, Addison, TX (US)

(*) Notice: Subject to any disclaimer, the term of this patent is extended or adjusted under 35 U.S.C. 154(b) by 732 days.

(21) Appl. No.: 13/087,114

(22) Filed: Apr. 14, 2011

(65) Prior Publication Data

US 2011/0237898 A1    Sep. 29, 2011

Related U.S. Application Data

(63) Continuation-in-part of application No. 12/640,413, filed on Dec. 17, 2009.

(60) Provisional application No. 61/324,185, filed on Apr. 14, 2010, provisional application No. 61/442,608, filed on Feb. 14, 2011, provisional application No. 61/138,629, filed on Dec. 18, 2008, provisional application No. 61/166,069, filed on Apr. 2, 2009.

(51) Int. Cl.
*A61M 29/00* (2006.01)
*A61B 1/32* (2006.01)
(Continued)

(52) U.S. Cl.
CPC .............. *A61B 17/0218* (2013.01); *A61B 17/02* (2013.01); *A61B 17/3417* (2013.01);
(Continued)

(58) Field of Classification Search
CPC ........... A61B 17/0218; A61B 17/0256; A61B 17/02; A61B 17/3439; A61B 17/3484; A61B 17/3417
See application file for complete search history.

(56) References Cited

U.S. PATENT DOCUMENTS

| 447,761 A | 3/1891 | Clough |
|---|---|---|
| 832,201 A | 10/1906 | Fistler |

(Continued)

FOREIGN PATENT DOCUMENTS

| WO | WO9609013 | 3/1996 |
|---|---|---|
| WO | WO9916499 | 4/1999 |

OTHER PUBLICATIONS

Biomet Spine; AccuVision Minimally Invasive Spinal Exposure System, Surgical Technique Dec. 2009.
(Continued)

*Primary Examiner* — Devin Henson
(74) *Attorney, Agent, or Firm* — Norton Rose Fulbright US LLP

(57) ABSTRACT

A minimally invasive dilation device includes a plurality of rigid arms radially arrayed about a center and a dilating member positioned between the arms. A stylus may occupy the center. An outer flexible sleeve may be circumferentially secured to the arms, lying within or without the plurality of arms. An inner mesh may surround the stylus and dilating member. The device may be introduced into tissue toward a targeted area, while in a closed configuration. The dilating member may be a balloon, wherein upon inflation of the balloon, the arms are pushed radially outward, expanding the device and dilating the surrounding tissue. The dilating member may be a tube, wherein upon insertion of the tube, the arms are pushed radially outward. A cannula may be inserted inside the plurality of arms to keep the arms in an open configuration, and the dilating member may be withdrawn, providing an open passageway through the device to the targeted area. The device may be used with a neural monitoring system.

19 Claims, 66 Drawing Sheets

(51) Int. Cl.
*A61B 17/02* (2006.01)
*A61M 29/02* (2006.01)
*A61B 17/34* (2006.01)
*A61B 19/00* (2006.01)
*A61M 25/10* (2013.01)

(52) U.S. Cl.
CPC ........ *A61B 17/3439* (2013.01); *A61B 17/0293* (2013.01); *A61B 2019/268* (2013.01); *A61M 25/10* (2013.01); *A61M 29/02* (2013.01)
USPC ............ 606/191; 600/204; 600/210; 600/245

(56) References Cited

U.S. PATENT DOCUMENTS

| | | | |
|---|---|---|---|
| 1,839,726 A | 1/1932 | Arnold | |
| 1,863,057 A | 6/1932 | Innes | |
| 1,944,009 A | 1/1934 | Homer | |
| 2,313,164 A | 3/1943 | Nelson | |
| 2,586,488 A | 2/1952 | Smith | |
| 2,812,758 A | 11/1957 | Blumenschein | |
| 2,854,983 A | 10/1958 | Baskin | |
| 3,070,088 A | 12/1962 | George Brahos | |
| 3,087,486 A | 4/1963 | Kilpatrick | |
| 3,397,699 A | 8/1968 | Kohl | |
| 3,417,746 A | 12/1968 | Moore | |
| 3,509,883 A | 5/1970 | Dibelius | |
| 3,770,342 A | 11/1973 | Dudragne | |
| 3,788,318 A | 1/1974 | Kim | |
| 3,789,852 A | 2/1974 | Kim | |
| 3,944,341 A | 3/1976 | Pomerantzeff | |
| 3,998,217 A | 12/1976 | Trumbull | |
| 4,010,741 A | 3/1977 | Gauthier | |
| 4,130,113 A | 12/1978 | Graham | |
| 4,141,364 A | 2/1979 | Schultze | |
| 4,254,763 A | 3/1981 | McCready | |
| 4,312,353 A | 1/1982 | Shahbabian | |
| 4,545,374 A | 10/1985 | Jacobson | |
| 4,589,868 A | 5/1986 | Dretler | |
| 4,716,901 A | 1/1988 | Jackson | |
| 4,739,762 A | 4/1988 | Palmaz | |
| 4,779,611 A | 10/1988 | Coil, Jr. | |
| 4,817,587 A | 4/1989 | Janese | |
| 4,896,669 A | 1/1990 | Bhate | |
| 5,032,113 A | 7/1991 | Burns | |
| 5,116,318 A | 5/1992 | Hillstead | |
| 5,139,511 A | 8/1992 | Gill | |
| 5,183,464 A | 2/1993 | Dubrul | |
| 5,312,417 A | 5/1994 | Wilk | |
| 5,320,611 A | 6/1994 | Bonutti | |
| 5,377,667 A | 1/1995 | Patton | |
| 5,383,889 A | 1/1995 | Chin | |
| 5,391,156 A | 2/1995 | Hildwein | |
| 5,391,178 A | 2/1995 | Yapor | |
| 5,425,730 A | 6/1995 | Luloh | |
| 5,431,676 A | 7/1995 | Dubul | |
| 5,452,732 A | 9/1995 | Bircoll | |
| 5,460,170 A | 10/1995 | Hammerslag | |
| 5,496,345 A | 3/1996 | Kieturakis | |
| 5,505,690 A | 4/1996 | Patton | |
| 5,514,153 A | 5/1996 | Bonutti | |
| 5,522,790 A | 6/1996 | Moll | |
| 5,580,344 A | 12/1996 | Hasson | |
| 5,607,441 A | 3/1997 | Sierocux et al. | |
| 5,653,726 A | 8/1997 | Kieturakis | |
| 5,678,572 A | 10/1997 | Huang | |
| 5,688,223 A | 11/1997 | Rosendalh | |
| 5,702,417 A | 12/1997 | Hermann | |
| 5,707,362 A * | 1/1998 | Yoon | 604/164.03 |
| 5,728,046 A | 3/1998 | Mayer | |
| 5,772,681 A | 6/1998 | Leoni | |
| 5,782,854 A | 7/1998 | Hermann | |
| 5,827,318 A | 10/1998 | Bonutti | |
| 5,827,319 A | 10/1998 | Carlson | |
| 5,830,191 A | 11/1998 | Hildwein | |
| 5,860,997 A | 1/1999 | Bonutti | |
| 5,865,802 A | 2/1999 | Yoon | |
| 5,888,196 A | 3/1999 | Bonutti | |
| 5,893,866 A | 4/1999 | Co | |
| 5,919,128 A | 7/1999 | Fitch | |
| 5,944,734 A | 8/1999 | Co | |
| 5,954,739 A | 9/1999 | Bonutti | |
| 5,957,832 A | 9/1999 | Taylor | |
| 5,967,970 A | 10/1999 | Cowan | |
| 5,993,472 A | 11/1999 | Hermann | |
| 6,004,337 A | 12/1999 | Echeverry | |
| 6,004,340 A | 12/1999 | Co | |
| 6,022,340 A | 2/2000 | Engelson | |
| 6,027,518 A * | 2/2000 | Gaber | 606/198 |
| 6,032,671 A | 3/2000 | Jervis | |
| 6,036,689 A | 3/2000 | Tu | |
| 6,079,761 A | 6/2000 | Sedeck | |
| 6,080,174 A | 6/2000 | Dubrul | |
| 6,083,154 A | 7/2000 | Liu | |
| 6,093,173 A | 7/2000 | Balceta et al. | |
| 6,102,928 A | 8/2000 | Bonutti | |
| 6,139,493 A | 10/2000 | Koros | |
| 6,171,299 B1 | 1/2001 | Bonutti | |
| 6,187,023 B1 | 2/2001 | Bonutti | |
| 6,206,826 B1 * | 3/2001 | Mathews et al. | 600/210 |
| 6,235,043 B1 | 5/2001 | Reiley | |
| 6,267,424 B1 | 7/2001 | Gillette | |
| 6,277,136 B1 | 8/2001 | Bonutti | |
| 6,312,443 B1 | 11/2001 | Stone | |
| 6,322,500 B1 | 11/2001 | Sikora | |
| 6,325,812 B1 | 12/2001 | Carlson | |
| 6,387,095 B1 | 5/2002 | Kennett et al. | |
| 6,436,119 B1 | 8/2002 | Erb | |
| 6,464,634 B1 | 10/2002 | Fraser | |
| 6,464,697 B1 | 10/2002 | Edwards | |
| 6,468,205 B1 | 10/2002 | Jervis | |
| 6,494,893 B2 | 12/2002 | Dubrul | |
| 6,564,078 B1 | 5/2003 | Marino | |
| 6,569,182 B1 | 5/2003 | Balceta | |
| 6,592,602 B1 | 7/2003 | Peartree | |
| 6,632,234 B2 | 10/2003 | Echeverry | |
| 6,689,152 B2 | 2/2004 | Balceta | |
| 6,692,462 B2 | 2/2004 | Carlson | |
| 6,814,715 B2 | 11/2004 | Bonutti | |
| 6,866,676 B2 | 3/2005 | Echeverry | |
| 6,869,398 B2 | 3/2005 | Obenchain | |
| 6,921,364 B2 | 7/2005 | Mollenauer | |
| 6,948,751 B2 | 9/2005 | Wooten | |
| 7,079,883 B2 | 7/2006 | Marino | |
| 7,195,592 B2 * | 3/2007 | Ravikumar et al. | 600/219 |
| 7,217,273 B2 | 5/2007 | Bonutti | |
| 7,235,064 B2 | 6/2007 | Hopper | |
| 7,294,136 B2 | 11/2007 | Dubrul | |
| 7,311,719 B2 | 12/2007 | Bonutti | |
| 7,326,226 B2 | 2/2008 | Root | |
| 7,329,268 B2 | 2/2008 | Van Nguyen | |
| 7,344,495 B2 | 3/2008 | Ravikumar | |
| 7,396,329 B2 | 7/2008 | Nakao | |
| 7,435,219 B2 | 10/2008 | Kim | |
| 7,476,232 B2 | 1/2009 | Deal | |
| 7,488,337 B2 | 2/2009 | Saab et al. | |
| 7,510,524 B2 | 3/2009 | Vayser | |
| 7,556,600 B2 | 7/2009 | Landry | |
| 7,641,664 B2 * | 1/2010 | Pagano | 606/92 |
| 7,645,232 B2 | 1/2010 | Shluzas | |
| 7,874,982 B2 | 1/2011 | Selover | |
| 7,909,832 B2 | 3/2011 | Michelson | |
| 7,935,053 B2 | 5/2011 | Karpowicz | |
| 7,985,179 B2 | 7/2011 | Gephart | |
| 7,988,624 B2 | 8/2011 | Smith | |
| 8,105,236 B2 | 1/2012 | Malandain | |
| 8,137,284 B2 | 3/2012 | Miles | |
| 8,172,750 B2 | 5/2012 | Miles | |
| 8,182,423 B2 | 5/2012 | Miles | |
| 2001/0039430 A1 | 11/2001 | Dubrul | |
| 2002/0193822 A1 | 12/2002 | Hung | |
| 2003/0018352 A1 | 1/2003 | Mollenauer | |
| 2003/0023259 A1 | 1/2003 | Dubrul | |
| 2003/0181939 A1 | 9/2003 | Bonutti | |

(56) References Cited

U.S. PATENT DOCUMENTS

| | | |
|---|---|---|
| 2003/0195405 A1 | 10/2003 | Marino |
| 2003/0225432 A1 | 12/2003 | Baptiste |
| 2003/0233115 A1 | 12/2003 | Eversull |
| 2004/0243158 A1 | 12/2004 | Konstantino |
| 2004/0243167 A1 | 12/2004 | Tanaka et al. |
| 2005/0124937 A1 | 6/2005 | Kick |
| 2005/0182436 A1 | 8/2005 | Chopra |
| 2005/0234493 A1 | 10/2005 | Carr |
| 2006/0004398 A1* | 1/2006 | Binder et al. .................. 606/191 |
| 2006/0052750 A1 | 3/2006 | Lenker |
| 2006/0135981 A1 | 6/2006 | Lenker |
| 2006/0135987 A1 | 6/2006 | Jones |
| 2006/0224044 A1* | 10/2006 | Marchek et al. .............. 600/233 |
| 2007/0010716 A1* | 1/2007 | Malandain et al. ........... 600/224 |
| 2007/0032703 A1 | 2/2007 | Sankaran |
| 2007/0049962 A1 | 3/2007 | Marino |
| 2007/0270653 A1 | 11/2007 | Vayser |
| 2008/0064945 A1 | 3/2008 | Marino |
| 2008/0065135 A1 | 3/2008 | Marino |
| 2008/0065140 A1 | 3/2008 | Bonutti |
| 2008/0065144 A1 | 3/2008 | Marino |
| 2008/0103519 A1 | 5/2008 | Bonutti |
| 2008/0109026 A1 | 5/2008 | Kassam |
| 2008/0132764 A1 | 6/2008 | Hamada |
| 2008/0147109 A1 | 6/2008 | Kambin |
| 2008/0221586 A1 | 9/2008 | Garcia-Bengochea |
| 2008/0255563 A1 | 10/2008 | Farr |
| 2009/0036744 A1 | 2/2009 | Vayser |
| 2009/0062871 A1 | 3/2009 | Chin |
| 2010/0041955 A1 | 2/2010 | Grey |
| 2010/0160947 A1 | 6/2010 | Akyuz et al. |
| 2012/0010472 A1 | 1/2012 | Spann |
| 2012/0101341 A1 | 4/2012 | Malandain |

OTHER PUBLICATIONS

Aesculap Spine; Caspar Cervical Retractor System, Product Brochure Apr. 2009 Doc# 510.
Zimmer; ARAS Retractor, Surgical Technique L1377 Rev. A 2007.
Depuy; Pipeline Concorde, Surgical Technique Jul. 2007 M102-20-001.
Zimmer Spine; Harmony Retractor System, Surgical Technique L1477 Rev. A Aug. 2009.
LANX; Timberline Lateral Fusion System, Surgical Technique LIT8710-0111.03.
Medtronic; Mast Quadrant, Product Brochure 2005 MLITQUDST5.
Synthes; Oracle Spacer, Technique Guide Dec. 2010 J8158-C.
K2M; Tera Nova, Product Brochure 2012 K2-15-7002-01 Rev.3.
Biomet Spine; VuePASS, Surgical Technique Jun. 2007 P/N 216001L.
NuVasive; Maxcess-XLIF, Surgical Technique 2007 9500138 A.0.

* cited by examiner

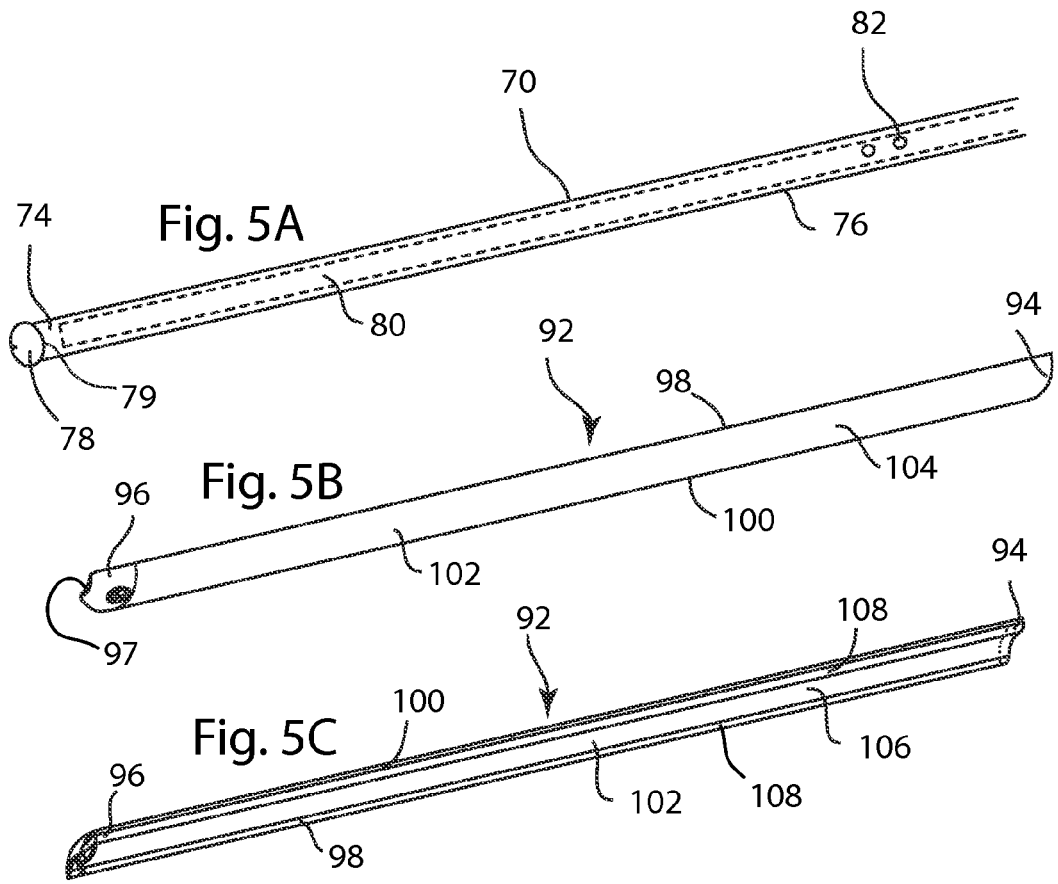
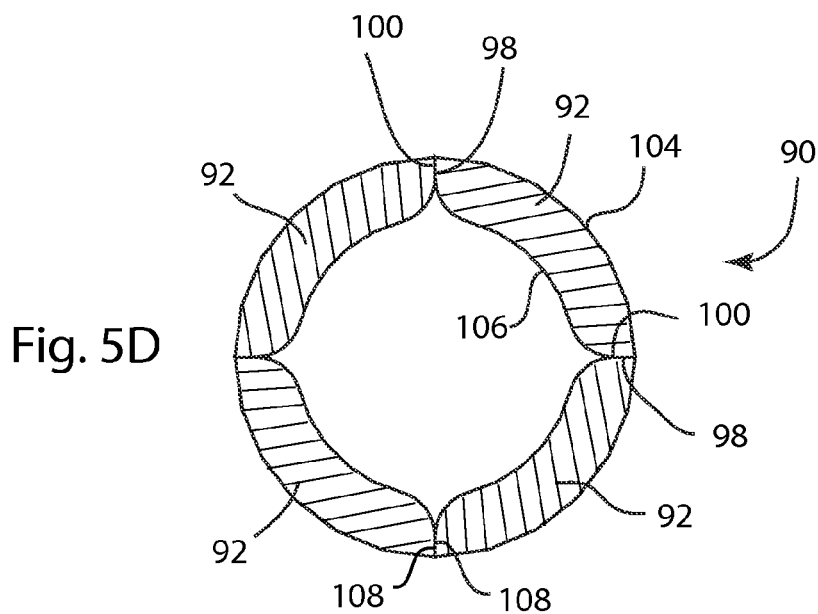

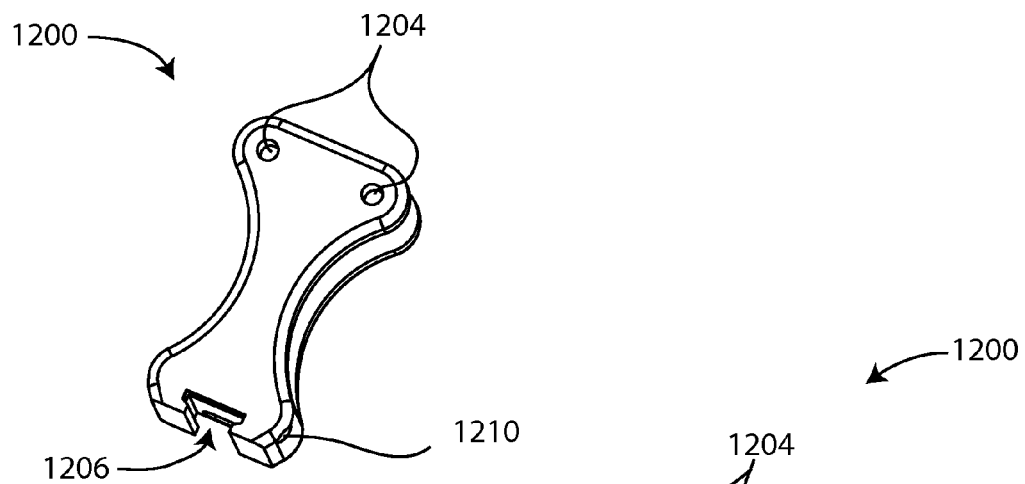
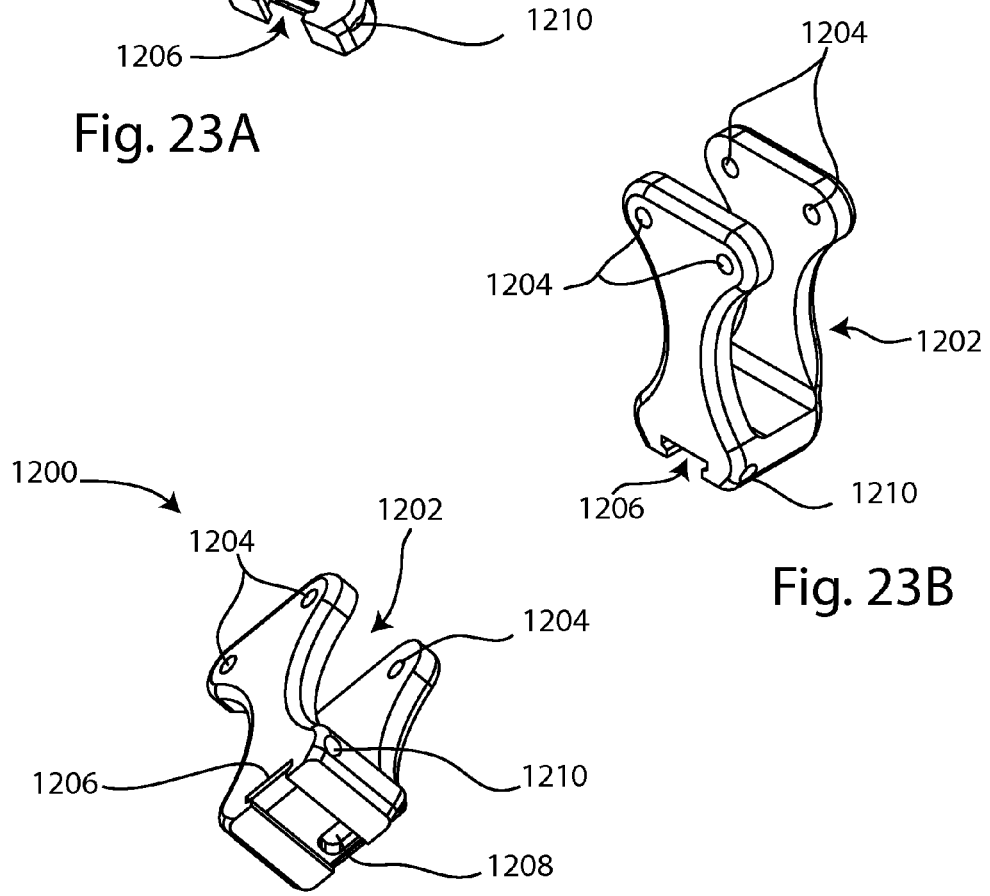
Fig. 23A
Fig. 23B
Fig. 23C

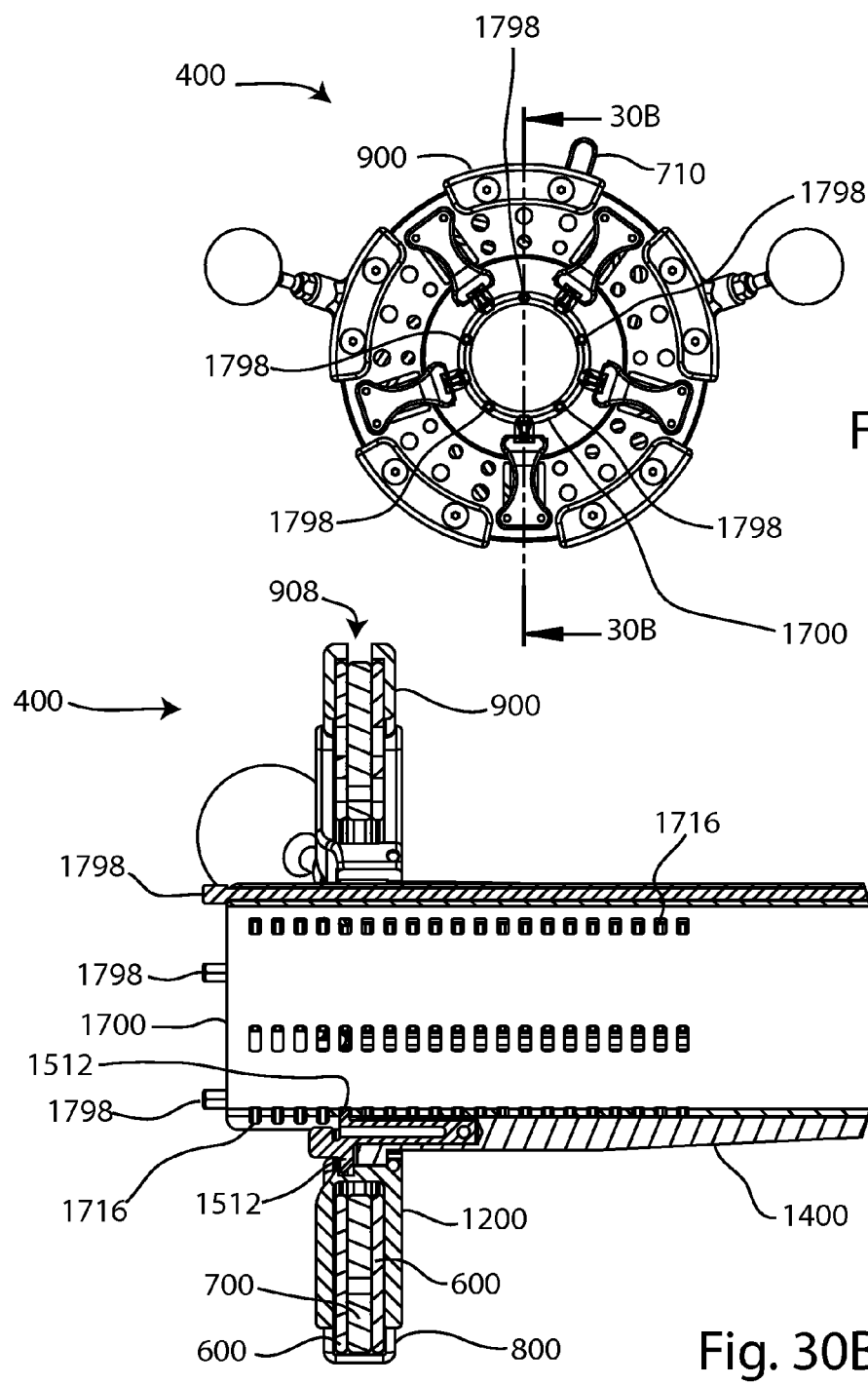

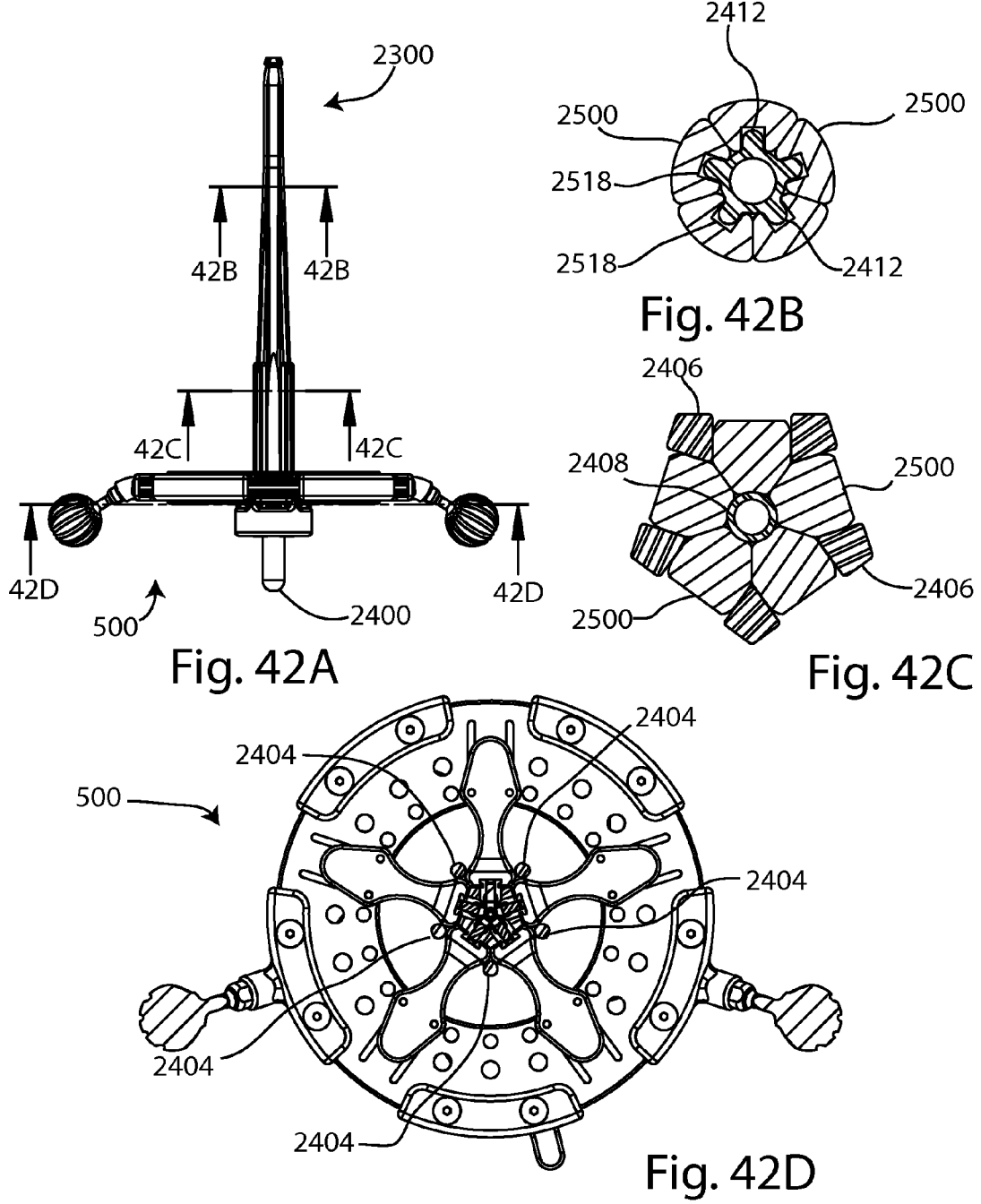

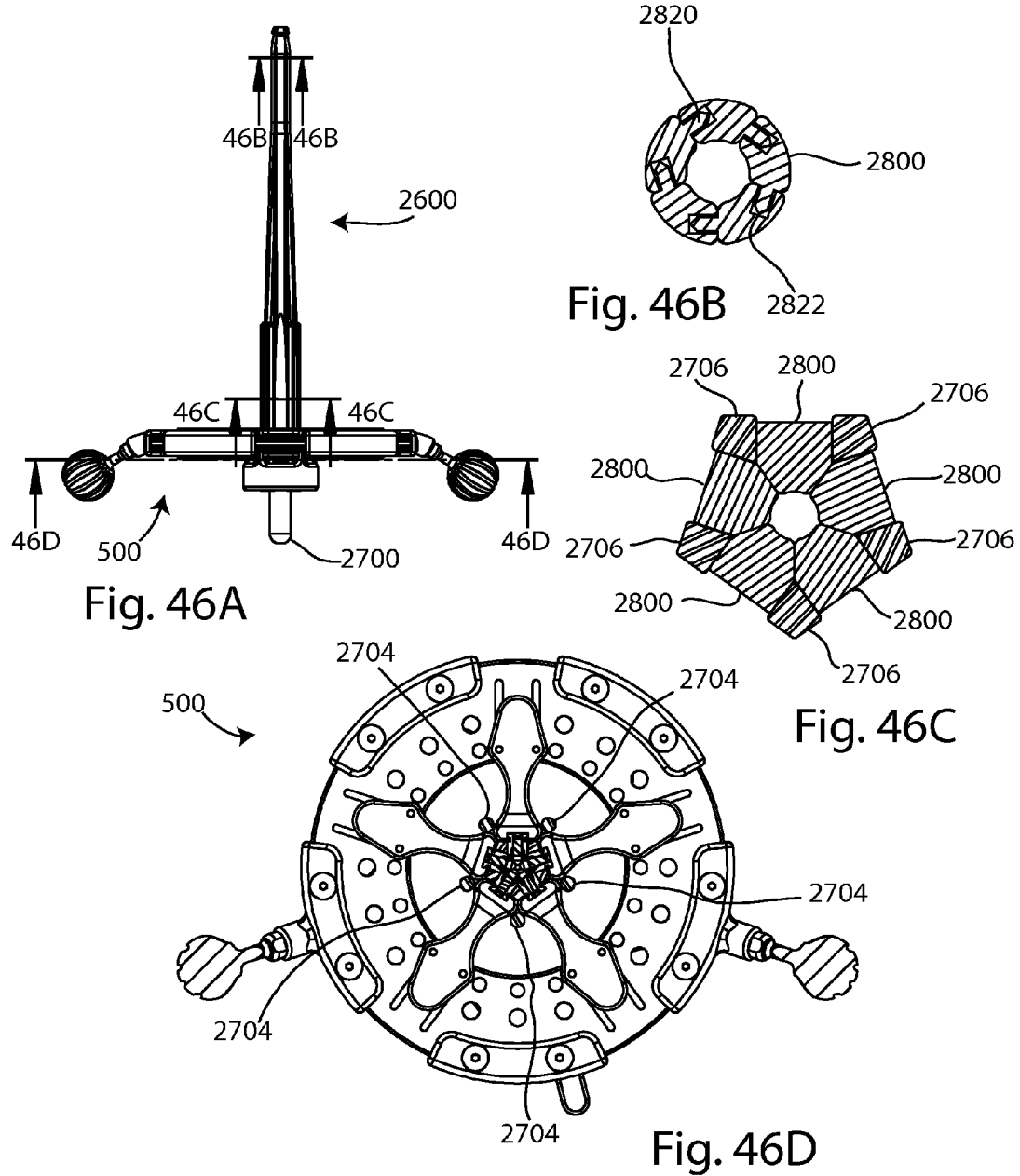

LATERAL ACCESS SYSTEM FOR THE LUMBAR SPINE

CROSS-REFERENCE TO RELATED APPLICATIONS

This application claims the benefit of the filing date of:
U.S. Application No. 61/324,185, filed Apr. 14, 2010, entitled LATERAL ACCESS SYSTEM FOR THE LUMBAR SPINE, and
U.S. Application No. 61/442,608, filed Feb. 14, 2011, entitled LATERAL ACCESS SYSTEM FOR THE LUMBAR SPINE.
This application is also a continuation-in-part of:
U.S. application Ser. No. 12/640,413, filed Dec. 17, 2009, entitled SYSTEMS AND METHODS FOR DILATION AND DISSECTION OF TISSUES, which is pending.
U.S. application Ser. No. 12/640,413 claims the benefit of:
U.S. Application No. 61/138,629, filed Dec. 18, 2008, entitled SYSTEMS AND METHODS FOR DILATION AND DISSECTION OF TISSUES DURING LATERAL SPINE ACCESS SURGERY, and
U.S. Application No. 61/166,069, filed Apr. 2, 2009, entitled SYSTEM AND METHOD FOR DILATION AND DISSECTION OF TISSUES.
The above-identified documents are incorporated herein by reference.

BACKGROUND OF THE INVENTION

1. The Field of the Invention

The present disclosure relates to orthopaedics, and more particularly, to providing access to a surgical site in the body through the use of an expandable minimally invasive dilation device.

2. The Relevant Technology

Many spinal orthopaedic procedures including discectomy, implantation of motion preservation devices, total disc replacement, and implantation of interbody devices require unimpeded access to a targeted portion of the spinal column. Providing access to the targeted area may require forming a passageway through muscles, fascia and other tissues. Current surgical access systems utilize a series of sequential dilators, or a mechanical retractor system with at least one dilating cannula.

There are several disadvantages associated with sequential dilators. Sequential dilator systems can shear the tissues through which they are advanced. These tissues can include muscle, nerves, blood vessels, and organs. In addition, the tissues at the distal end of the dilators can be crushed against bone or other soft tissues rather than properly separated. As multiple dilators are deployed to enlarge a space, the tissues may be repeatedly injured as each dilator is advanced through the same tissues.

Accordingly, there is a need in the art for systems and methods that facilitate access to the spine, while minimizing trauma to surrounding tissues and avoiding time-consuming and unnecessary repetitive steps. Keeping the overall diameter and the number of passes of the cannulas to a minimum may minimize the trauma to the surrounding structures. Such systems and methods can simplify surgical procedures and expedite patient recovery. Ultimately, reducing the invasiveness of the procedure will result in faster recoveries and improved patient outcomes.

BRIEF DESCRIPTION OF THE DRAWINGS

Various embodiments will now be discussed with reference to the appended drawings. It is appreciated that these drawings depict only typical embodiments and are therefore not to be considered limiting of the scope of the invention as set forth in the claims.

FIG. 5A is a perspective view of a distal portion of the stylus of FIG. 1A, with dashed lines representing an inner bore;

FIG. 5B is a perspective view of an outer side of one arm of the plurality of arms of FIG. 1A;

FIG. 5C is a perspective view of an inner side of one arm of the plurality of arms of FIG. 1A;

FIG. 5D is an enlarged cross-sectional transverse view of the plurality of arms of FIG. 1A in the closed configuration;

FIG. 23A is a perspective view of an arm clamp of the hub assembly of FIG. 17; FIG. 23B is another perspective view of the arm clamp of FIG. 23A from another direction; and FIG. 23C is yet another perspective view of the arm clamp of FIG. 23A from yet another direction;

FIG. 30A is a top view of the tissue dilation device of FIG. 16 in an open configuration, operatively assembled with one of the cannulas of FIG. 29; and FIG. 30B is a cross section view of the tissue dilation device and cannula of FIG. 30A taken along line 30B-30B shown in FIG. 30A;

FIG. 42A is a front view of the hub assembly, arm assemblies, and retainer of FIG. 41A; FIG. 42B is a cross section view of the hub assembly, arm assemblies, and retainer of FIG. 41A taken along line 42B-42B of FIG. 42A; FIG. 42C is a cross section view of the hub assembly, arm assemblies, and retainer of FIG. 41A taken along line 42C-42C of FIG. 42A; and FIG. 42D is a cross section view of the hub assembly, arm assemblies, and retainer of FIG. 41A taken along line 42D-42D of FIG. 42A;

FIG. 46A is a front view of the hub assembly of FIG. 17 operatively assembled with a plurality of arm assemblies and a retainer; FIG. 46B is a cross section view of the hub assembly, arm assemblies, and retainer of FIG. 46A taken along line 46B-46B of FIG. 46A; FIG. 46C is a cross section view of the hub assembly, arm assemblies, and retainer of FIG. 46A taken along line 46C-46C of FIG. 46A; and FIG. 46D is a cross section view of the hub assembly, arm assemblies, and retainer of FIG. 46A taken along line 46D-46D of FIG. 46A;

DETAILED DESCRIPTION OF THE PREFERRED EMBODIMENTS

Figure 1:
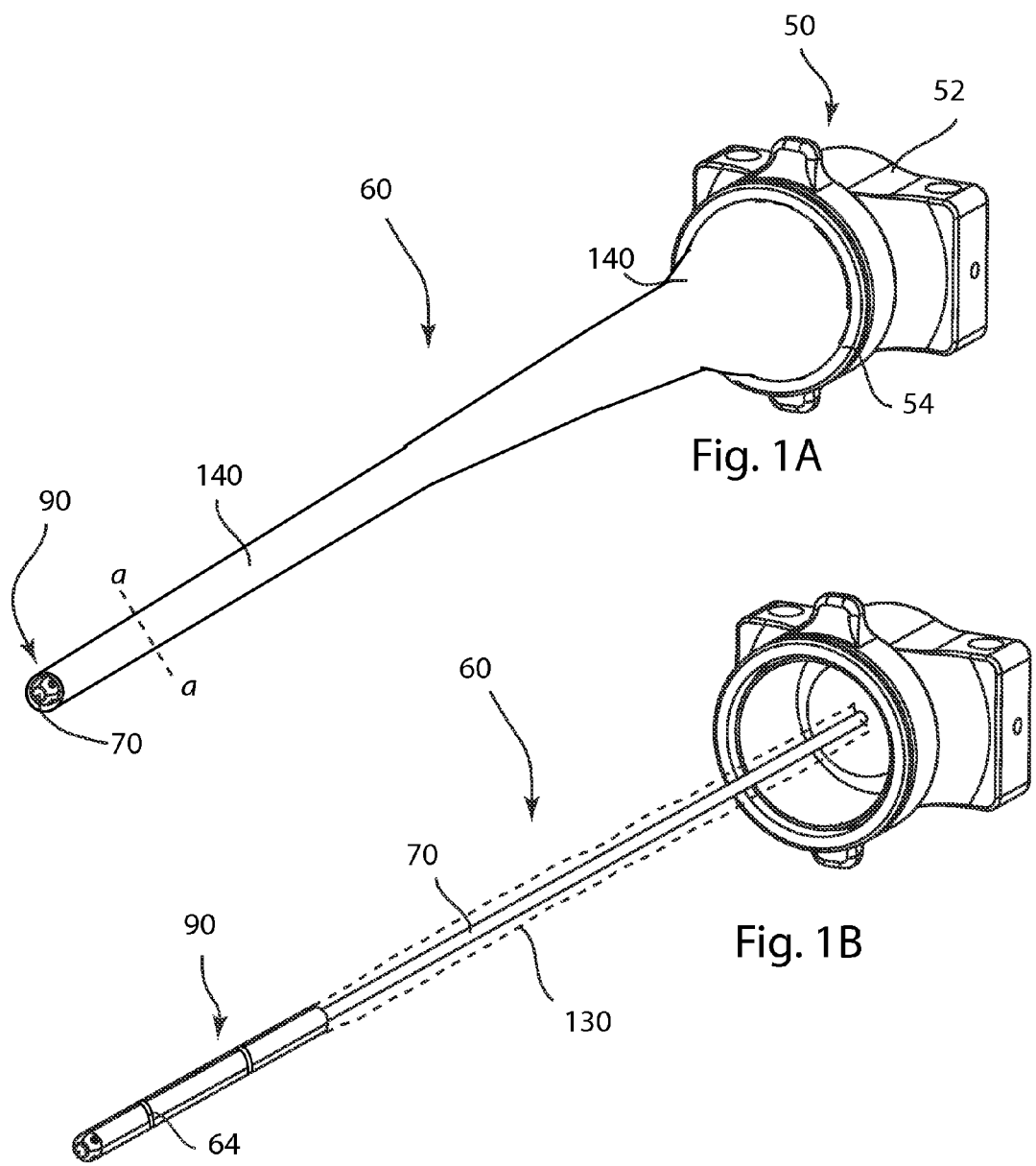
FIG. 1A is a perspective view of a tissue dilation device in a closed configuration and attached to a hub, the device comprising a stylus, a balloon, a plurality of arms surrounding the stylus, an inner mesh, and an outer sheath.
FIG. 1B is a perspective view of the tissue dilation device of FIG. 1A in the closed configuration, with the outer sheath not depicted, and dashed lines representing the inner mesh.

The present disclosure relates to systems and methods for dilating tissues to provide access to intervertebral space or other targeted areas. Those of skill in the art will recognize that the following description is merely illustrative of principles which may be applied in various ways to provide many different alternative embodiments. This description is made for the purpose of illustrating the general principles and is not meant to limit the inventive concepts in the appended claims.

The present invention provides access to the spine through the use of a minimally invasive expandable dilation device. The device may be placed within the tissue with a minimal profile, yet has a high expansion ratio, with the result that the expanded device provides an optimally sized passageway allowing access to the targeted spinal area, with minimal impact on surrounding tissues. A single device is advanced into the tissues to be dilated, and expanded from within. Thus additional steps of introducing successive dilators are avoided, along with repetitive damage to the tissues caused by forcing dilator after dilator through the tissues.

FIGS. 1-6B display views of one embodiment of a dilation device 60. The dilation device 60 comprises an obturator or stylus 70, a plurality of rigid arms 90, a balloon 110, a flexible inner mesh 130, and an optional, flexible outer sleeve or sheath 140. A portion of the dilation device may be introduced into a muscle, and the dilation device expanded from a closed configuration to an open configuration to dissect and separate the muscle fibers and form a passage through the muscle. After expansion, the stylus, balloon and inner mesh may be removed, leaving an open passage through the muscle, through which instruments, implants and other materials may be passed to perform one or more surgical procedures.

Referring to FIGS. 1A and 1B, the dilation device 60 is shown in a closed configuration, partially extending through a hub 50. The hub 50 comprises a hub body 52 and a collet 54, and is attachable to a surgical table mounted support system (not shown), which may provide stability and support to the hub and dilation device during surgical procedures. In FIG. 1A, of the device 60 only the optional outer sleeve 140, and the distal ends of the plurality of arms 90 and the stylus 70 are visible, as the outer sleeve 140 obscures most of the device. The outer sleeve 140 is securely attached to the plurality of arms, and circumferentially securely attached to the collet, forming a barrier around the remainder of the device. FIG. 1B depicts the device without the outer sleeve 140, and with dashed lines representing the inner mesh 130. The balloon 110 is mounted circumferentially on the stylus 70 toward the distal end of the stylus and extends proximally along a portion of the stylus. The plurality of arms 90 may completely surround the balloon in the closed configuration; hence the balloon is not visible in FIGS. 1A and 1B. The inner mesh 130 surrounds the balloon, interposed between the balloon and the plurality of arms, and extending from a distal end of the plurality of arms toward the collet 54. The inner mesh may be attached to the stylus. The maximum outer diameter of the device 60 in the closed configuration, measured normal to the longitudinal axis of the stylus and rigid arms, such as along line a-a, may range from 5 to 15 millimeters.

Device 60 may further comprise one or more retention bands 64 which are placed around the plurality of arms when the device is in the closed configuration, to aid in holding the device closed. The bands may comprise a biocompatible polymer, which may be bio-absorbable, and have a generally circular ring shape. The bands may be heat-shrunk about the closed device. During expansion, as the arms move radial-laterally relative to one another, the force of the moving arms will stretch and ultimately break the band(s). Any of the dilation devices disclosed herein may comprise these retention bands.

Figure 2:
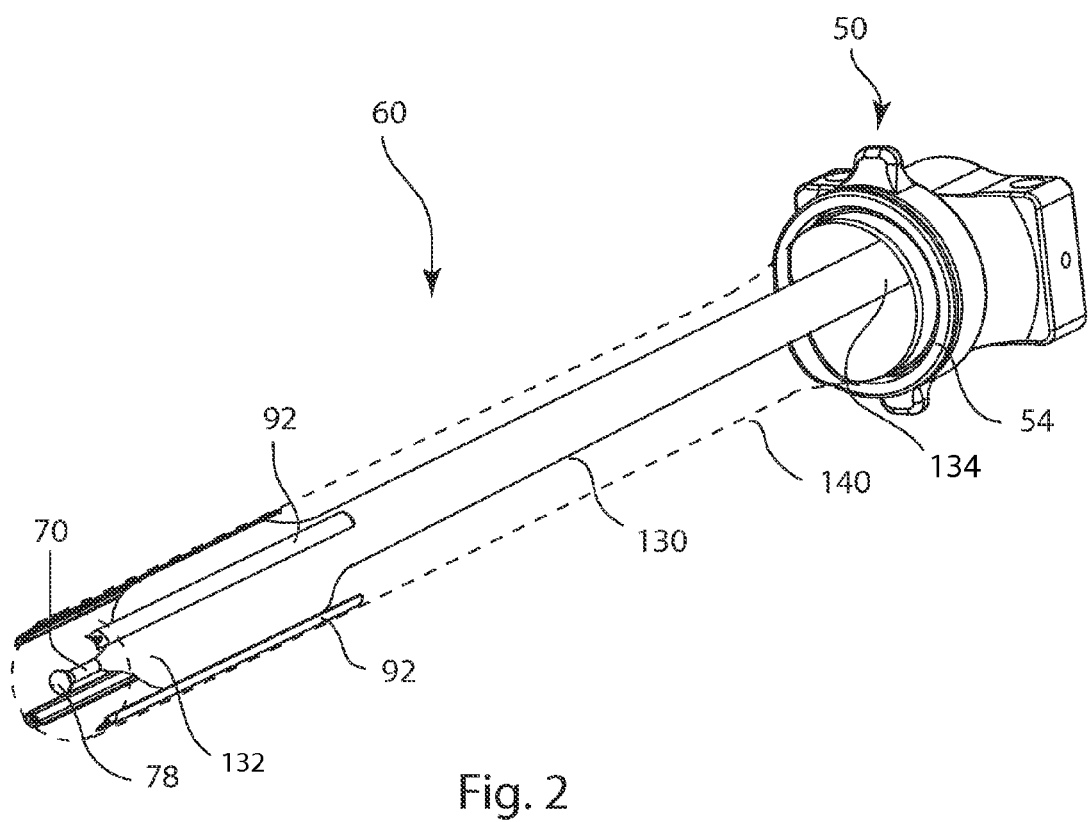
FIG. 2 is a perspective view of the tissue dilation device of FIG. 1A, with the balloon inflated and the device in an expanded configuration, and dashed lines representing the outer sheath.

FIG. 2 shows the dilation device 60 in an expanded, or open configuration. The outer sleeve 140 is not depicted but its location is indicated with dashed lines. A distal portion 132 of the inner mesh 130 surrounds the balloon, and in this embodiment the distal end of the mesh is attached to the stylus. A proximal end of the mesh 134 extends through the collet 54, surrounding the stylus.

Figure 3:
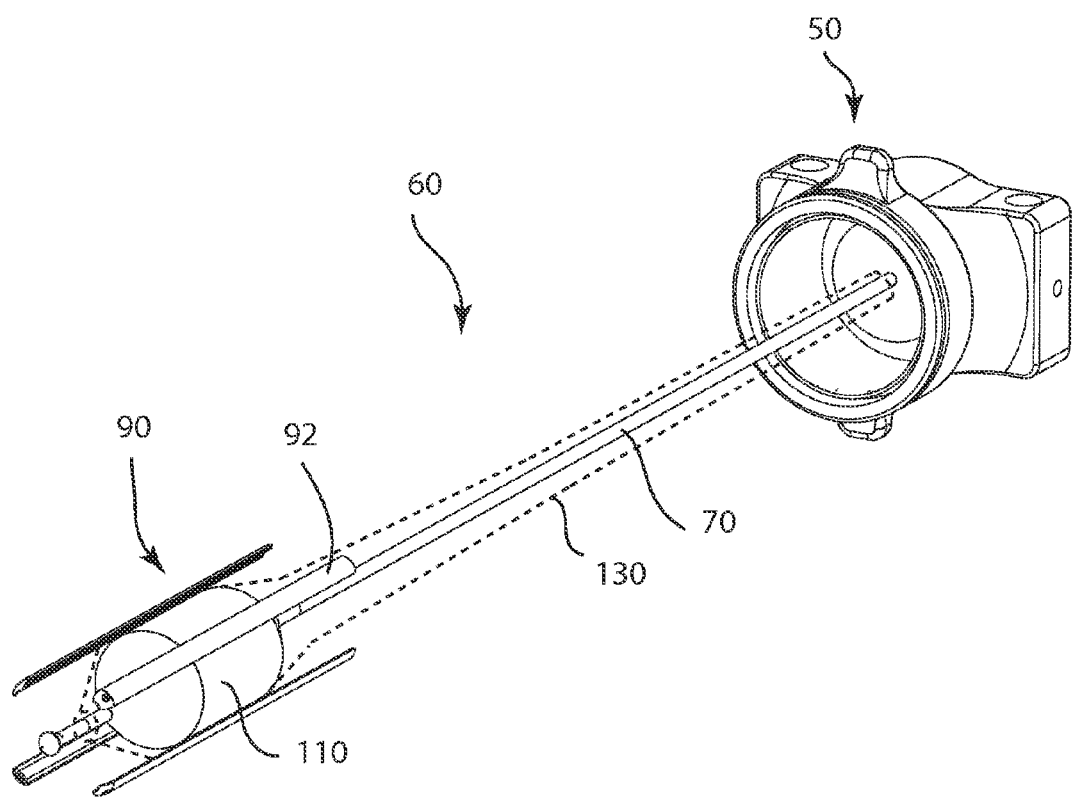
FIG. 3 is a perspective view of the tissue dilation device of FIG. 1A in the expanded configuration, with the outer sheath not depicted, and dashed lines representing the inner mesh.
Figure 4A:
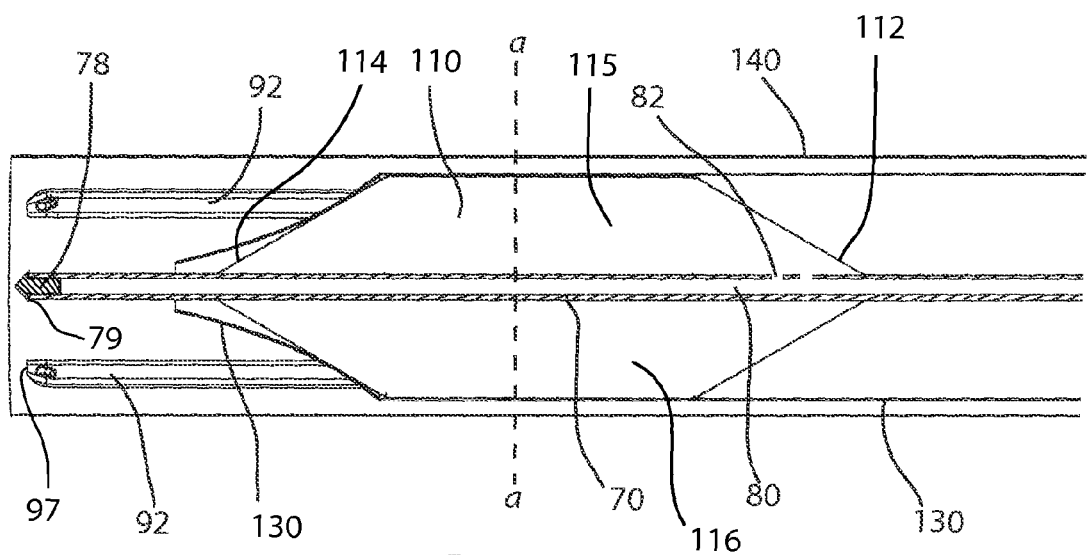
FIG. 4A is an enlarged cross-sectional longitudinal view of the distal end of the tissue dilation device of FIG. 1A in the expanded configuration.
Figure 4B:
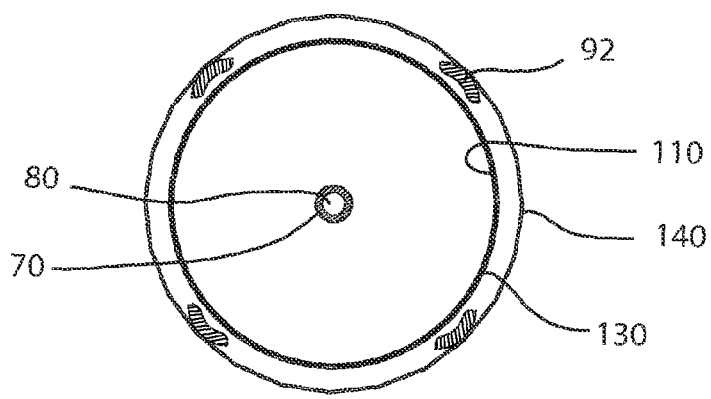
FIG. 4B is an enlarged cross-sectional end view of the distal end of the of the tissue dilation device of FIG. 1A in the expanded configuration, taken along line a-a of FIG. 4A.

FIG. 3 shows the dilation device 60 in the expanded configuration, without the outer sleeve, and the inner mesh is indicated by dashed lines. FIG. 4A shows an enlarged longitudinal cross-sectional view of a distal portion of the device 60 in the expanded or open configuration. FIG. 4B shows a further enlarged cross sectional view of the distal end of the device 60 in the open configuration, taken along line a-a of FIG. 4A. Each end of the balloon 110 is attached to the stylus 70. To attain the open configuration, fluid is introduced through the stylus into the balloon 110, inflating the balloon. As the balloon 110 is actuated by inflation, it expands radially, and an outer surface of the balloon pushes against the plurality of rigid arms 90, and each individual arm 92 is displaced radially outward and laterally away from the adjacent arms. The inner mesh 130, which surrounds a body of the balloon, also expands or unfolds radially outward, generally conforming to the shape of the balloon where it is adjacent to the balloon. The outer sleeve 140 also expands or unfolds with expansion of the device. After expansion of the device to the open configuration, the stylus 70 and attached balloon 110 and inner mesh 130 may be withdrawn proximally, leaving an open passageway extending from the hub 50 to the distal ends of the arms 92, the open passageway lined by the arms and the outer sleeve. The device 60 comprises a substantially cylindrical shape in both the closed configuration, as seen in FIG. 1A, and the open configuration, as seen in FIG. 2.

FIGS. 5A through 5D display details of the stylus 70 and arms 92. Referring to FIGS. 3, 4A and 5A, stylus 70 comprises a proximal end 72, distal end 74, and a shaft 76 extending between the proximal and distal ends. The stylus may also be an obturator or a hypotube, comprising stainless steel or another biocompatible metal. A stylus tip 78 is located at the distal end and may be formed integrally with the stylus, or formed separately from the stylus and rigidly secured to the stylus. The tip 78 may be blunt, to separate and push aside muscle fibers with minimal trauma to the fibers during advancement of the stylus into the muscle. In some embodiments, the tip may be conical, pointed and/or comprise a cutting edge. In some embodiments, the stylus distal end may further comprise connecting features which cooperate with complementary connecting features on the rigid arms to place the arms in a predetermined longitudinal alignment with the stylus when the connecting features are engaged with one another. The stylus may be partially hollow, having an inner bore 80 extending from an opening at the proximal end, to or toward the distal end. One or more ports 82 may penetrate from the bore 80 to the outside of the shaft 76, through which fluid may flow to inflate the balloon during dilation. A luer (not shown) may be attached to the proximal end of the stylus, in communication with the bore 80, for introduction of fluids into the stylus bore.

Referring to FIGS. 3 through 5D, the plurality of rigid arms 90 may comprise four or more individual arms 92. Each arm 92 may be identical to each other arm, and comprises a proximal end 94, a distal end 96, a first lateral edge 98 and a second lateral edge 100 opposite the first lateral edge. A shaft 102 extends between the proximal and distal ends, bounded laterally by the lateral edges 98, 100. An outer surface 104 which may be convexly curved covers one side of the arm, while an inner surface 106 which may be concavely curved covers the opposite side. Each entire arm 92 may be curved about its longitudinal axis, such that when the arms are positioned in a closed configuration so that their lateral edges are adjacent one another in contacting alignment as in FIGS. 1B, 5D, and 6A, a closed cylinder is formed. The inner diameter of the closed cylinder is sized to receive the stylus 70 and the uninflated balloon 110. The arms may include holes or other features used in secure attachment of the outer sleeve to the arms via sutures, pins, or other attachment mechanisms. In the embodiment shown in FIGS. 1B-3, the arms extend along only a portion of the stylus. In other embodiments, the arms may be longer, and can extend the entire length of the stylus and/or extend out of the hub 50. Each arm 92 may flare or curve outward at its distal end, which may aid in keeping tissues retained during dilation or expansion.

The arm distal end 96 may comprise an arm connection feature which is shaped to engage with a corresponding stylus connection feature to place the arm in a predetermined longitudinal alignment with the stylus. With reference to FIGS. 4A, 5A and 5B, the arm connection feature may comprise a curved distal edge 97. The stylus connection feature may comprise a segment of an overhanging lip 79. The lip 79 comprises a circular flange on the stylus tip 78, which may project outward from the stylus tip. When an arm curved distal end 97 is positioned in abutment with a correspondingly curved segment of the lip 79 such that the entire curved distal end is in contact with the lip segment, the arm is placed in a predetermined longitudinal alignment with the stylus.

The arm lateral edges 98, 102 may comprise complementary engagement features which cooperate with the engagement features on adjacent arms to place the arms in contacting longitudinal alignment with one another along their first and second lateral edges when the arms are in the closed configuration. In one embodiment, the engagement features may comprise planar portions wherein the first lateral edge comprises a planar surface 108 which engages a complementary planar surface on the adjacent second lateral edge. In another embodiment, the engagement features comprise tongue-in-groove features wherein the first lateral edge comprises a tongue while the second lateral edge comprises a groove shaped to receive the tongue. In yet another embodiment, the engagement features may comprise alternating edge extensions with bores shaped to receive a longitudinal member such as a wire or suture, so that the edges may be temporarily laced together. In the closed configuration the longitudinal member extends through the bores and the arms are retained in contacting longitudinal alignment; when the longitudinal member is removed the arms are free to disengage and move apart from one another.

The arms may be at least partially radiolucent, so as not to compromise visualization of procedures during use of the device with fluoroscopy. Alternatively, the arms may be at least partially radiopaque, to assist with positioning and location of the system under fluoroscopy. The arms may comprise metals such as aluminum, stainless steel, titanium, and other biocompatible metals. The arms may also comprise high density plastics such as Delrin, Radel, Udel, poly ether ether ketone (PEEK), polycarbonate, and acrylonitrile butadiene styrene (ABS), among others. Barium sulphate may be added to constituent plastic materials to provide increased radiopacity.

With reference to FIG. 4A, the balloon 110 comprises a proximal end 112, a distal end 114, and a substantially cylindrical balloon body 116 extending therebetween. At the proximal 112 and distal 114 ends, the balloon is circumferentially attached to the stylus through adhesives or other bonding methods such that when fluids are introduced into a balloon lumen 115, the fluids cannot escape at the points of attachment to the stylus 70. As fluid is introduced into the balloon 110 from the stylus 70 through the ports 82, the balloon may inflate proximally to distally. As the proximal end of the balloon inflates, the arms 92 may be pushed slightly distally, then radially outward as the inflation continues distally. The proximal ends 94 of the arms may be pushed radially outward before, or at the same time, as the distal ends 96 of the arms 92.

The balloon may be opaque or translucent, and the balloon may be compliant or non-compliant. A compliant balloon may allow for an even distribution of force on the rigid arms and ultimately the surrounding tissue. A non-compliant balloon may allow for an uneven distribution of force and as such may be well suited for dissection of tissues. The shape of the balloon may be optimized to best suit the physiology and tissue it will dissect. For example, a round balloon may produce uniform force distribution and create a localized open space. An elongated balloon may produce distal expansion to create space at the distal end of the device. The balloon may comprise polyethylene, polyethylene terephthalate (PET), polytetrafluoroethylene (PTFE), nylon, Dacron, polyurethane, or other compliant or non-compliant polymers.

The inner mesh 130 may be fixed to the stylus at a location distal to the distal end of the balloon, extending to or toward the proximal end of the stylus. The inner mesh 130 is generally tubular and flexible, able to conform to the shape of the balloon, and may be permeable or non-permeable. The inner mesh may be of an indeterminate shape or a pre-formed shape. The mesh may comprise polypropylene, polyethylene (PE), polyethylene terephthalate (PET), poly ether ether ketone (PEEK), nylon, ultra-high molecular weight polyethylene (UHMWPE), or any other biocompatible polymer, or a combination thereof. In some embodiments, the inner mesh may be formed such that as a portion of the inner mesh is expanded by the balloon or dilation member, the length of the inner mesh is foreshortened.

In some embodiments, the dilation device 60 may further comprise an outer mesh or sheath 140 which may circumferentially surround the rigid arms and stylus, to further retain and protect bodily tissues during dilation. In other embodiments, the outer sheath may be positioned inside the arms, but outside of and circumferentially surrounding the inner mesh, balloon and stylus. The outer sheath may prevent pinching of tissues and/or migration of tissues between the rigid arms during the dilation process. The outer sheath is securely attached to the arms, whether inside or outside, by adhesive, suturing, and/or a mechanical fastening device such as a pin. The sheath 140 may be generally tubular in form, with open distal and proximal ends. At or toward its distal end, the sheath may be attached to the plurality of arms. At its proximal end, the sheath may be circumferentially attached to the collet 54, via an o-ring or another fastener. In some embodiments, the outer sheath comprises a mesh interwoven with a secondary material that is conductive. The conductive nature of the mesh may be used to oblate tissue or used in a more diagnostic mode, such as detecting nerve tissue in conjunction with an electromyography (EMG) device. The outer sheath may comprise the same materials as the inner mesh.

Figure 6A:
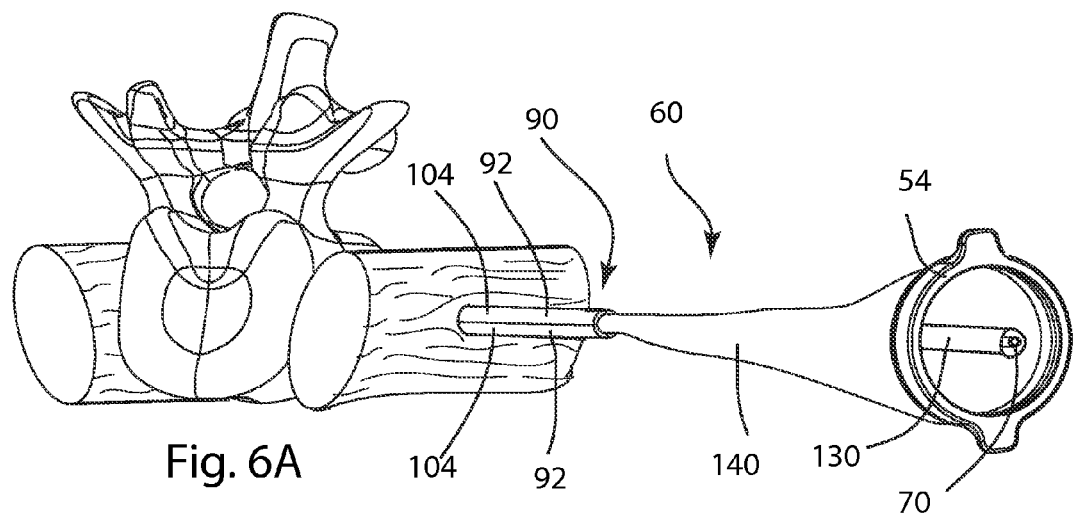
FIG. 6A is a perspective view of the tissue dilation device of FIG. 1A in the closed configuration, with the distal end inserted into a psoas muscle adjacent a vertebra, and the proximal end attached to the hub.
Figure 6B:
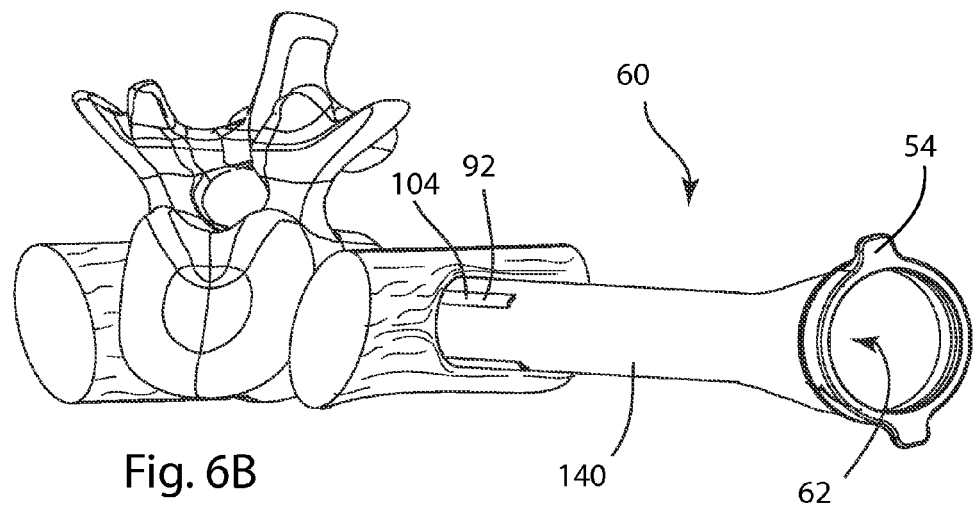
FIG. 6B is a perspective view of the tissue dilation device of FIG. 6A in the open configuration, with the stylus, balloon, and inner mesh withdrawn, and an open passageway extending through the hub, dilation device and psoas muscle.

FIG. 6A shows the device 60 in the closed configuration, advanced into a muscle, while FIG. 6B shows the device 60 in the open configuration, dilating the muscle to provide a passageway through the muscle. In FIGS. 6A and 6B, the outer sheath 140 is positioned inside the plurality of arms 90. Referring to FIG. 6A, the device 60 has been partially advanced into the psoas muscle adjacent the spine. The stylus 70 and closed plurality of arms 90 have penetrated the muscle, dissecting the muscle fibers. As the device is introduced, it may be rotated such that the outer surfaces 104 of the arms 92 are placed in a preferred orientation relative to the muscle fibers, so that the fibers may be primarily pushed aside, instead of torn, during dilation. For example, placing the device so that the outer surfaces 104 of the arms 92 are at approximately 45° relative to the longitudinal axis of the muscle fibers may be preferable, as shown in FIGS. 6A and 6B. Fluid is introduced into the bore of the stylus, where it passes through the ports 82 into the balloon 110, inflating the balloon and causing it to expand radially. As the balloon expands, the surrounding inner mesh 130 expands, and the arms 92 are forced radially outward and are radial-laterally displaced from one another, as seen in FIGS. 6B and 4B. The surrounding muscle fibers are dissected and the muscle is dilated, creating a passageway through the muscle to the spine.

After the balloon 110 has been inflated a desired amount, the stylus, balloon and inner mesh may be removed from the device 60, leaving the expanded arms 90 and outer mesh 140 surrounding an open passageway 62. Before or after removal of the stylus, balloon and inner mesh, a rigid cannula may be longitudinally inserted into the passageway 62, inside the arms 90 and outer mesh 140, to further hold the passageway open; the cannula forming an inner wall of the passageway. Instruments, implants and other materials may be passed through the passageway to perform surgical procedures. In the open configuration, the maximum outer diameter of the device 60, measured normal to the longitudinal axis of the stylus and rigid arms such as along line a-a in FIG. 4A, may range from 25 to 40 millimeters. An expansion ratio of the device may be measured as the ratio of maximum outer diameter of the device in the open configuration to the maximum outer diameter of the device in the closed configuration. The expansion ratio of device 60 may range from 2.5 to 8.0. In some embodiments, the expansion ratio may range from 3.0 to 7.5; in other embodiments, the expansion ratio may range from 4.0 to 7.0; while in other embodiments, the expansion ratio may range from 5 to 6.5. In a preferred embodiment, the expansion ratio may be at least 6.0.

FIGS. 7-10 illustrate another embodiment of an minimally invasive expandable dilation device. Dilation device 160 comprises a curved stylus 170, a plurality of rigid curved arms 190 radially arrayed about the stylus, and two balloons which are circumferentially attached to the stylus. Dilation device 160 may be used in a postero-lateral approach to dilate and form a passageway through the psoas muscle in order to obtain access to an intervertebral space. In other embodiments, one balloon may be attached to the curved stylus, or a plurality of balloons. In yet other embodiments, at least one cannula may be introduced into the space defined by the arms to expand the arms apart, instead of one or more balloons. Device 170 may be used to create a curved passageway through the psoas muscle, and/or to create a curved passageway through another muscle or set of tissues.

Figure 7:
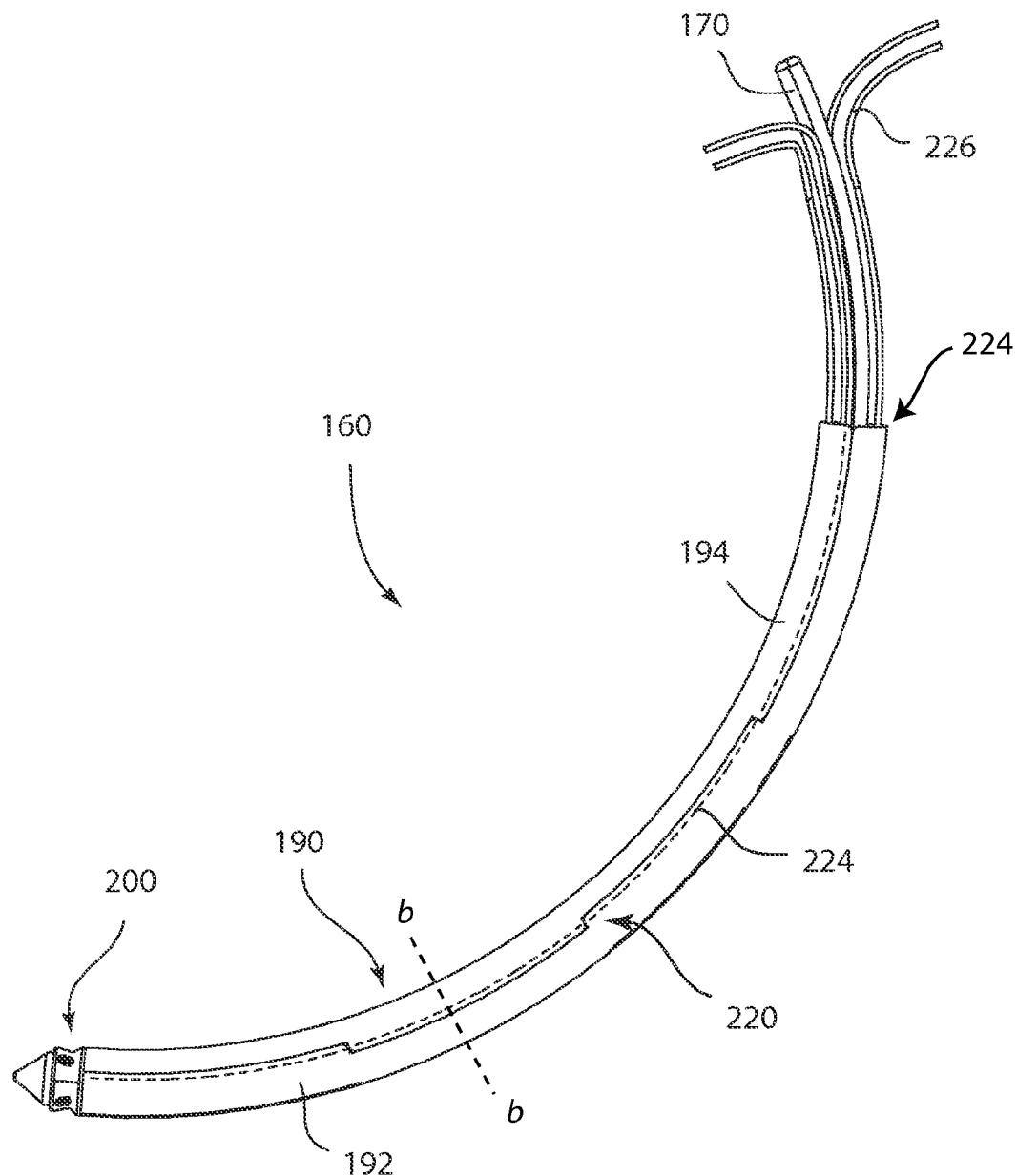
FIG. 7 is a side view of a curved tissue dilation device in a closed configuration, the device comprising a stylus, two balloons, and a plurality of curved arms radially surrounding the stylus and the balloons, wherein the arms are releasably secured to the proximal end of the stylus, and the arms are releasably secured to one another via lateral engagement features fastened by a plurality of release wires.

Referring to FIG. 7, the dilation device 160 is shown in a closed configuration, with the plurality of curved arms 190 enclosing and obscuring the balloons. A central longitudinal space is circumferentially surrounded by the arms. The plurality of curved arms 190 comprises four individual curved arms 192, 194, 196, 198. Each arm is releasably secured to the distal end of the stylus via an attachment mechanism 200. Each arm is also releasably secured to the lateral edge of the adjacent arms via lateral engagement features 220. A release wire 226 secures each arm to its adjacent neighbor by extending through an arm bore 224 which extends the length of the arms, from the proximal end to the distal end. In this embodiment, the arms are not identical to one another but each shaped so that when fitted together the arms form a closed curved cylinder about the curved stylus. For example, arms 194 and 196 may be shorter than arms 192 and 198, and have a slightly smaller radius of curvature than arms 192 and 198. The maximum outer diameter of the device 160 in the closed configuration, measured normal to the longitudinal axes of the stylus and rigid arms, such as along line b-b, may range from 5 to 15 millimeters.

Figure 8:
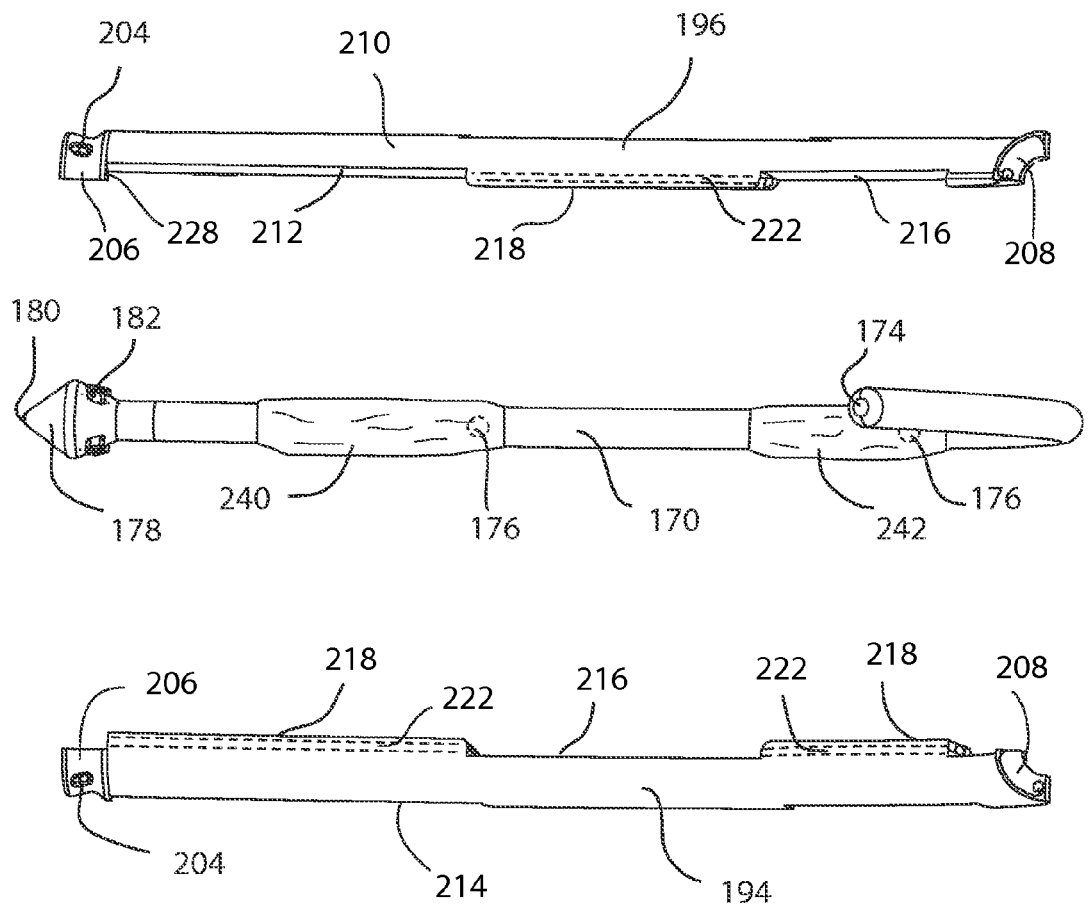
FIG. 8 is a top exploded view of the stylus and two arms of the curved tissue dilation device of FIG. 7.

Referring to FIG. 8, a perspective top down view shows the stylus 170 and two arms 194, 196. Mounted on a stylus shaft 172 are two uninflated balloons 240, 242. Each balloon extends longitudinally along a portion of the stylus, and is secured to the stylus at each balloon end. The stylus comprises an inner bore 174 which extends along a length of the stylus, and is in communication with two ports 176. The bore and ports provide a passageway for fluid to inflate the balloons 240, 242. At a distal end 177 of the stylus is a stylus tip 178 which may be formed integrally with, or separately from the stylus. The stylus tip has a point 180 which may be blunt in order to more gently push aside tissues during insertion of the stylus into body tissues and muscles. The stylus tip may have a distal conical surface which also aids in atraumatically parting tissues and muscle fibers. The maximum diameter of the stylus tip may be greater than the shaft of the stylus, as in FIG. 8; in other embodiments the maximum diameter of the stylus tip may be the same or less than the stylus shaft.

Figure 9:
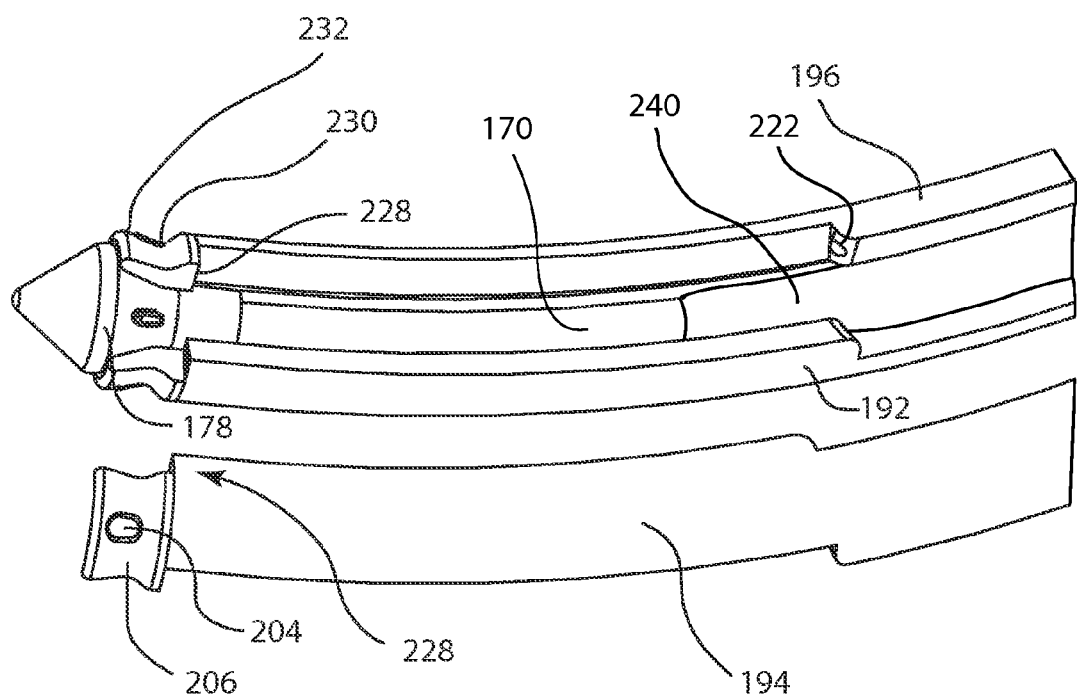
FIG. 9 is a partially exploded enlarged view of the distal end of the stylus, balloon and arms of the curved tissue dilation device of FIG. 7.

With reference to FIGS. 8 and 9, the stylus tip 178 has four discrete connecting features 182 located adjacent the distal end of the stylus. Each connecting feature 182 is a peg protruding radially from the stylus, each peg having an ovoid or egg shape with one rounded end slightly larger than the other. This shape ensures a close fitting with a complementarily shaped receiving hole 204 on the end of each arm. When the arms are fitted on the pegs as in FIG. 7, the arms are longitudinally aligned with the stylus in a predetermined longitudinal alignment in which the arms cannot move laterally relative to one another until the connection features are detached; e.g., the hole 204 is taken off the peg 182. Other connecting features are contemplated, including but not limited to pegs and corresponding holes which are round, oval, rectangular, or multi-sided; or other complementary protrusion and slot combinations. The receiving hole may be open on both ends or may be a recess or cavity with an opening on one side shaped to receive the peg. In an alternative embodiment, the pegs may be located on the arms, and the receiving hole or cavity on the stylus or stylus tip.

Each arm 192, 194, 196, 198 comprises a distal end 206, a proximal end 208, and an arm shaft 210 bounded laterally by a first lateral edge 212 and a second lateral edge 214. Each lateral edge 212, 214 comprises one or more recessed portions 216 which are distributed alternately with projecting portions 218. Thus when two arms are fitted together laterally, the projecting portions 218 on one arm fit into the recessed portions 216 on the adjacent arm. An arm bore section 222 extends longitudinally along each lateral edge, through the entire length of each projecting portion 218. When two arms are fitted together laterally, one continuous arm bore 224 is formed from the alternating arm bore sections 222 which are now axially aligned with one another. The release wire 226, seen in FIG. 7, can be inserted along the length of each arm bore 224 to effectively pin or lace the arms securely together. After advancement of the closed device 160 into the tissues and prior to expansion of the device, the release wire(s) 226 may be withdrawn so that the arms may move apart from one another with the expansion force. Other lateral engagement features are contemplated, including but not limited to tongue-in-groove features, corresponding tab and slot features, or press-fit features. Such features may be disengaged by removal of a pin, suture or wire such as release wire 226, or may have a friction fit in which the features are detached from one another by sufficient expansive force provided by expansion of the dilating member.

Referring to FIGS. 8 and 9, details of the arm and stylus distal ends are shown. The distal end 206 of each arm 192, 194, 196, 198 may include an offset 228, in which the distal end is offset from the shaft 210. The offset 228 allows the arms to fit more precisely together when the device 160 is in the closed configuration, and also provides a stop surface for a distal end of the release wire 226. The distal end 206 may also include a waist 230 and an adjacent flared portion 232. Together, the waist 230 and flared portion 232 form a concavely curved area at the distal end of the arm, which may aid in holding back or retaining tissues dissected and pushed aside by the stylus tip 178 during advancement of the device into muscle and other tissues, and may aid in holding back or retaining tissues moved apart during dilation or expansion of the device 160. The flared portions 232 may act as a retainer to prevent tissues from slipping back over the distal ends of the arms once the tissues have been dissected apart from one another. The inner surface of the flared portion 232 may also be shaped to complementarily mate with the outer surface of the stylus tip 178, a portion of which may flare outward.

An alternative embodiment of the dilation device may include a stylus and arms with corresponding connecting features such as the peg/hole system set forth above, but no lateral engagement features on the arms. Another embodiment may include lateral engagement features on two or more arms, but no corresponding connecting features between the arms and the stylus. Yet another embodiment may comprise neither distal connection features nor lateral engagement features. It is appreciated that additional embodiments may include any combination of the features described herein.

Dilation device 160 may further comprise an inner mesh positioned longitudinally between the balloons and the plurality of arms in the same manner as inner mesh 130 set forth in the previous embodiment. The device may also further comprise an outer sleeve securely attached to the arms and positioned longitudinally either inside or outside the plurality of arms, in the same manner as outer sleeve 140 set forth in the previous embodiment. The mesh and sleeve may comprise the same materials as set forth previously for inner mesh 130.

Figure 10:
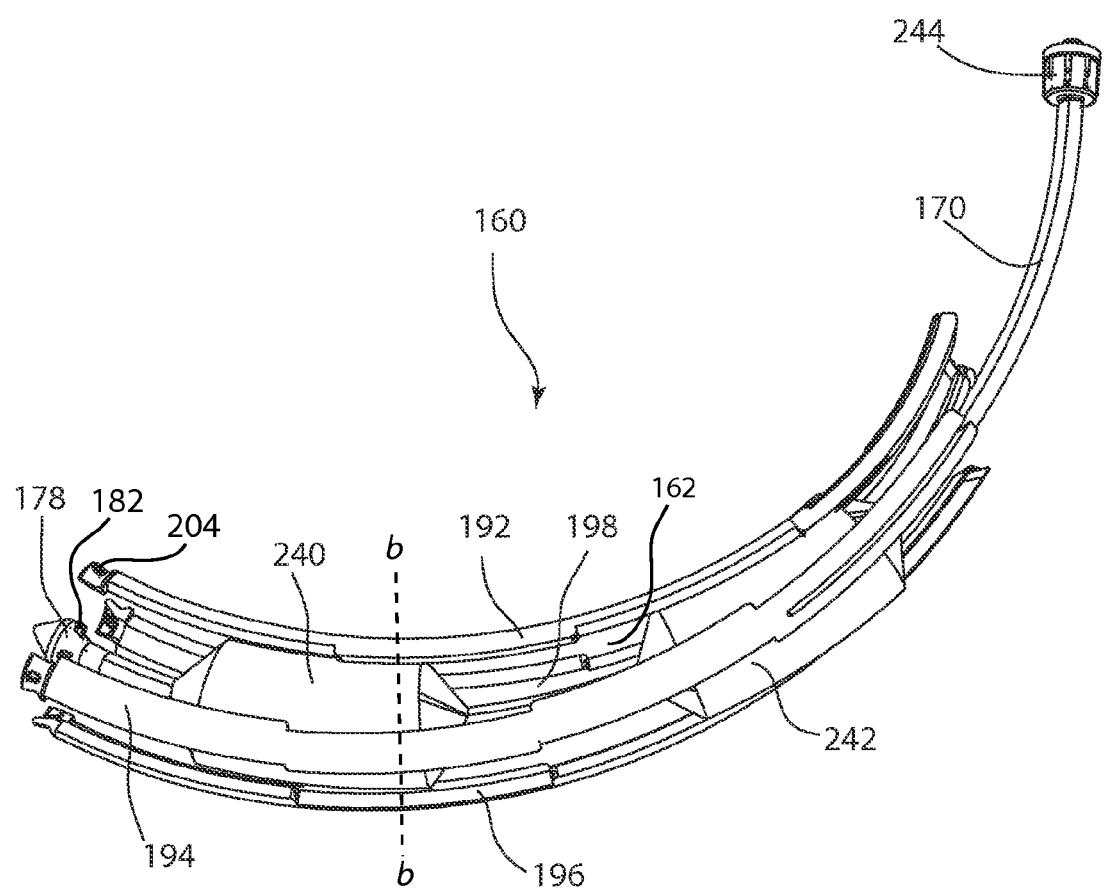
FIG. 10 is a perspective view of the tissue dilation device of FIG. 7 in an expanded configuration, with a luer attached to the proximal end of the stylus.

Referring to FIG. 10, dilation device 160 may be expanded by introduction of a fluid into the stylus 170. Prior to expansion, any release wires may be withdrawn from the arm bores. A luer 244 at the distal end of the stylus provides means for introduction of the fluid, such as saline, into the stylus bore. The fluid is forced distally along the stylus and escapes through ports 176, inflating balloons 242 and 240. The proximally located balloon 242 may inflate in advance of the distally located balloon 240, and this may push the arms slightly distally, then radially outward as both balloons inflate. As the arms 192, 194, 196, 198 move radially outward, the arm connection features 204 are disengaged from the stylus connection features 182 by the expansion force provided by the inflation of the balloons. Similarly, the lateral engagement features 216, 218 disengage and the arms may move radial-laterally apart with the expansion of the balloons. After inflation of the balloon has provided sufficient expansion of the device to dilate the surrounding tissue a desired amount, the introduction of fluid may be ceased, and the stylus 170 with the attached balloons 240, 242 may be removed, leaving a passageway through the surrounding tissue. In the open configuration, the maximum outer diameter of the device 160, measured normal to the longitudinal axis of the stylus and rigid arms, such as again along line b-b, may range from 25 to 40 millimeters. The expansion ratio of device 160 may range from 2.5 to 8.0. In some embodiments, the expansion ratio may range from 3.0 to 7.5; in other embodiments, the expansion ratio may range from 4.0 to 7.0; while in other embodiments, the expansion ratio may range from 5 to 6.5. In a preferred embodiment, the expansion ratio may be at least 6.0.

Figure 11:
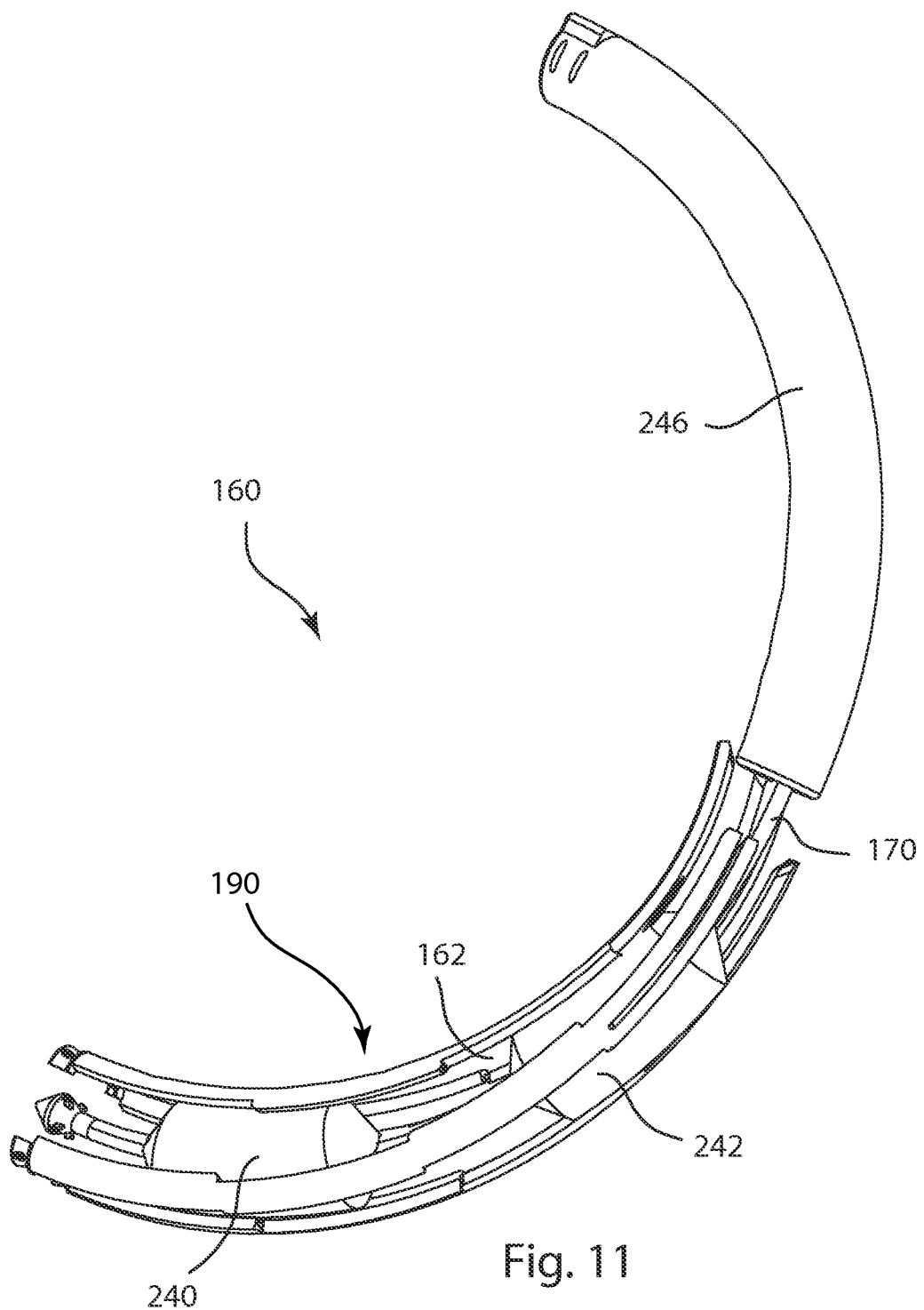
FIG. 11 is a perspective view of the tissue dilation device of FIG. 7 in an expanded configuration, with a cannula partially inserted into the device.

Referring to FIG. 11, a cannula may be inserted between the stylus 170 and the curved arms 190 to keep the device in the open configuration and prevent migration of tissues into the central longitudinal space 162. A cannula such as arcuate cannula 246 may be inserted along a curved path over the stylus 170 before withdrawal of the stylus and balloons from the device 160, as shown in FIG. 11. Alternately, the cannula may be inserted along the insides of the arms after withdrawal of the stylus and balloons. It is appreciated that the cannula is not passed along the outside of the device, which could crush or injure of the adjacent tissues. Instead, the cannula is advanced along the inner sides of the expanded arms, and within the optional outer sleeve. Following insertion of the cannula and withdrawal of the stylus, balloons, and optional inner mesh, instruments, implants and other materials may be passed through the cannula to perform surgical procedures at the end of the passageway formed by the expanded device. The cannula may be docked to a skeletal structure such as a vertebra, and/or to a surgical table support system, to provide stability during surgical procedures.

Figure 12:
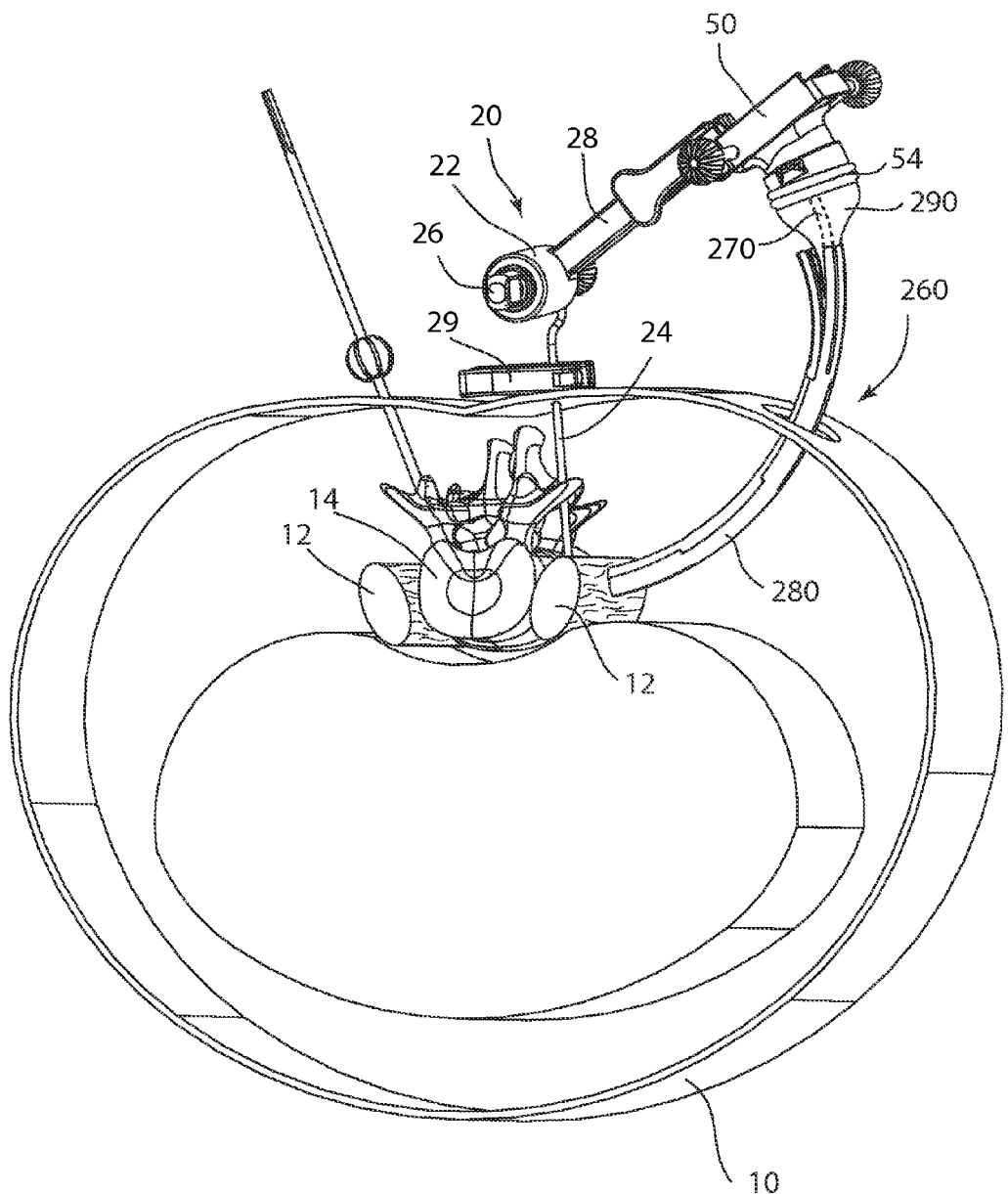
FIG. 12 is a perspective view of a stylized cross-section of a human body, with a curved tissue dilation device in a closed configuration inserted into a psoas muscle, and connected to a targeting system positioned to target a predetermined location along the spine.
Figure 13:
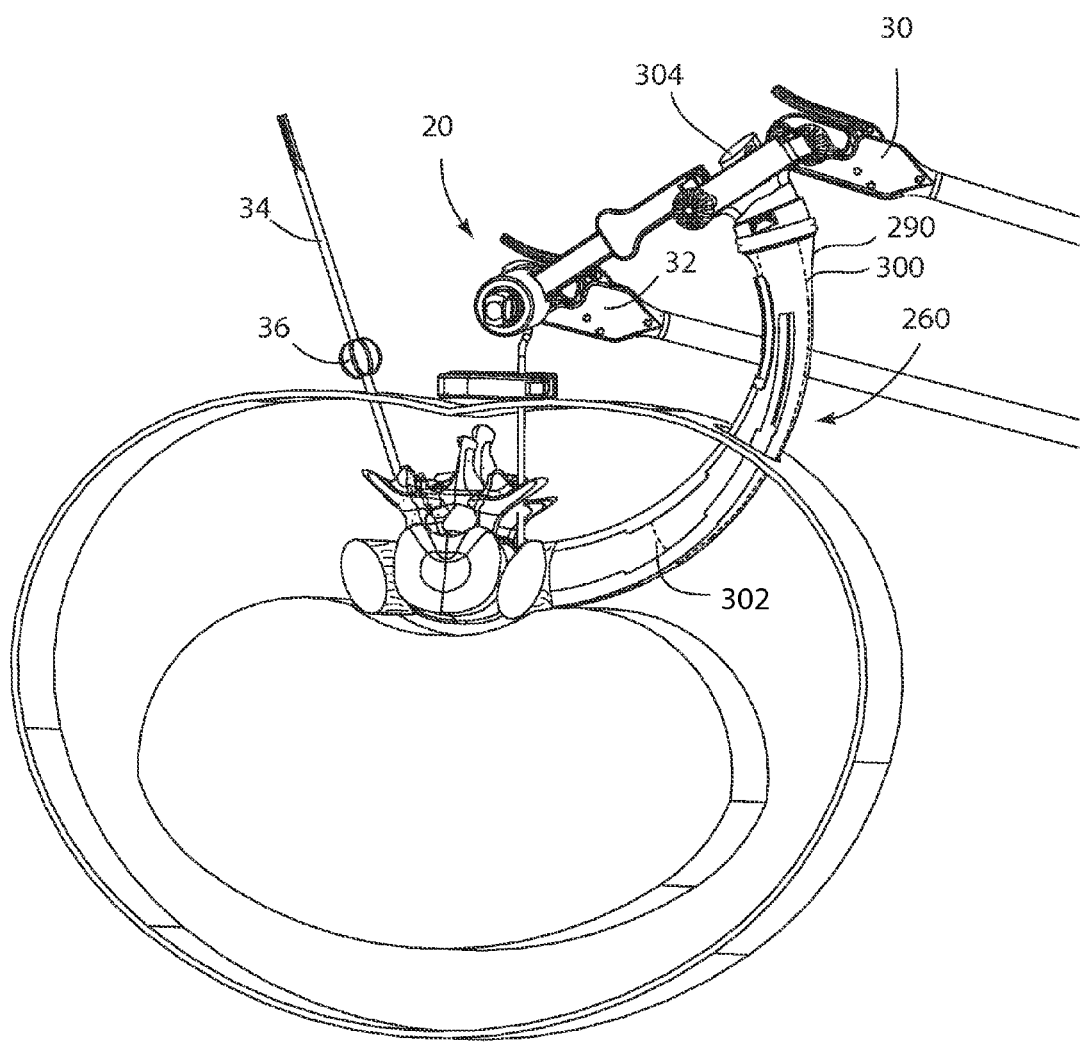
FIG. 13 is a perspective view of the body, curved tissue dilation device and targeting system of FIG. 12, with the dilation device in an open configuration and the dilation device and targeting system secured to table mounted clamps, and with a cannula partially inserted into the dilation device.
Figure 14:
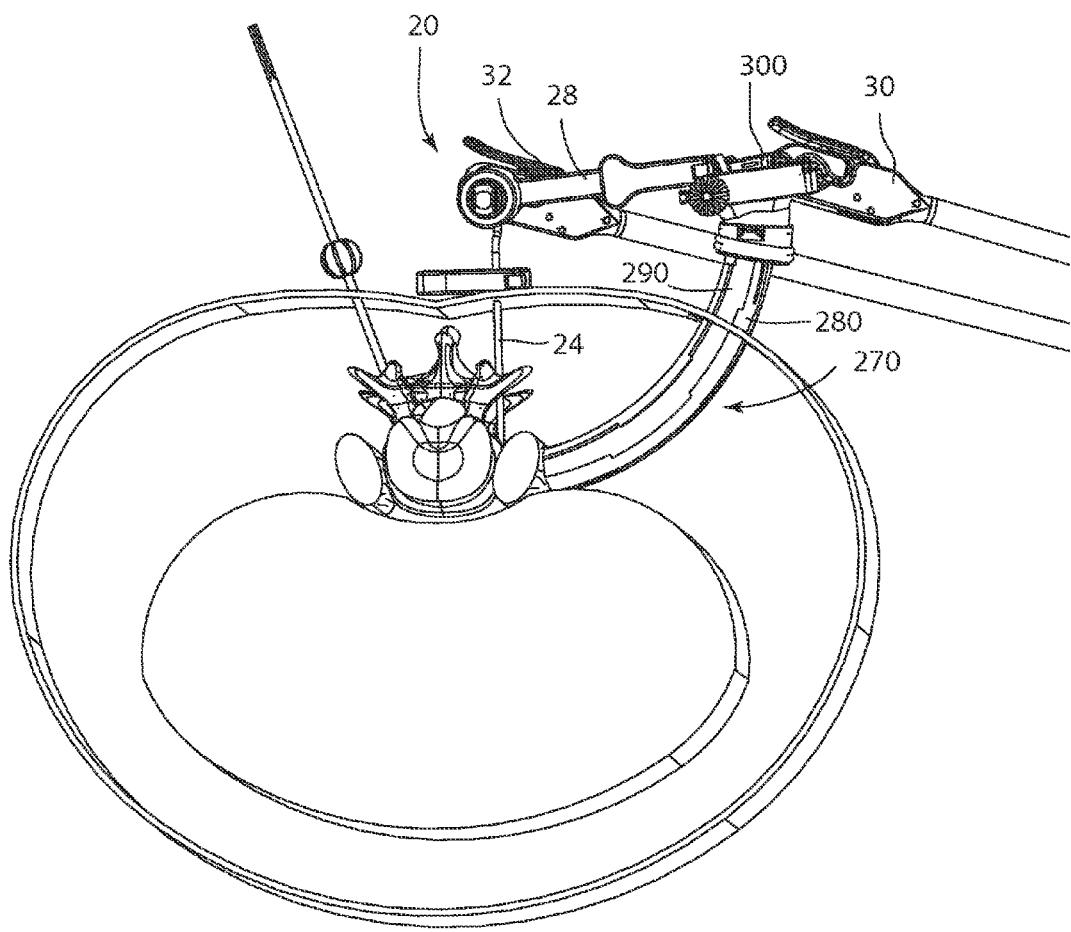
FIG. 14 is a perspective view of the body, curved tissue dilation device and targeting system of FIG. 12, with the cannula fully inserted into the dilation device.

FIGS. 12-14 illustrate a dilation device inserted through an opening in the skin and through a psoas muscle to create a passageway to an intervertebral location, from a posterolateral approach. The device 260 is transformable from a closed configuration in which each arm is in contacting longitudinal alignment with two other of the arms along their lateral edges, and an open configuration in which the arms are radially displaced from the stylus and laterally displaced from one another. Dilation device 260 comprises a stylus 270, a plurality of arms 280, a tubular sleeve 290, and dilating member which is a cannula 300. In embodiments such as this wherein the dilating member is not a balloon, the entire stylus including the distal tip may be cannulated to allow for flushing of the site, and/or passage of a k-wire.

Referring to FIG. 12, dilation device 260 is shown in the closed configuration, inserted through an incision in the skin 10 and through the psoas muscle 12. The sleeve 290 is secured to the inner surfaces of the arms 280, and at its proximal end, to a collet portion 54 of hub 50. The stylus 270 is also releasably clamped to the hub 50. The hub 50 is secured to a targeting system 20 which is fully described in U.S. patent application Ser. No. 12/357,695, filed on Jan. 22, 2009 and entitled Spinal Access Systems and Methods, the entirety of which is herein incorporated by reference. It is appreciated that hub 50 and/or the targeting system may be secured to other support systems such as surgical table support systems known in the art, to provide stability during device insertion and dilation, and during other surgical procedures. Targeting system 20 comprises a housing 22, a targeting post 24, a micrometer 26 and a swing arm 28. The targeting post 24 may be advanced through the skin and fascia to a desired depth and location adjacent the spine 14, and a targeting depth stop 29 may regulate the depth of the targeting post. The micrometer 26 may be used to finely adjust the position of the targeting post. The offset arm or swing arm 24 connects the housing 22 to the hub 50. The swing arm 24 may be raised or lowered, rotating about the axis of the housing 22, to raise or lower the hub 50 and the associated dilation device 270. In FIG. 12, the swing arm 24 has been lowered sufficiently to guide the device 260 along an arcuate curved path into the psoas muscle.

Toward the proximal end of the plurality of arms 280, each arm comprises a longitudinal slot which extends from the proximal end distally along a portion of the arm. This slot may provide a slight amount of flexibility to the arm proximal ends as the cannula 300 is inserted to initiate transformation of the device 260 from the closed to the open configuration. The slots may also be guides, cooperating with pins or protrusions on the cannula or on a separate guiding ring to guide insertion of the cannula into the device.

Referring to FIG. 13, the dilation device 260 is shown in the open configuration. The hub 50 and the housing 22 are connected to polyaxially adjustable table mounted clamps 30, 32. A post 34 is anchored in a pedicle, and a slidable clamping sphere 36 is positioned on the post. Optionally, the targeting system may be clamped to the post 34, in place of or in addition to the table mount clamp. The stylus 270 has been withdrawn from the dilation device 260, and a distal end 302 of the cannula 300 has been partially advanced into the system, inside the plurality of arms 280 and the sleeve 290. A proximal end 304 of the cannula is docked to the hub 50. The cannula 300 has a larger diameter than the plurality of arms 280 in the closed configuration. As the cannula 300 is advanced along a curved path inside the space within the closed arms, the arms 280 are forced radial-laterally apart, opening up the attached tubular sleeve 290, and creating a passageway through the tissues and psoas muscle.

Referring to FIG. 14, the dilation device 260 is shown in the open configuration, and the distal end of the cannula 300 has been fully advanced along the plurality of arms and through the psoas muscle. The swing arm 28 has been partially rotated about the axis of the housing 22, thus lowering the hub and the docked cannula to fully advance the cannula along the curved path, and decreasing the angle between the swing arm 28 and the targeting post 24. The clamp arms 30, 32 have been adjusted to stabilized the device at the fully advanced position. Other instruments, implants, and materials may be passed through the passageway formed by the cannula.

Figure 15:
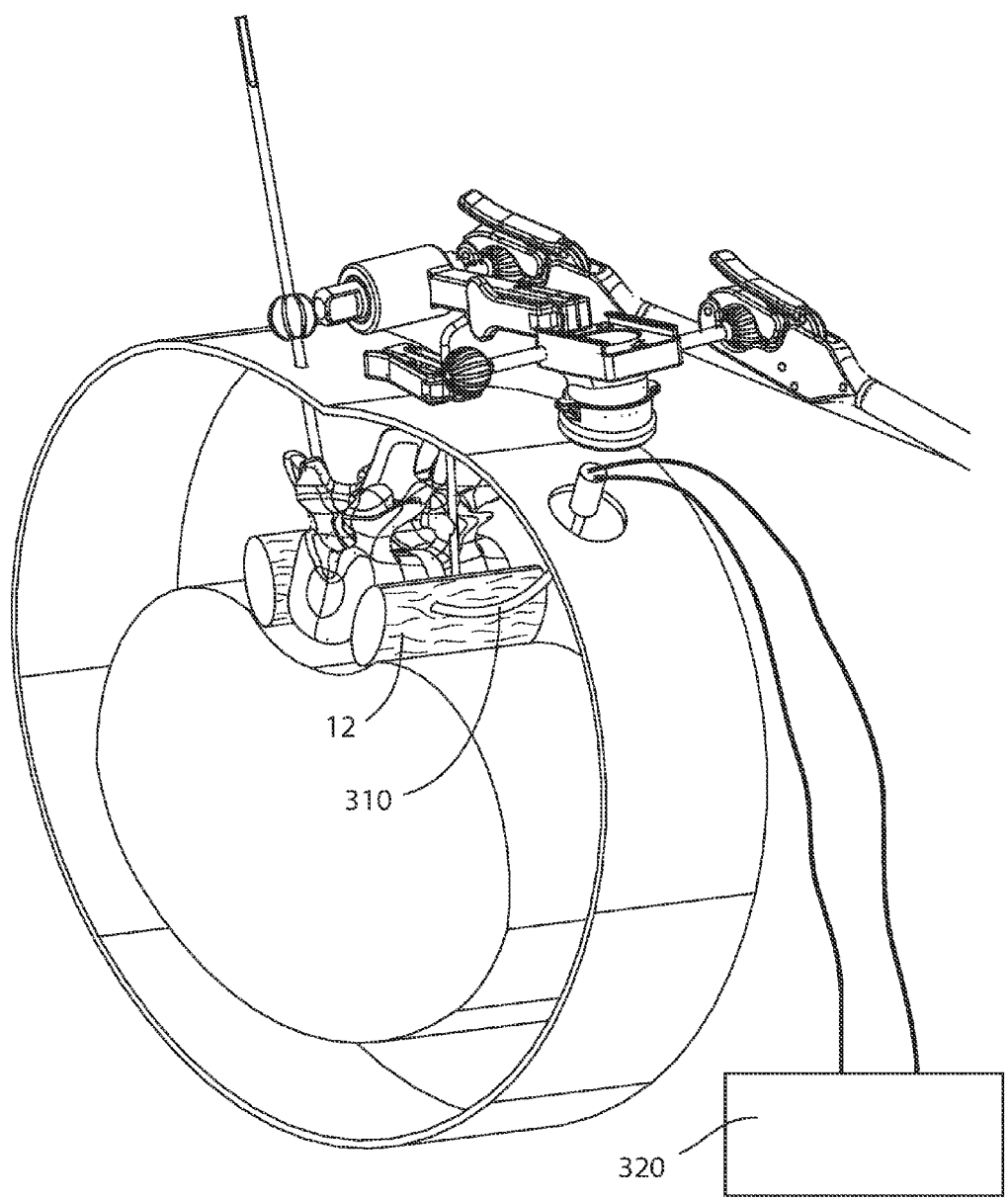
FIG. 15 is a perspective view of the body and targeting system of FIG. 12, with an electromyography electrode inserted into the psoas muscle and connected to a neural monitoring system.

FIG. 15 illustrates an electromyography (EMG) electrode 310 inserted into the psoas muscle. The electrode 310 is connected to a neural monitoring system 320 which can detect the presence of nervous tissue. Prior to insertion of a dilation device such as devices 60, 160, or 260, the electrode 310 may be advanced into the muscle or tissue to be dilated, and energized, or activated, to detect the presence of a nerve. The electrode may then be deactivated and/or removed, and the dilation device inserted into the muscle or tissue. If a nerve is sensed along a particular path or trajectory, the dilation device may be inserted along a different path or trajectory, in order to avoid the nerve. The electrode and neural monitoring system may be used prior to insertion of the dilation device, after insertion of the device but prior to dilation, and following dilation, to detect and avoid nervous tissue. The electrode may also be activated intermittently during advancement of the dilation device. In alternative embodiments of the device, the rigid arms, if metallic, may be used as the electrode. As well, transmissive tape and/or paint can be applied to the surface of the arms to create a surface capable of transmitting voltage.

Figure 16:
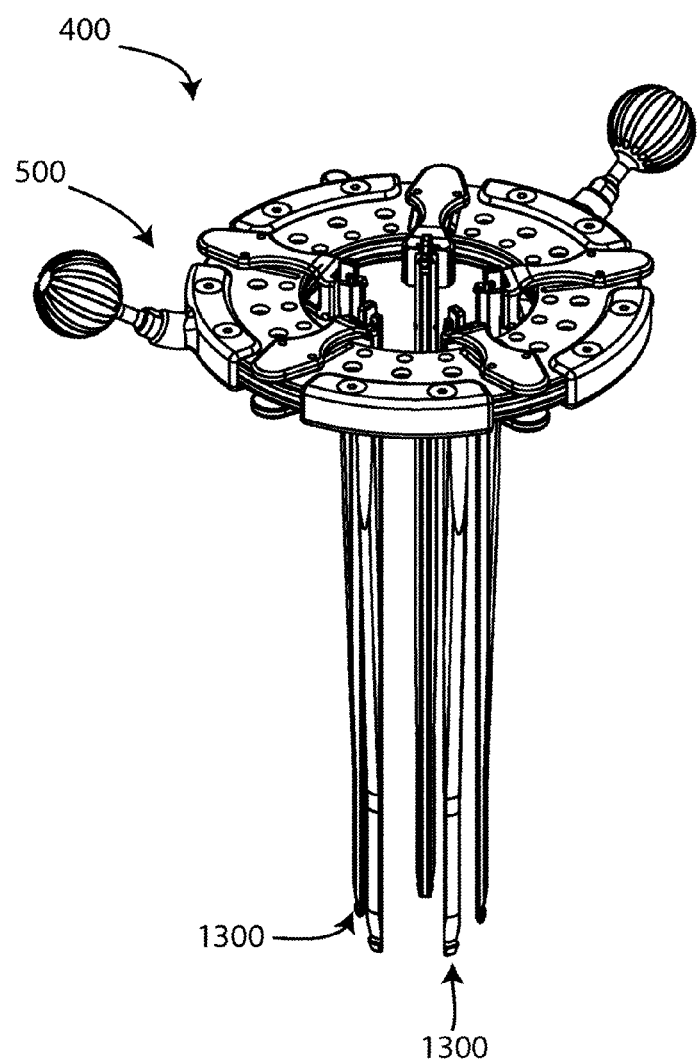
FIG. 16 is a perspective view of another tissue dilation device in an open configuration.

FIGS. 16-27 illustrate another dilation device 400. Dilation device 400 may also be described as a dilation assembly since it includes several component parts in an operative arrangement. FIG. 16 shows dilation device 400 in an open configuration. Dilation device 400 includes a hub assembly 500 and a plurality of arm assemblies 1300. Dilation device 400 is configured to accept up to five arm assemblies 1300, although alternate embodiments may include two or more arm assemblies. The arm assemblies 1300 are carried by the hub assembly 500. In this embodiment, the arm assemblies 1300 are evenly spaced in a circular or pentagonal pattern around the hub assembly 500, although non-circular or non-symmetric arrangements are contemplated. The pattern of arm assemblies 1300 synchronously expands and contracts relative to the hub assembly 500. In other words, each arm assembly 1300 is radially movable relative to a center of the pattern. The center of a pattern is a point which is, in some sense, in the middle of the pattern. Other embodiments may provide for independent adjustments in different directions, such as independent adjustment in the anterior-posterior, medial-lateral, and/or cephalad-caudal directions.

A portion of the dilation device 400 may be introduced into a muscle, other tissue, or natural passageway in a closed configuration (illustrated in FIG. 56), in which the arms may be in contacting longitudinal alignment. The dilation device 400 may then be expanded from the closed configuration to the open configuration. If introduced into a muscle, the expansion of dilation device 400 bluntly dissects and separates the muscle fibers. The expansion of dilation device 400 forms an open passage through the muscle, tissue, or natural passageway, through which instruments, implants and other materials may be passed to perform one or more surgical procedures.

Figure 17:
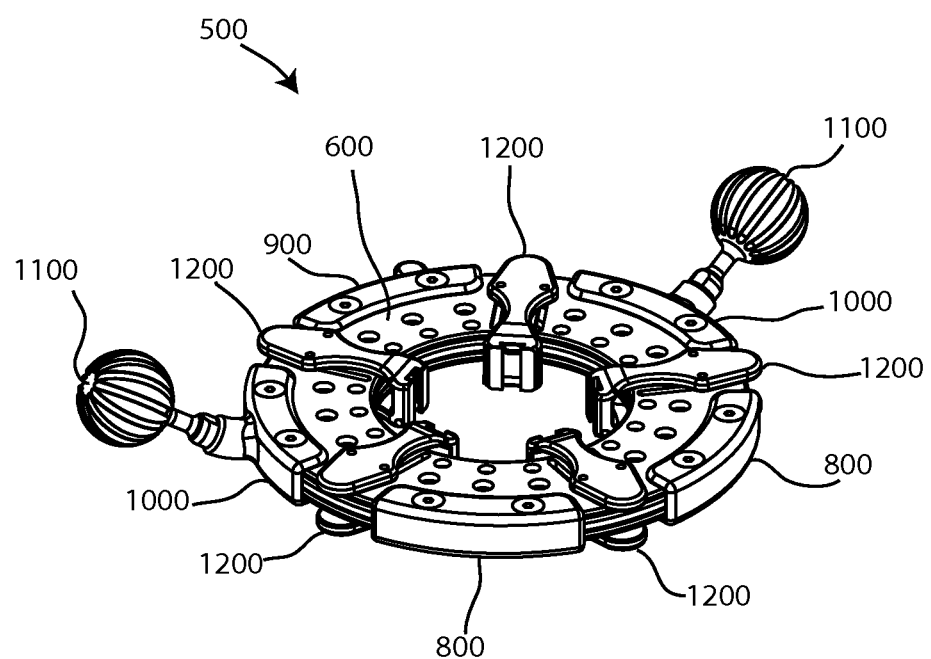
FIG. 17 is a perspective view of a hub assembly of the tissue dilation device of FIG. 16.
Figure 18:
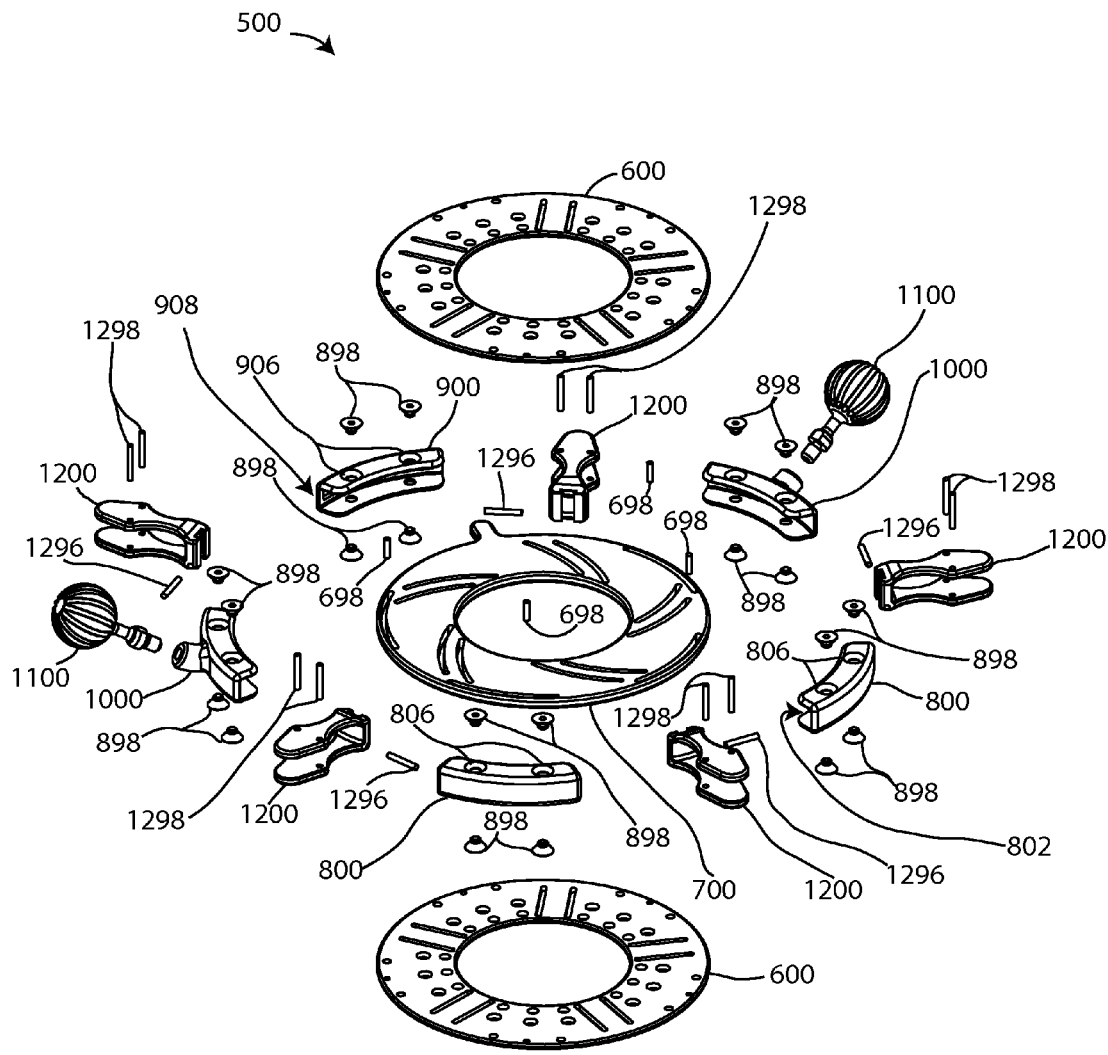
FIG. 18 is an exploded perspective view of the hub assembly of FIG. 17.

FIGS. 17-23C illustrate hub assembly 500 in more detail. With reference to FIGS. 17-18, hub assembly 500 includes stationary disk 600, drive disk 700, basic disk clamp 800, slotted disk clamp 900, socket disk clamp 1000, clamp connection 1100, arm clamp 1200, and associated fasteners such as dowel pins and screws. Drive disk 700 is sandwiched between two stationary disks 600, and the three disks are secured together by disk clamps 800, 900, and 1000 which connect around the outer diameter of the disks. The stationary disks 600 and disk clamps 800, 900, and 1000 form a stationary frame within which drive disk 700 is freely rotatable. Arm clamps 1200 connect around the inside diameter of the stacked disks in a circular pattern, and are freely linearly translatable relative to the stationary frame along a radius of the circular pattern. The rotation of drive disk 700 and the translation of arm clamps 1200 are linked so that a force input causing translation of arm clamps 1200 will also cause drive disk 700 rotation, and vice versa. In this way, hub assembly 500 provides synchronized radial expansion and contraction of the pattern of arm clamps relative to the disks 600, 700. At least some components of hub assembly 500 may be partially or completely radiolucent.

Figure 19:
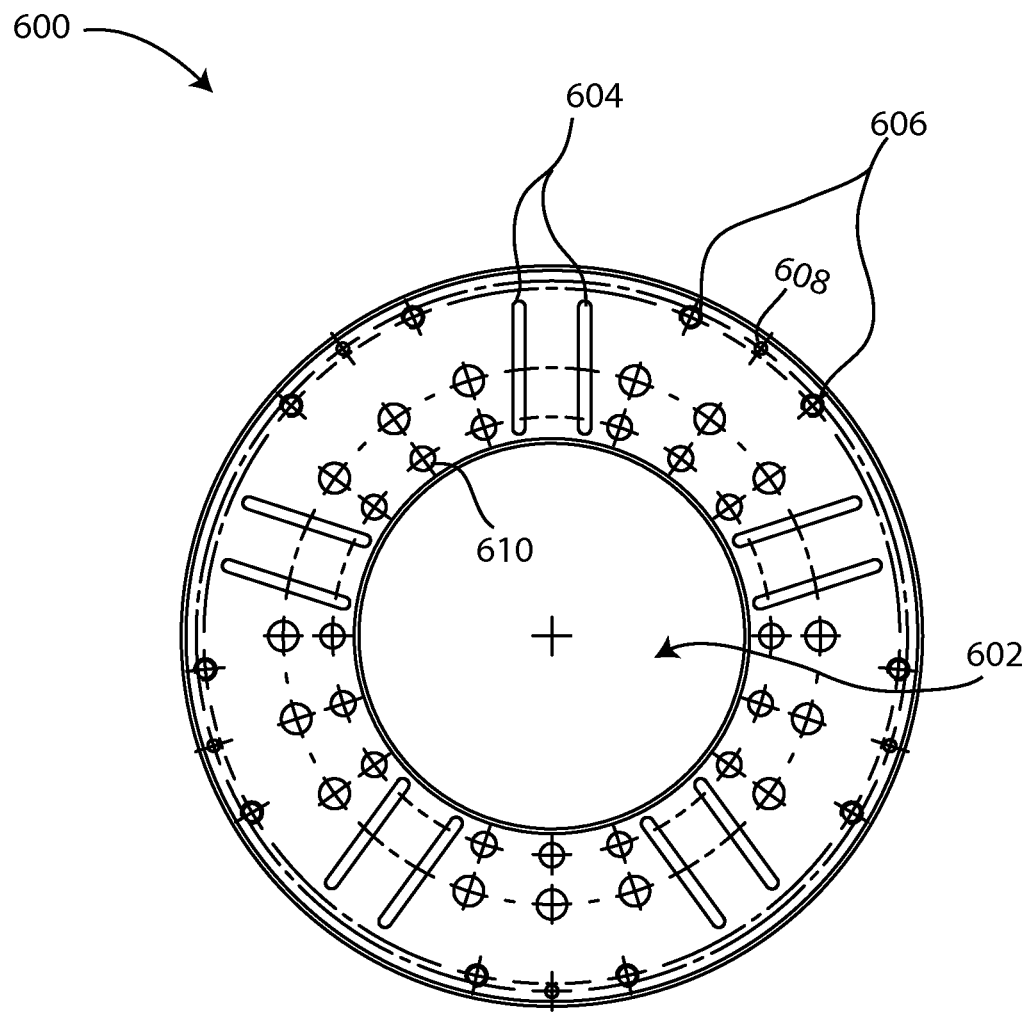
FIG. 19 is a top view of a stationary disk of the hub assembly of FIG. 17.

Referring to FIGS. 18-19, stationary disk 600 is shaped as a ring or annulus with a central aperture 602. Stationary disk 600 includes five pairs of linear, radially-extending slots 604 evenly spaced around the disk. Stationary disk 600 also includes five pairs of holes 606 evenly spaced around the disk near the outer diameter. Smaller holes 608 may also be present, one between each pair of holes 606. One or more additional holes 610 may be present, for example, to reduce weight or provide easy access for cleaning.

Figure 20:
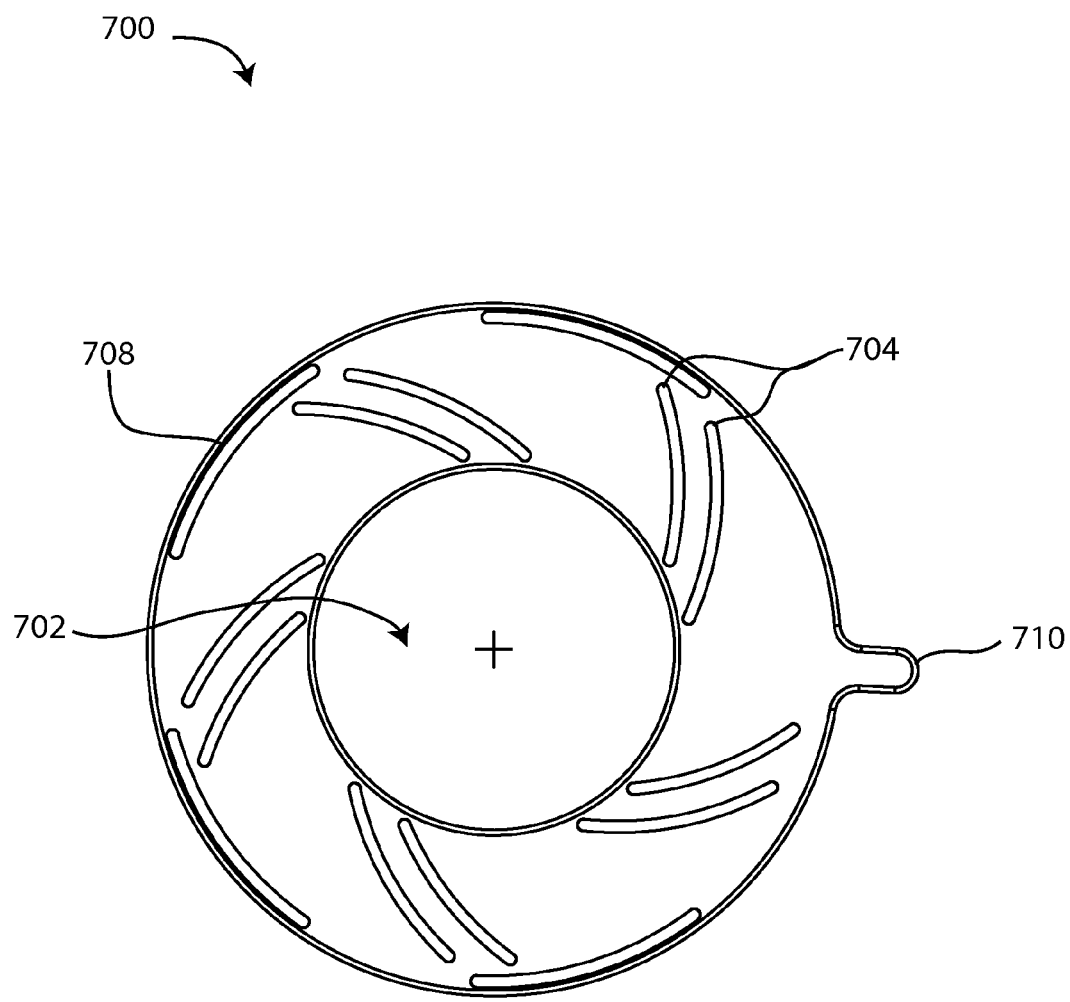
FIG. 20 is a top view of a drive disk of the hub assembly of FIG. 17.

Referring to FIGS. 18 and 20, drive disk 700 is shaped as a ring or annulus with a central aperture 702. Drive disk 700 includes five pairs of arcuate, obliquely-extending slots 704 evenly spaced around the disk. Drive disk 700 also has four arcuate perimeter slots 708 positioned around the disk in four of five evenly spaced positions. Drive disk 700 includes a tab 710 which protrudes from the outer diameter of the disk.

Referring to FIG. 18, a basic disk clamp 800, or bracket, may have an arc shape which is complementary to the outer diameter of stationary disk 600, drive disk 700, or both. A concave side of disk clamp 800 includes a channel 802 or groove which is sized to receive the combined thickness of two stationary disks 600 and one drive disk 700 with clearance. Disk clamp 800 also includes a pair of through holes 806 which are sized and positioned to correspond to holes 606 of stationary disk 600, and also sized and configured to complement fastener 898. For example, if fastener 898 is a screw, then holes 806 may be threaded with a corresponding internal thread form. Disk clamp 800 may accept up to four fasteners 898.

With continued reference to FIG. 18, a slotted disk clamp 900, or bracket, may share some or all of the characteristics set forth above for disk clamp 800, and is further characterized by a through slot 908, as may be seen best in FIG. 30B. Tab 710 of drive disk 700 protrudes through slot 908 when hub assembly 500 is fully assembled, and provides a force input location to rotate drive disk 700.

Figure 22:
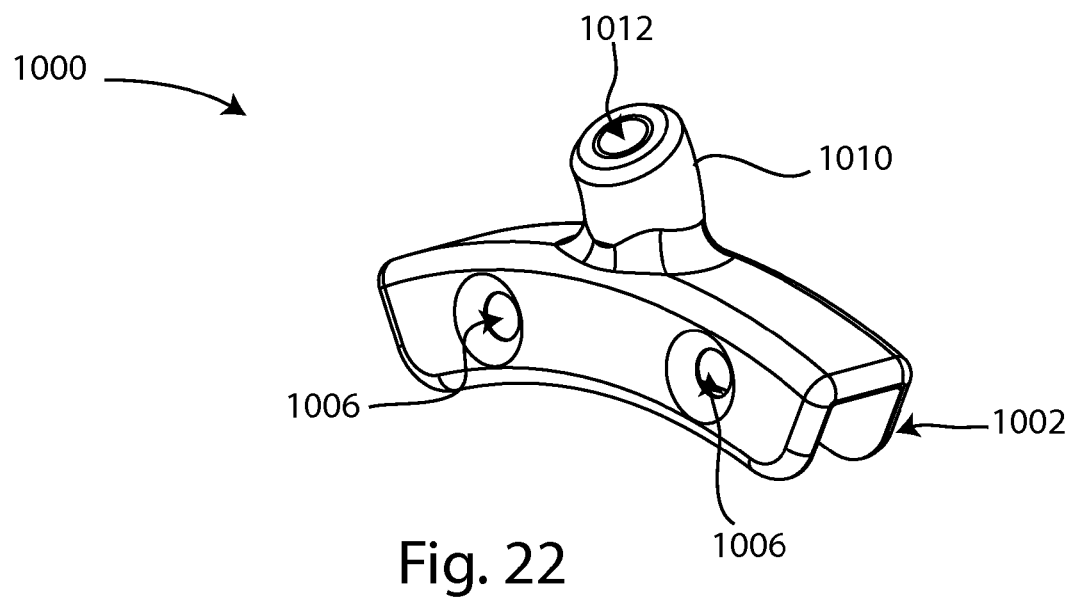
FIG. 22 is a perspective view of a disk clamp of the hub assembly of FIG. 17.

Referring now to FIGS. 18 and 22, a socket disk clamp 1000, or bracket, may share some or all of the characteristics set forth above for disk clamp 800, such as concave channel 1002 or holes 1006. Additionally, disk clamp 1000 includes a central protrusion 1010 extending from a convex side of the bracket. A socket 1012 extends at least partially into protrusion 1010.

Figure 21:
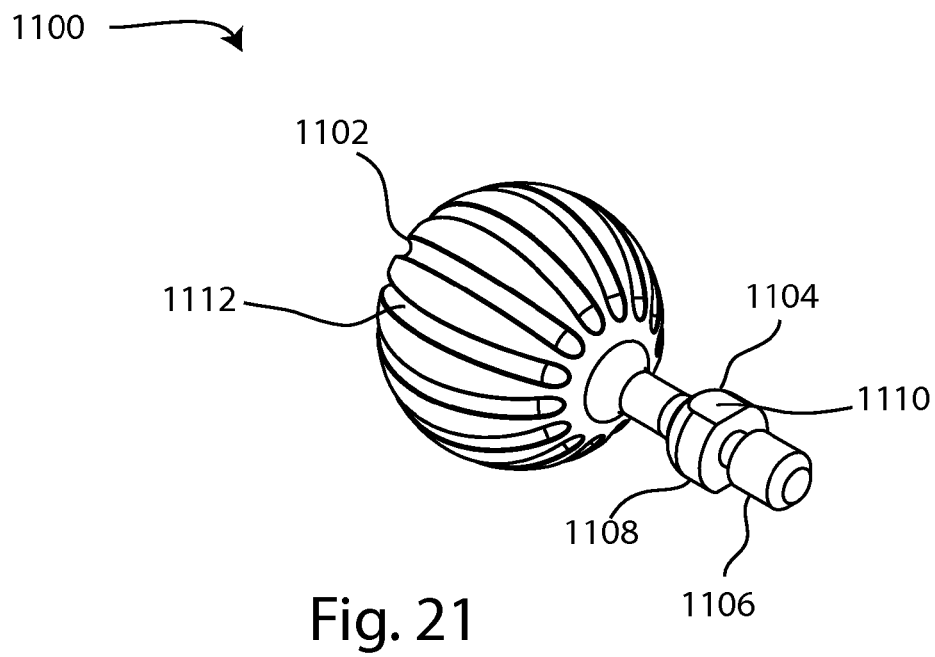
FIG. 21 is a perspective view of a clamp connection of the hub assembly of FIG. 17.

With reference to FIGS. 18 and 21, clamp connection 1100 is most notably characterized by a spherical ball 1102 from which a shaft 1104 protrudes. Ball 1102 may be smooth or textured. For example, FIG. 21 illustrates a textured ball 1102 which has a regular pattern of grooves 1112. Other textures are contemplated, such as knurling, dimples, or a sandblasted finish. Shaft 1104 may optionally have threads 1106 and a drive feature 1108 such as a pair of opposed flats 1110. If threads are present, clamp connection 1100 may thread into a correspondingly threaded socket 1012 in disk clamp 1000. Alternatively, clamp connection 1100 may be pinned, press fit, welded, or joined to disk clamp 1000 by some other means. Clamp connection 1100 may also be integrally formed with disk clamp 1000 in some embodiments.

Referring to FIGS. 18 and 23A-C, arm clamp 1200, or bracket, is illustrated with an hourglass profile in the top view, as may be seen in FIGS. 19 and 23A. Other profiles are contemplated for their function or decorative appeal. Also visible in FIG. 23A, dovetail slot 1206 is formed in, and extends completely across, one enlarged end of the hourglass shape. A pocket 1208 may be formed in the bottom of dovetail slot 1206, as may be seen in FIG. 23C. Arm clamp 1200 also includes a pair of through holes 1204 which are sized and positioned to correspond to slots 604 of stationary disk 600 and slots 704 of drive disk 700. Holes 1204 are also sized and configured to complement fastener 1298. For example, if fastener 1298 is a dowel pin, then at least some of the holes 1204 may be dimensioned and toleranced to receive fastener 1298 with a press fit or interference fit. In a side view, arm clamp 1200 includes a channel 1202 or groove which is sized to receive the combined thickness of two stationary disks 600 and one drive disk 700 with clearance. Channel 1202 extends across the narrow portion of the hourglass shape in the illustrated embodiment, with the bottom of the channel 1202 adjacent to the dovetail slot 1206. Arm clamp 1200 also includes a through hole 1210 which intersects the dovetail slot 1206 opposite the pocket 1208. Hole 1210 may be sized and configured to complement fastener 1296.

Hub assembly 500 may be assembled by sandwiching a drive disk 700 between two stationary disks 600. The three disks may optionally be secured together by passing a fastener 698 through each hole 608 in one of the stationary disks 600, a corresponding slot 708 in the drive disk 700, and a corresponding hole 608 in the second stationary disk 600. Alternately, or in combination, the three disks may be secured together with disk clamps 800, 900, 1000 and fasteners 898. In this situation, disk clamp 900 may be positioned over the outer perimeter of the three disks so that tab 710 of the drive disk 700 protrudes through slot 908 and holes 906 align with holes 606 of the stationary disks 600. Disk clamp 900, stationary disks 600, and drive disk 700 may be secured together by inserting four fasteners 698 through holes 906, 606. Two disk clamps 1000 may be similarly positioned, one on either side of disk clamp 900. Four fasteners may be inserted through holes 1006, 606 to secure disk clamps 1000, stationary disks 600, and drive disk 700 together. Two disk clamps 800 may be similarly secured in the remaining positions with a total of eight fasteners 698 inserted through holes 806, 606. Each arm clamp 1200 may be prepared by inserting a fastener 1296 through hole 1210, and then attached to the stationary disks 600 and drive disk 700 by positioning the arm clamp 1200 over the edges of the central apertures 602, 702 so that holes 1204 align with corresponding slots 604 and 704, and inserting two fasteners 1298 through holes 1204 and slots

604, 704. In the illustrated embodiment, all of the arm clamps 1200 are oriented with their fasteners 1296 near the same stationary disk 600, as may be appreciated in FIG. 17.

Referring to FIGS. 24A-27, an arm assembly 1300 may include an arm 1400, an arm lock 1500, and a fastener 1498.

FIGS. 24A-26 illustrate an arm 1400, or blade, with an elongated shaft 1402 extending between a base 1404 and a tip 1406. One side of arm 1400 has a full length groove 1408 or depression. The base 1404 includes a dovetail protrusion 1410 on a side opposite the groove 1408. The dovetail protrusion 1410 is sized and shaped to complement dovetail slot 1206 of arm clamp 1200. A slot 1412 extends completely across the end of base 1404 between the groove 1408 and dovetail protrusion 1410. A hole 1414 is formed in the bottom of slot 1412, parallel to the dovetail protrusion 1410. Hole 1414 is intersected near its bottom by a through hole 1416. Hole 1416 is sized and configured to complement fastener 1498. The tip 1406 includes a waist 1418 and an adjacent flared portion 1420. Together, the waist 1418 and flared portion 1420 form a concavely curved area on the tip 1406, which may aid in holding back or retaining tissues dissected and pushed aside by the dilation device 400. The tip 1406 may include a docking feature (not shown), such as a spike or a pin hole, to permit the arm 1400 to be stabilized against a structure surrounding the operative site.

The arms 1400 may be at least partially radiolucent, so as not to compromise visualization of procedures during use of the device with fluoroscopy. Alternatively, the arms 1400 may be at least partially radiopaque, to assist with positioning and location of the system under fluoroscopy. The arms 1400 may be rigid, semi-rigid, or flexible. The arms 1400 may comprise metals such as aluminum, stainless steel, titanium, and other biocompatible metals. The arms 1400 may also comprise high density plastics such as Delrin, Radel, Udel, poly ether ether ketone (PEEK), polycarbonate, and acrylonitrile butadiene styrene (ABS), among others. Barium sulphate may be added to constituent plastic materials to provide increased radiopacity. The arms may conduct light or function as a light guide or light conductor.

Figure 24A:
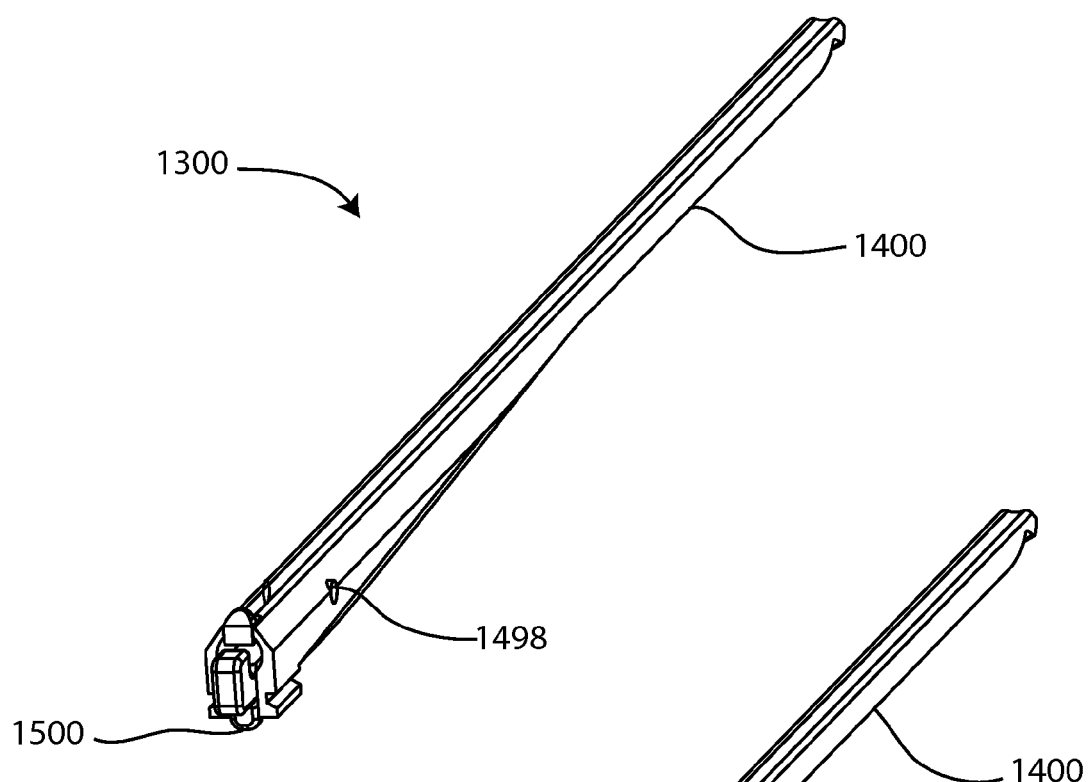
FIG. 24A is a perspective view of an arm assembly of the tissue dilation device of FIG. 16.
Figure 24B:
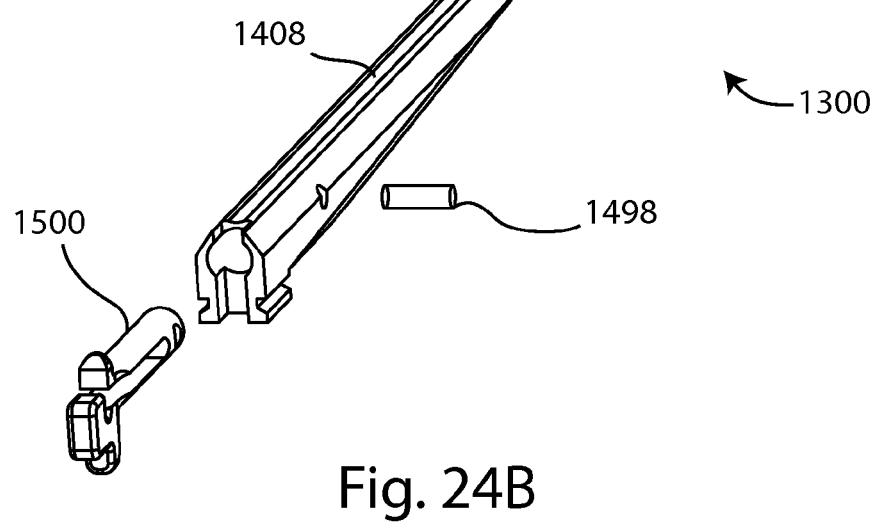
FIG. 24B is an exploded perspective view of the arm assembly of FIG. 24A.
Figures 25A, 25B:
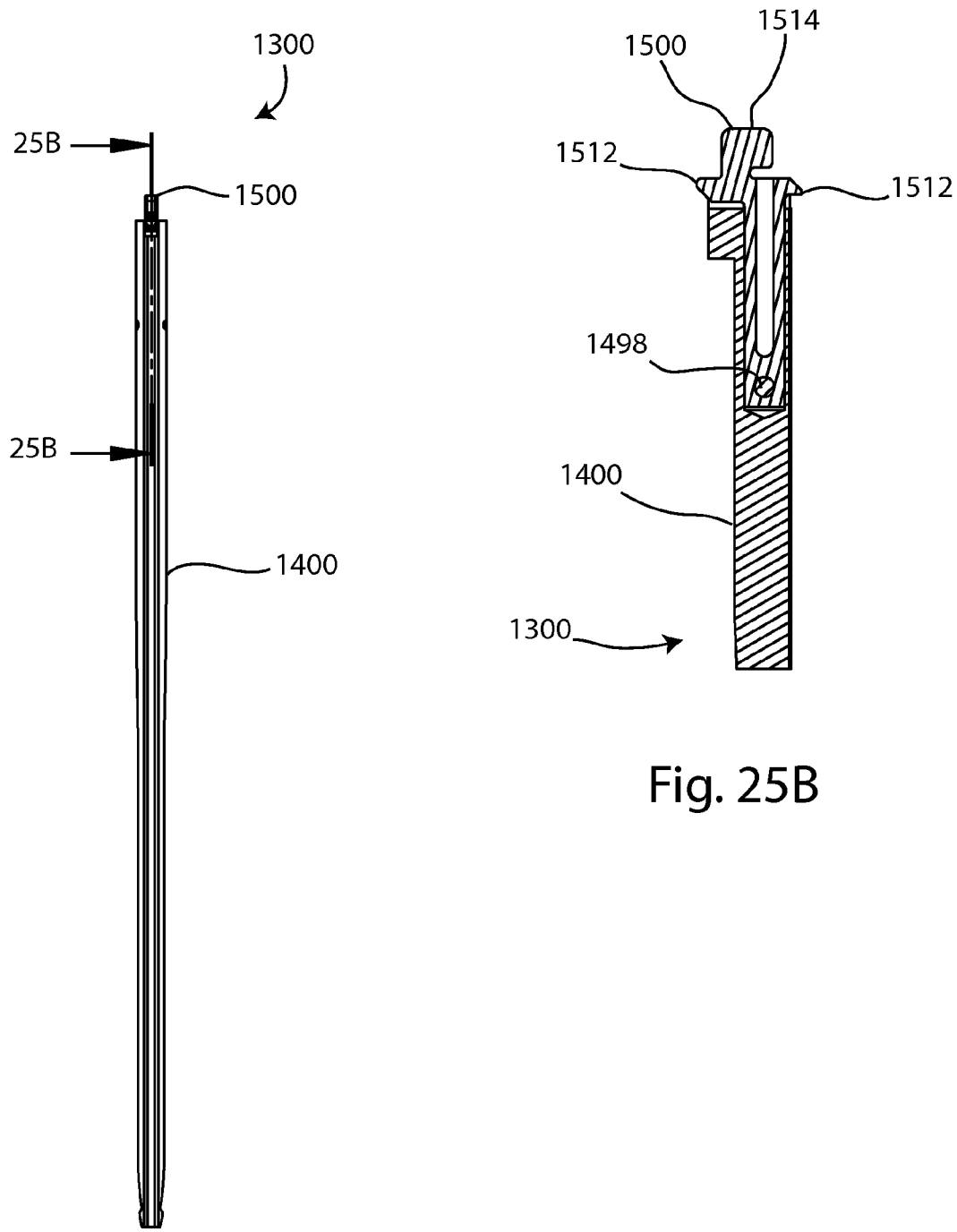
FIG. 25A is a side view of the arm assembly of FIG. 24A.
FIG. 25B is a cross section view of the arm assembly of FIG. 24A taken along line 25B-25B shown in FIG. 25A.
Figure 26:
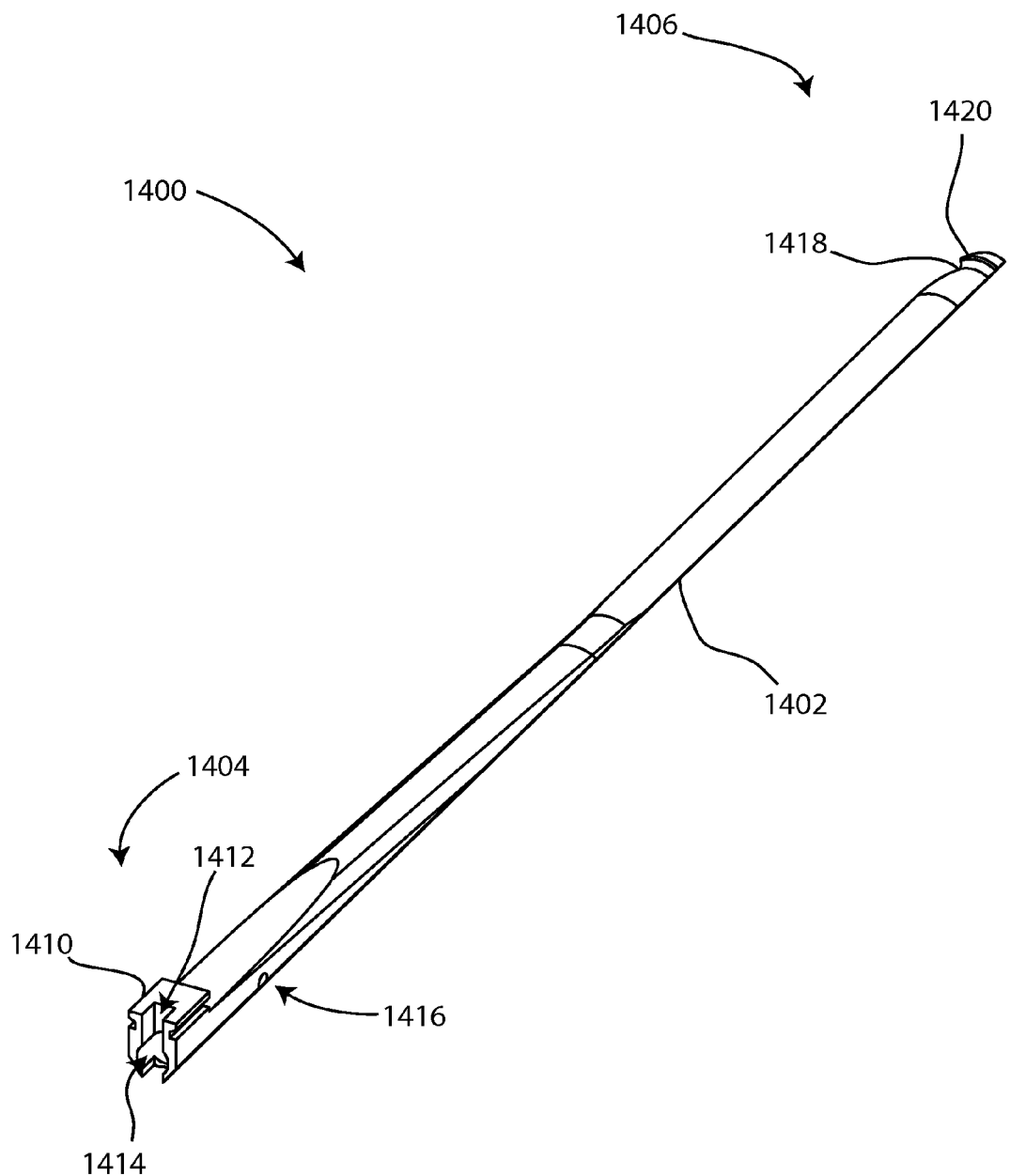
FIG. 26 is a perspective view of an arm of the arm assembly of FIG. 24A.
Figure 27:
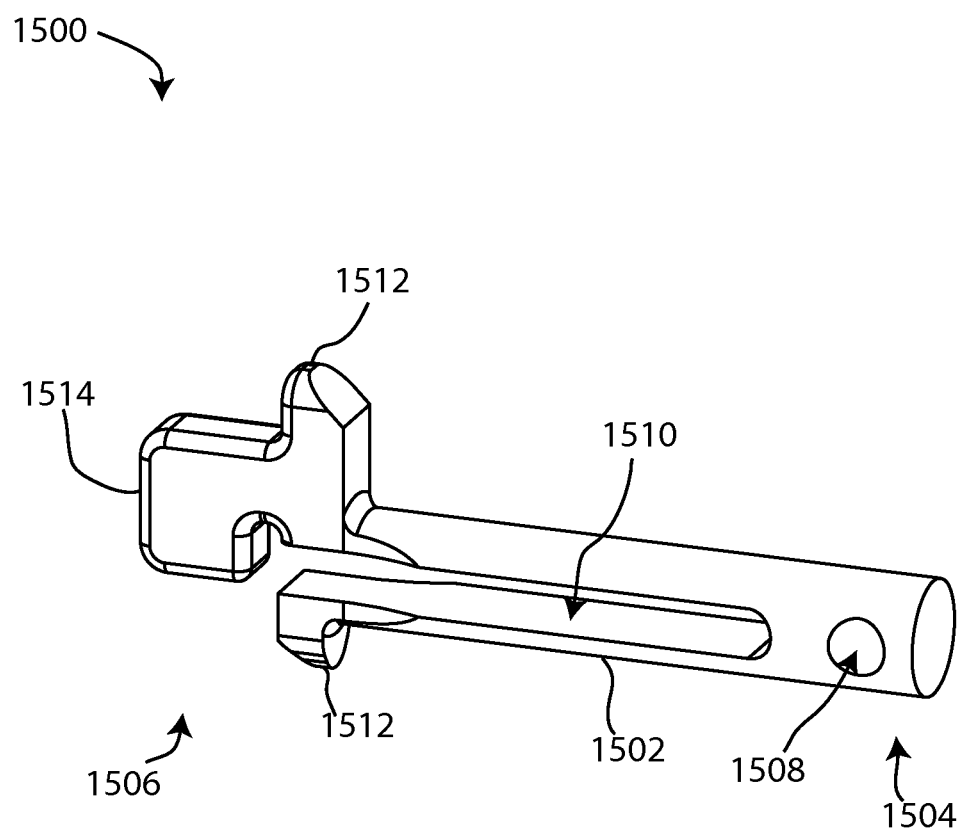
FIG. 27 is a perspective view of an arm lock of the arm assembly of FIG. 24A.

Referring to FIGS. 24B, 25B, and 27, an arm lock 1500, or latch, has an elongated shaft 1502 extending between a base 1504 and a head 1506. The base 1504 has a through hole 1508 which is sized and positioned to correspond to hole 1416 of arm 1400, and also sized and configured to complement fastener 1498. The arm lock 1500 has a slot 1510 which divides the shaft 1502 and head 1506 into two portions, leaving the base 1504 intact. Each portion of the head 1506 includes a lateral enlargement 1512 which may be tapered on one side and flat on an opposite side. It can be appreciated from FIG. 25B that the tapered sides on the two head portions may be oppositely oriented. At least one portion of the head 1506 may include another enlargement 1514, which may serve as a force input location to deflect the head portion.

Arm assembly 1300 may be assembled by sliding the base 1504 of arm lock 1500 into hole 1414 of arm 1400, rotating arm lock 1500 so that enlargement 1514 is proximate the dovetail protrusion 1410 and a lateral enlargement 1512 is in slot 1412, and inserting fastener 1498 into holes 1416 and 1508.

Arm assembly 1300 may be connected to hub assembly 500 by sliding the dovetail protrusion 1410 into the dovetail slot 1206 so that the lateral enlargement 1512 engages the pocket 1208. In some embodiments, the dovetail connection may be configured to permit the arm assembly 1300 to be adjustably connected to the hub assembly 500. For example, the dovetail slot 1206 may be lengthened and provided with multiple pockets 1208. This arrangement would permit the dilation device 400 to approach the operative site obliquely while still permitting the tips 1406 of the arms 1400 to intimately engage the structures surrounding the operative site.

Figure 28:
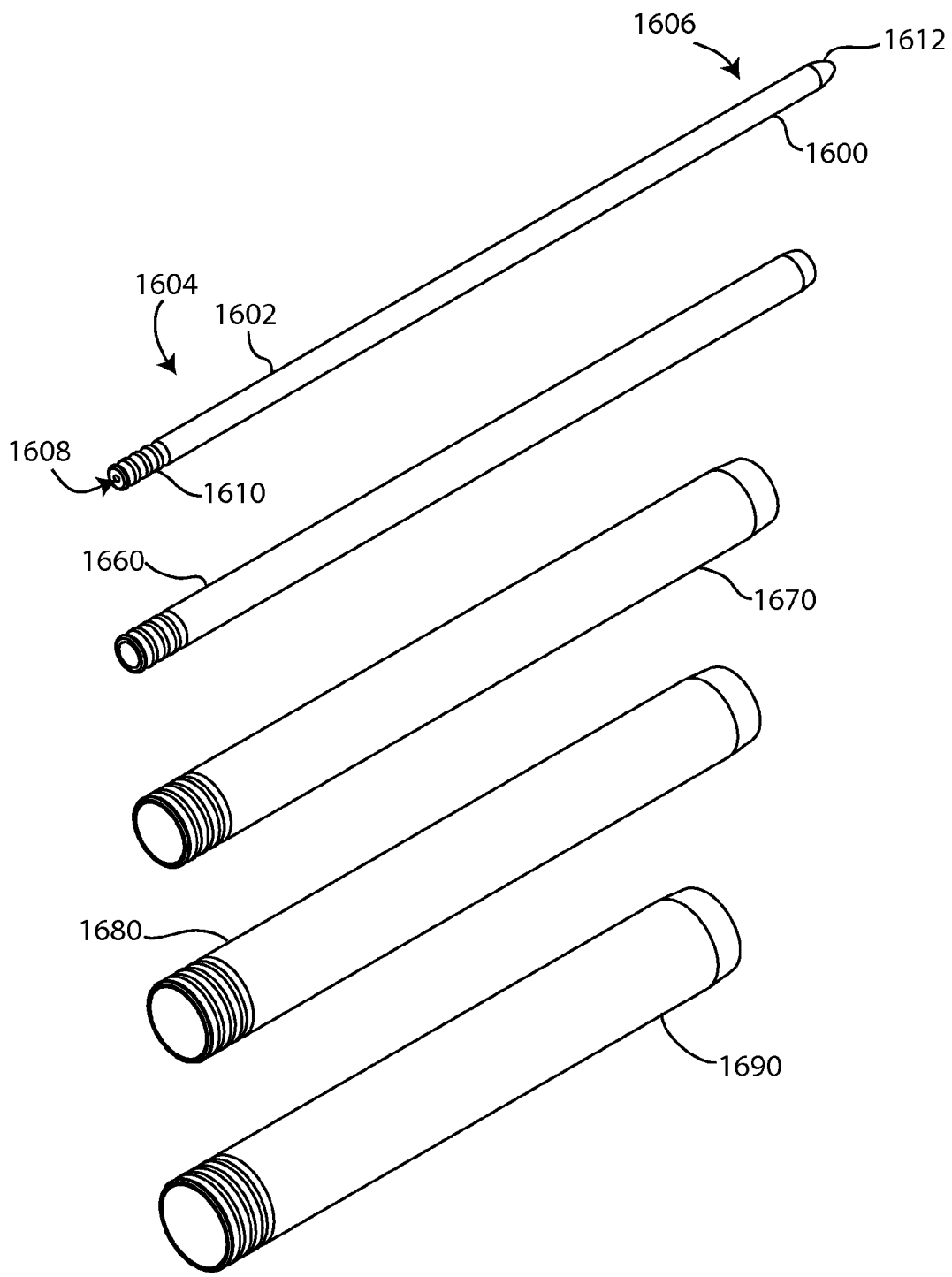
FIG. 28 is a perspective view of a set of dilators.

FIG. 28 illustrates a set of dilators 1600, 1660, 1670, 1680, 1690. Dilator 1600 has an elongated shaft 1602 extending between a base 1604 and a tip 1606. A through hole 1608 extends the length of dilator 1600. Hole 1608 may be sized to complement a guide wire, K-wire, Beath pin, stylus, or other small diameter rod. The base 1604 may be smooth or textured. For example, FIG. 28 illustrates a textured base 1604 which has a regular pattern of grooves 1610. Other textures are contemplated, such as knurling, dimples, or sandblasting. The tip 1606 includes a tapered region 1612 to reduce the outside diameter toward the end. The other dilators 1660, 1670, 1680, 1690 in the set may share some or all of the characteristics described for dilator 1600. However, the outside diameter and inside diameter of each dilator may be selected so that all the dilators nest together with clearance. In this situation, the set of dilators may be described as a set of sequential dilators, since each incrementally larger dilator slides over the next smaller size dilator. The dilators may be color coded to communicate their relative size.

Figure 29:
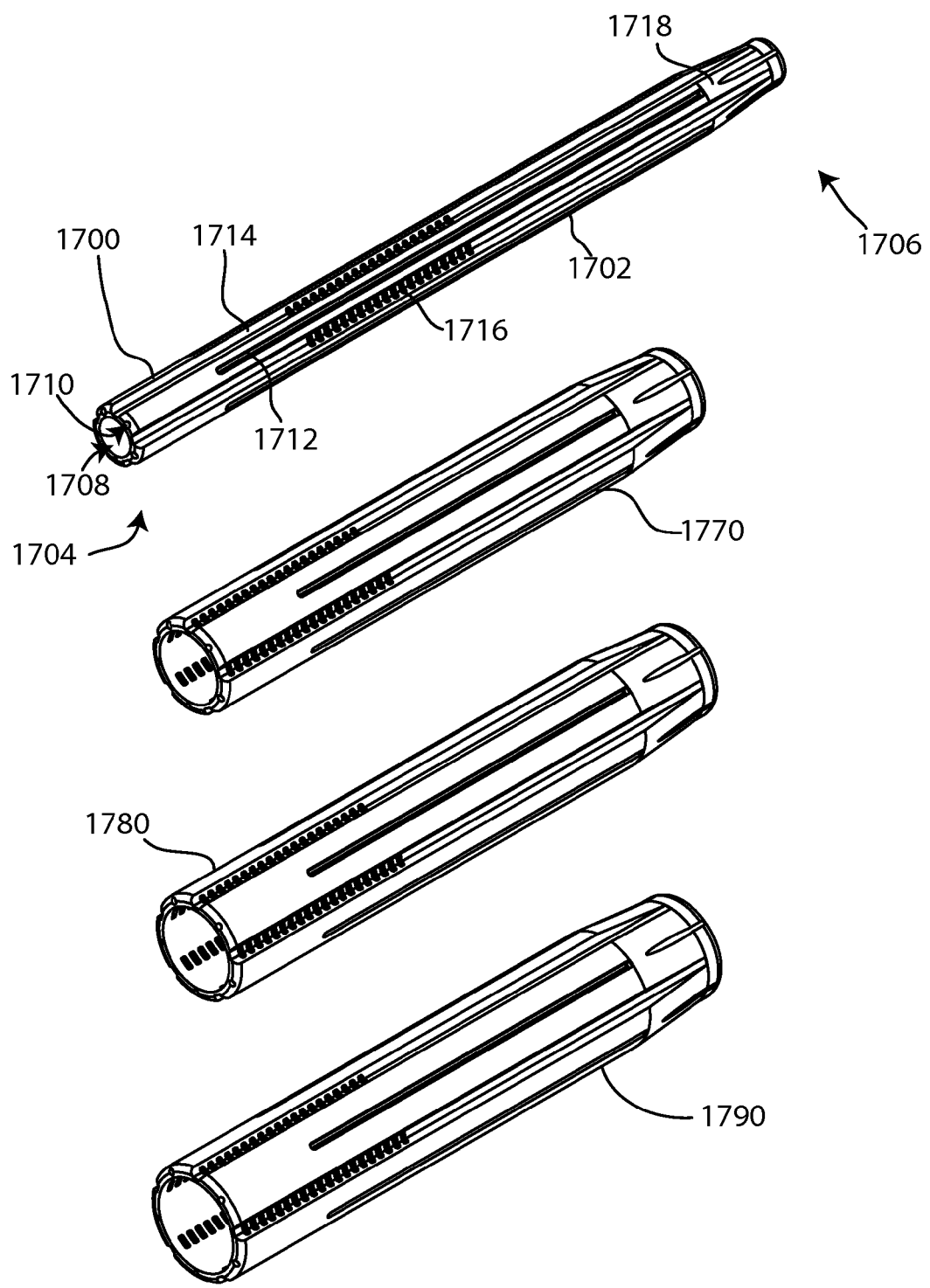
FIG. 29 is a perspective view of a set of cannulas.

FIG. 29 illustrates a set of cannulas 1700, 1770, 1780, 1790. Cannula 1700 has an elongated shaft 1702 extending between a base 1704 and a tip 1706. A central through hole 1708 extends the length of cannula 1700. Hole 1708 may be sized to complement one of the dilators 1600, 1660, 1670, 1680, 1690, such as dilator 1660 for example. One or more peripheral through holes 1710 may extend the length of cannula 1700. One or more external longitudinal grooves 1712 may be positioned to intersect, or interrupt, at least a portion of the length of holes 1710. For example, FIG. 29 shows groove 1712 interrupting a middle portion of hole 1710. Cannula 1700 may also include one or more external longitudinal grooves 1714 which are separated from hole 1710. FIG. 29 shows cannula 1700 with a pattern of five evenly spaced grooves 1714 which alternate with five evenly spaced holes 1710. Cannula 1700 may also include one or more windows 1716 in the bottom of each groove 1714, as shown best in FIG. 30B. For example, cannula 1700 has a pattern of twenty closely-spaced windows in the bottom of each groove 1714. The base 1704 may be smooth or textured. For example, FIG. 29 illustrates a smooth base 1704. The tip 1706 includes a tapered region 1718 to reduce the outside diameter toward the end. The other cannulas 1770, 1780, 1790 in the set may share some or all of the characteristics described for cannula 1700. However, the inside diameter of each cannula may be selected so that the cannula slides over a corresponding dilator with clearance. For example, cannula 1700 may slide over dilator 1660, cannula 1770 may slide over dilator 1670, cannula 1780 may slide over dilator 1680, and cannula 1790 may slide over dilator 1690. Furthermore, the inside diameter of at least one of the cannulas in the set may be selected to correspond to the outer dimension of an instrument or implant which must fit through the cannula. For example, the inside diameter of cannula 1700 may be selected to correspond to the outer dimension of a spinal discectomy instrument, while the inside diameter of cannula 1780 may be selected to correspond to the outer dimensions of a spinal implant, such as a fusion cage. Clearly, when such selections are made for the cannulas, corresponding selections may be necessary in the dilators. The cannulas may be color coded to communicate their relative size or their corresponding dilator. In some embodiments, one or more of the cannulas may be tapered so that the inside diameter at the tip 1706 corresponds to the outside diameter of a dilator, but the inside diameter at the base 1704 is larger. In still other embodiments, one or more of the cannulas may be shorter than the arms 1400. The cannulas may be so short as to resemble a ring. Such a cannula may be inserted among the tips 1406 of the arms 1400.

The dilators 1600, 1660, 1670, 1680, 1690 and/or cannulas 1700, 1770, 1780, 1790 may be at least partially radiolucent. Alternatively, the dilators and/or cannulas may be at least partially radiopaque. The dilators and/or cannulas may comprise metals such as aluminum, stainless steel, titanium, and other biocompatible metals. The dilators and/or cannulas may also comprise high density plastics such as Delrin, Radel, Udel, poly ether ether ketone (PEEK), polycarbonate, and acrylonitrile butadiene styrene (ABS), among others. The dilators and/or cannulas may be fabricated by machining, molding, casting, or other manufacturing operations. Barium sulphate may be added to constituent plastic materials to provide increased radiopacity. The dilators and/or cannulas may be reusable or disposable. The dilators and/or cannulas may conduct light or function as a light guide or light conductor. The dilators and/or cannulas may accept a reusable light ring, collar, or cap; fiber optic cables; or other light source. For example, a reusable light collar may snap onto a base 1704 of a cannula 1700 and key with the grooves 1714, distributing light throughout a clear cannula. In another example, a disposable battery powered light source may be at least partially insertable into one or more of the holes 1710, distributing light to the tip 1706 of the cannula.

FIGS. 30A-30B illustrate dilation device 400 operatively assembled with cannula 1700. The dilation device 400 is in an open configuration and cannula 1700 is in the middle of the circular pattern of arm assemblies 1300. Each arm 1400 rests in a corresponding groove 1714, and a lateral enlargement 1512 of each arm lock 1500 rests in a corresponding window 1716. Groove 1714 and lateral enlargement 1512 may cooperate to guide insertion of the cannula 1700 into the dilation device 400. It can be appreciated that the orientation of the tapered and flat sides of the lateral enlargement 1512 and the inherent resilience or spring-like property of the slotted shaft 1502 act to readily permit passage of the cannula 1700 in one direction, and act to prevent passage of the cannula 1700 in an opposite direction. Referring to FIG. 30B, cannula 1700 will pass readily to the right, but is prevented from passing to the left. In this way, cannula 1700 may be prevented from unintended expulsion due to the resistance of the tissues in which it resides.

Figure 31A:
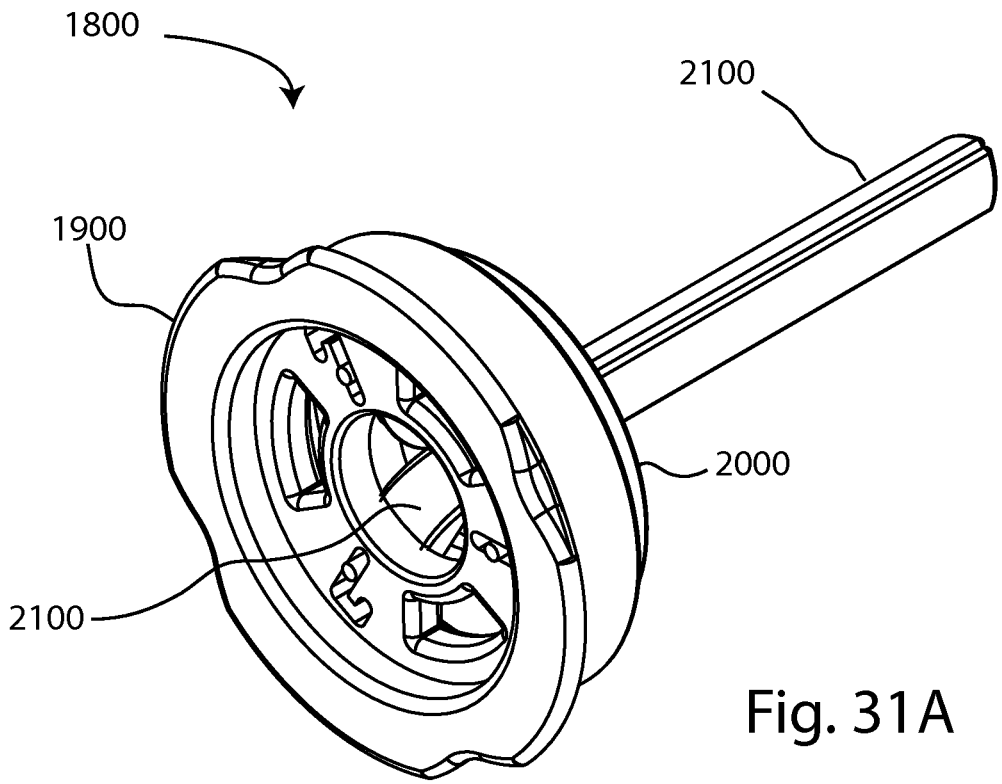
FIG. 31A is a perspective view of yet another tissue dilation device in a closed configuration.
Figure 31B:
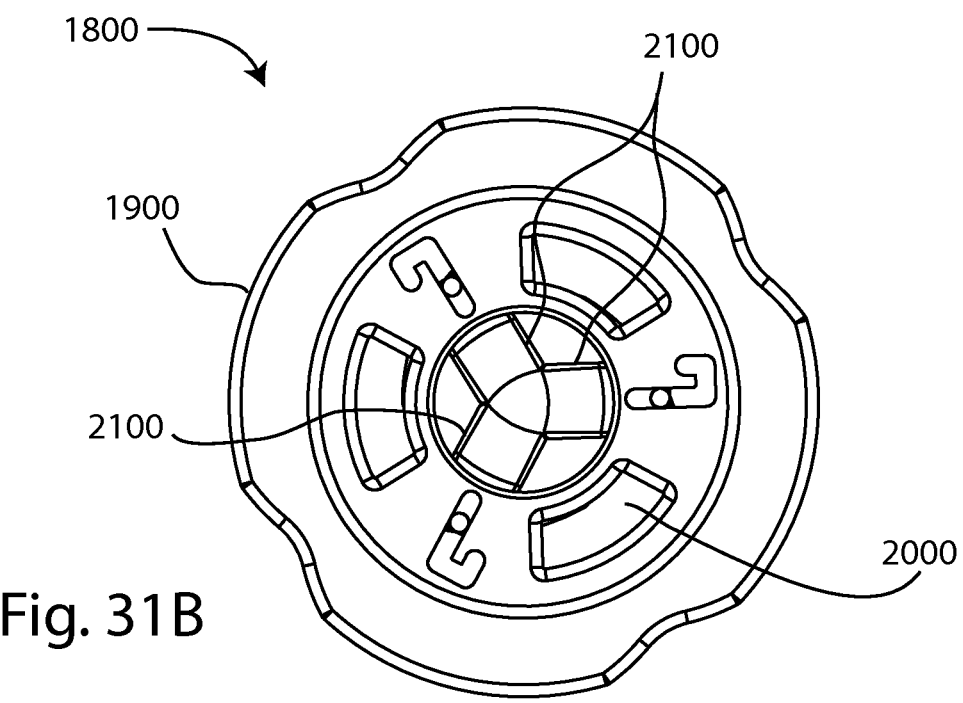
FIG. 31B is a top view of the tissue dilation device of FIG. 31A in a closed configuration.
Figure 32A:
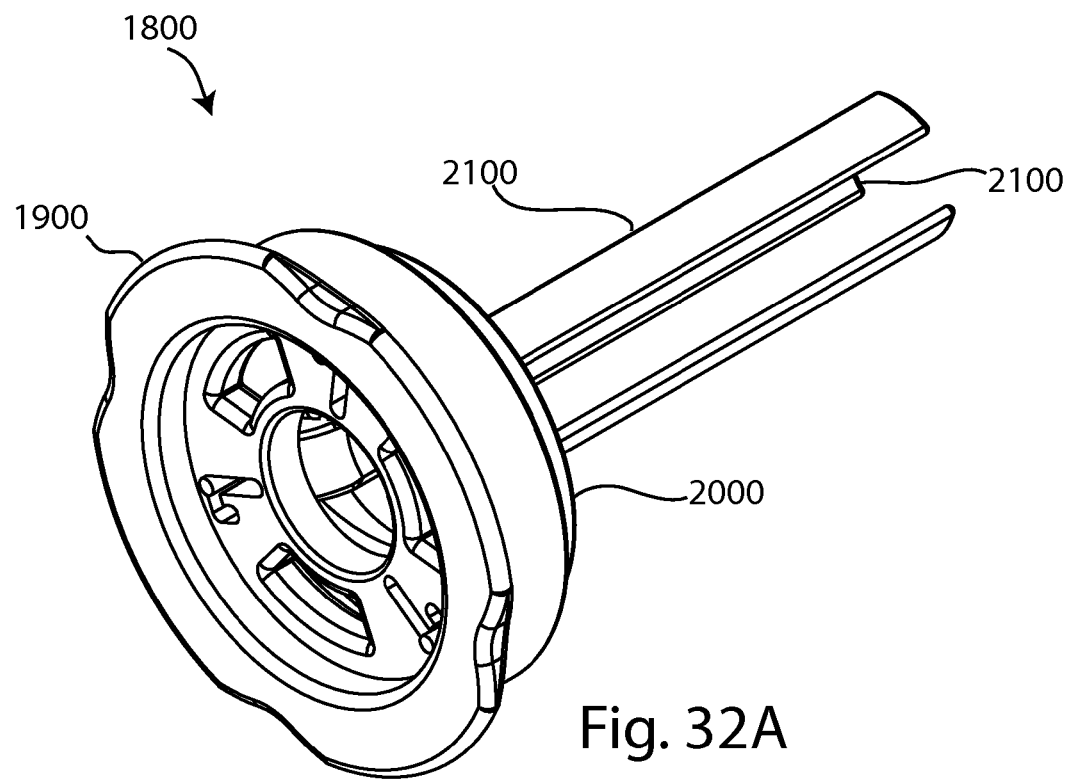
FIG. 32A is a perspective view of the tissue dilation device of FIG. 31A in an unlocked open configuration.
Figure 32B:
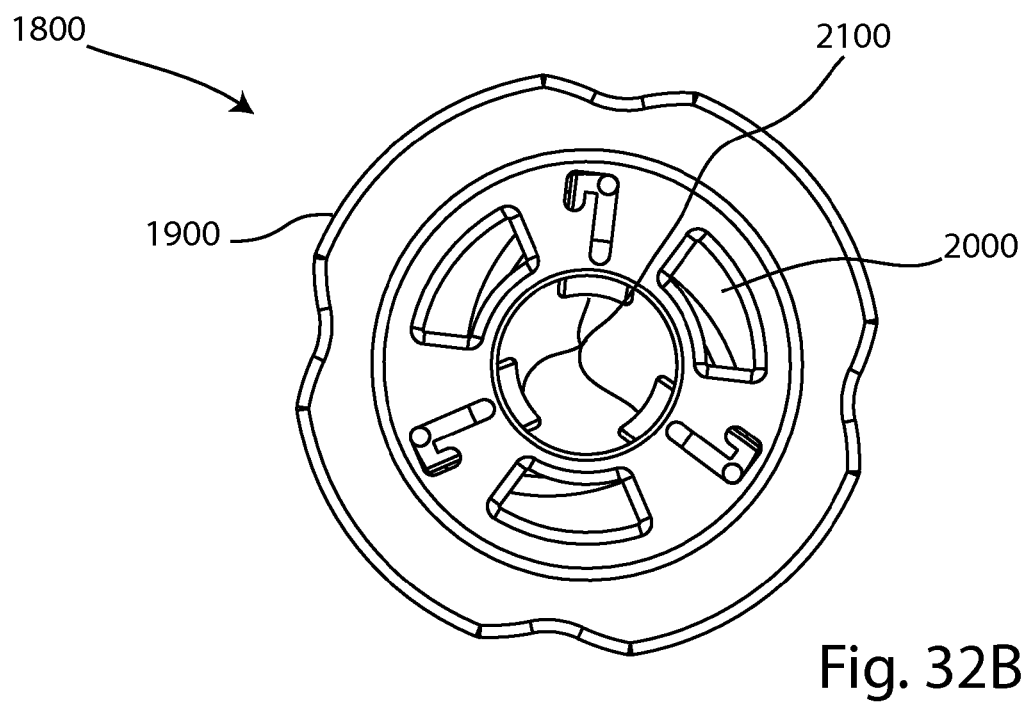
FIG. 32B is a top view of the tissue dilation device of FIG. 31A in an unlocked open configuration.
Figure 33A:
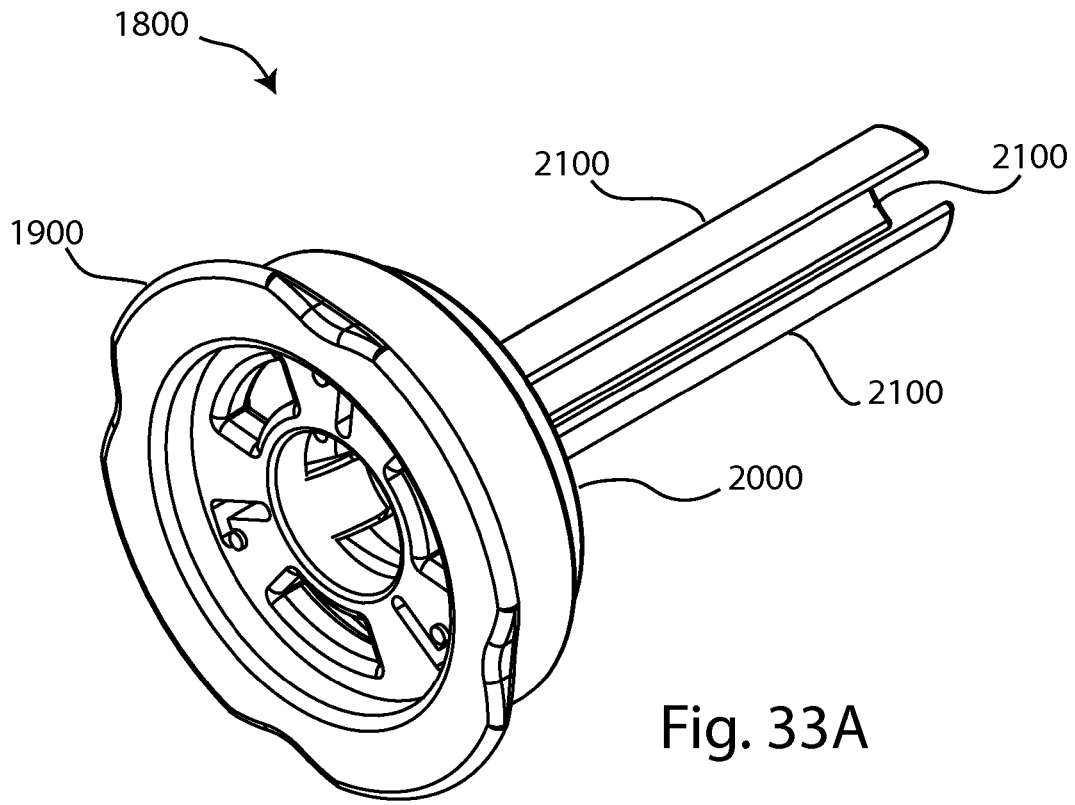
FIG. 33A is a perspective view of the tissue dilation device of FIG. 31A in a locked open configuration.
Figure 33B:
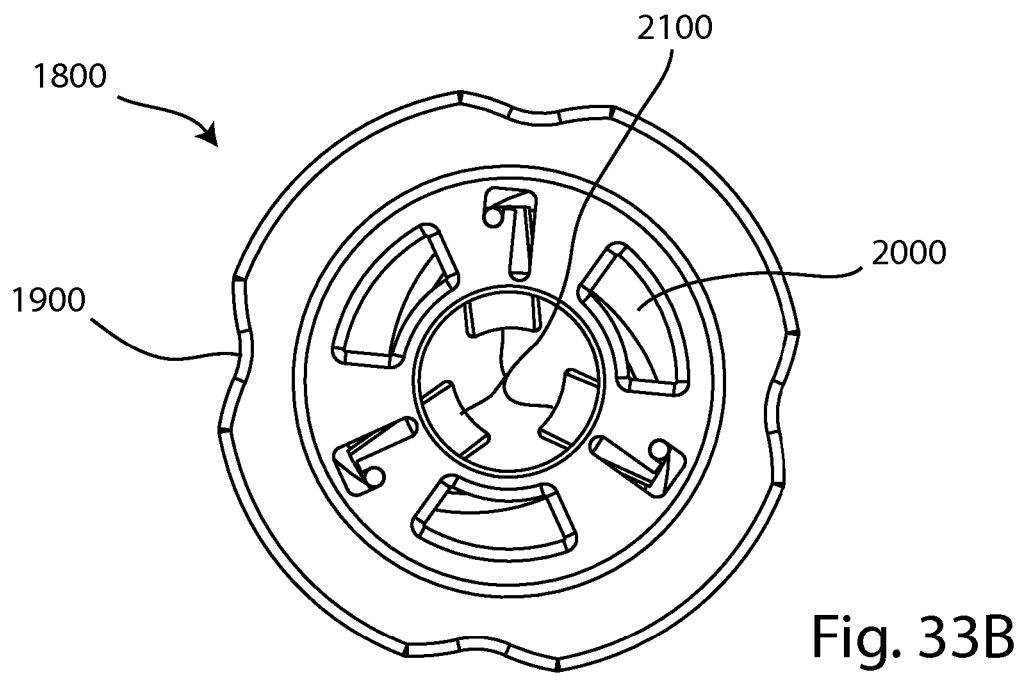
FIG. 33B is a top view of the tissue dilation device of FIG. 31A in a locked open configuration.

FIGS. 31A-37B illustrate another dilation device 1800. Dilation device 1800 may also be described as a dilation assembly since it includes several component parts in an operative arrangement. FIGS. 31A-31B show dilation device 1800 in a closed configuration. FIGS. 32A-32B show dilation device 1800 in an open unlocked configuration. FIGS. 33A-33B show dilation device 1800 in an open locked configuration. Dilation device 1800 includes a stationary disk 1900, a drive disk 2000, and three arms 2100. Alternate embodiments may include two or more arms. The arms 2100 are carried by the stationary disk 1900 and the drive disk 2000. In this embodiment, the arms 2100 are evenly spaced in a circular or triangular pattern around the disks 1900, 2000, although non-circular or non-symmetric arrangements are contemplated. The pattern of arms 2100 synchronously expands and contracts relative to the two disks 1900, 2000. In other words, each arm 2100 is radially movable relative to a center of the pattern.

A portion of the dilation device 1800 may be introduced into a muscle, other tissue, or natural passageway in the closed configuration, and the dilation device 1800 expanded from the closed configuration to the open configuration. If introduced into a muscle, the expansion of dilation device 1800 bluntly dissects and separates the muscle fibers. The expansion of dilation device 1800 forms an open passage through the muscle, tissue, or natural passageway, through which instruments, implants and other materials may be passed to perform one or more surgical procedures.

Figure 35A:
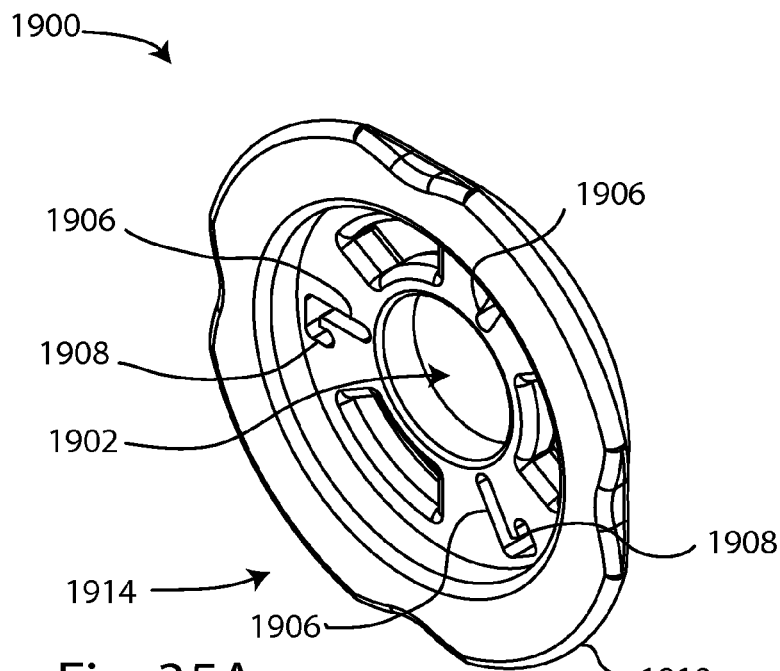
FIG. 35A is a perspective view of a stationary disk of the tissue dilation device of FIG. 31A.
Figure 35B:
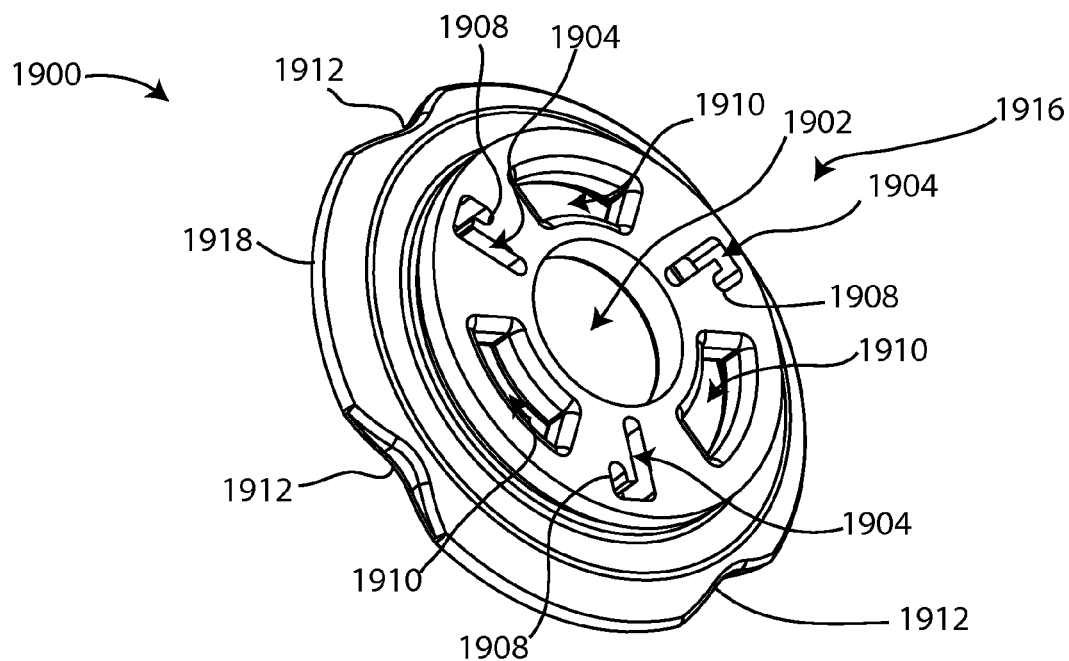
FIG. 35B is another perspective view of the stationary disk of FIG. 35A from another direction.

FIGS. 35A-35B illustrate a stationary disk 1900 shaped as a ring or annulus with a central aperture 1902. Stationary disk 1900, as illustrated, has a concave side 1914 and a convex side 1916, and may include a peripheral flange 1918. Stationary disk 1900 includes three slots 1904. Each slot 1904 may include a radial portion 1906 and a locking portion 1908. The locking portion 1908 of stationary disk 1900 may be described as a dogleg, an "L", or a "U". Other locking portions are contemplated, such as an obliquely angled portion or a tapering portion. One or more additional windows 1910 may be present, for example, to reduce weight or provide easy access for cleaning. Stationary disk 1900 may include one or more peripheral indentations 1912 or other grip features, such as grooves or texturing.

Figure 36A:
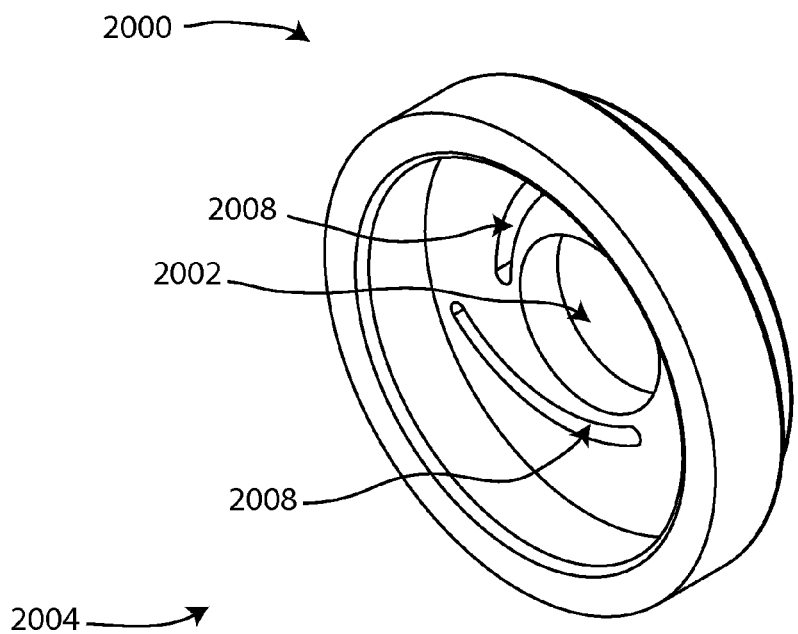
FIG. 36A is a perspective view of a drive disk of the tissue dilation device of FIG. 31A.
Figure 36B:
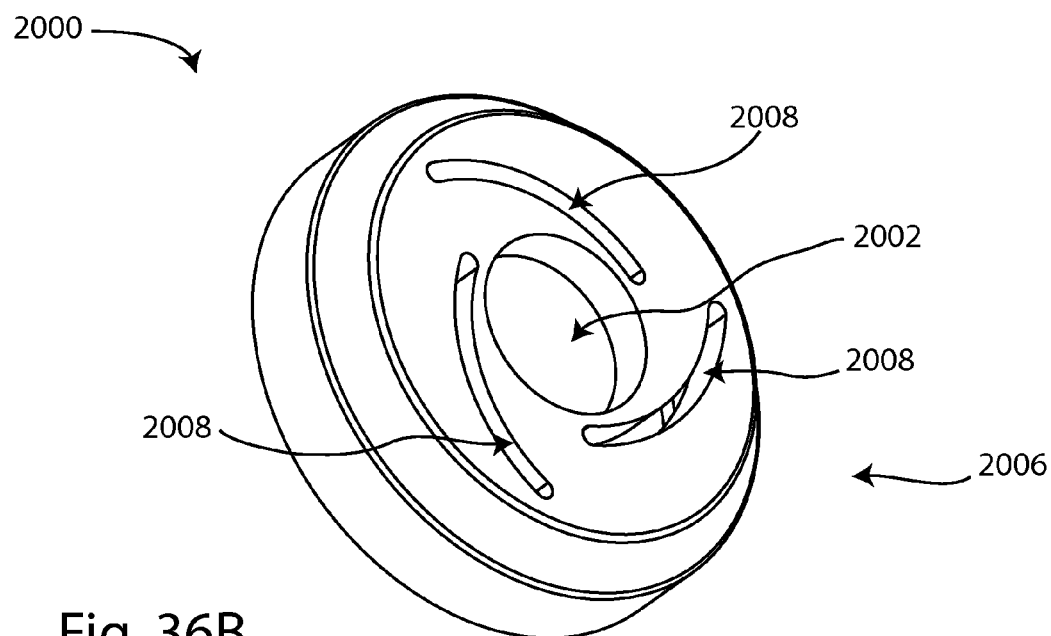
FIG. 36B is another perspective view of the stationary disk of FIG. 36A from another direction.

FIGS. 36A-36B illustrate a drive disk 2000 shaped as a ring or annulus with a central aperture 2002. Drive disk 2000, as illustrated, has a concave side 2004 and a convex side 2006. Drive disk 2000 includes three arcuate, obliquely-extending slots 2008 evenly spaced around the disk.

Figure 37A:
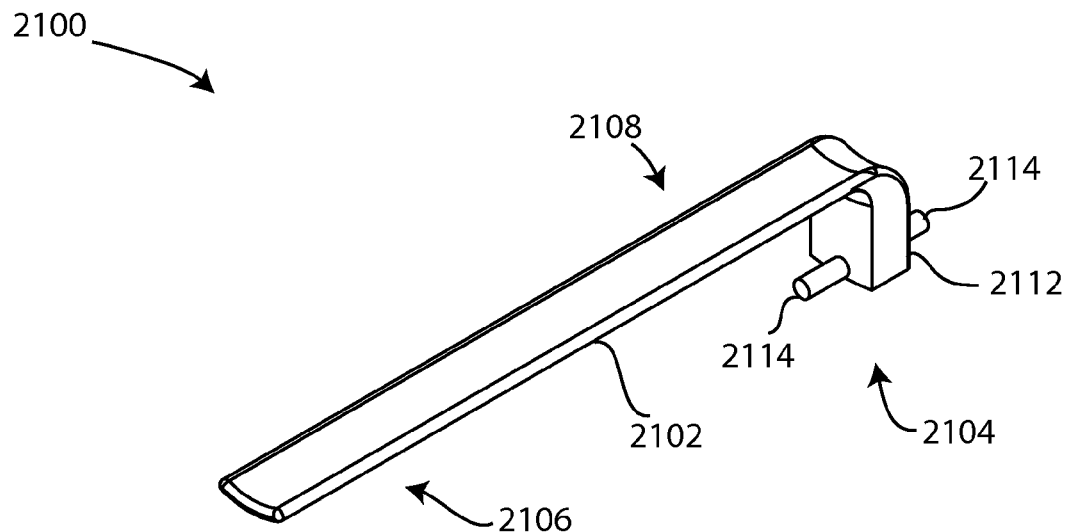
FIG. 37A is a perspective view of an arm of the tissue dilation device of FIG. 31A.
Figure 37B:
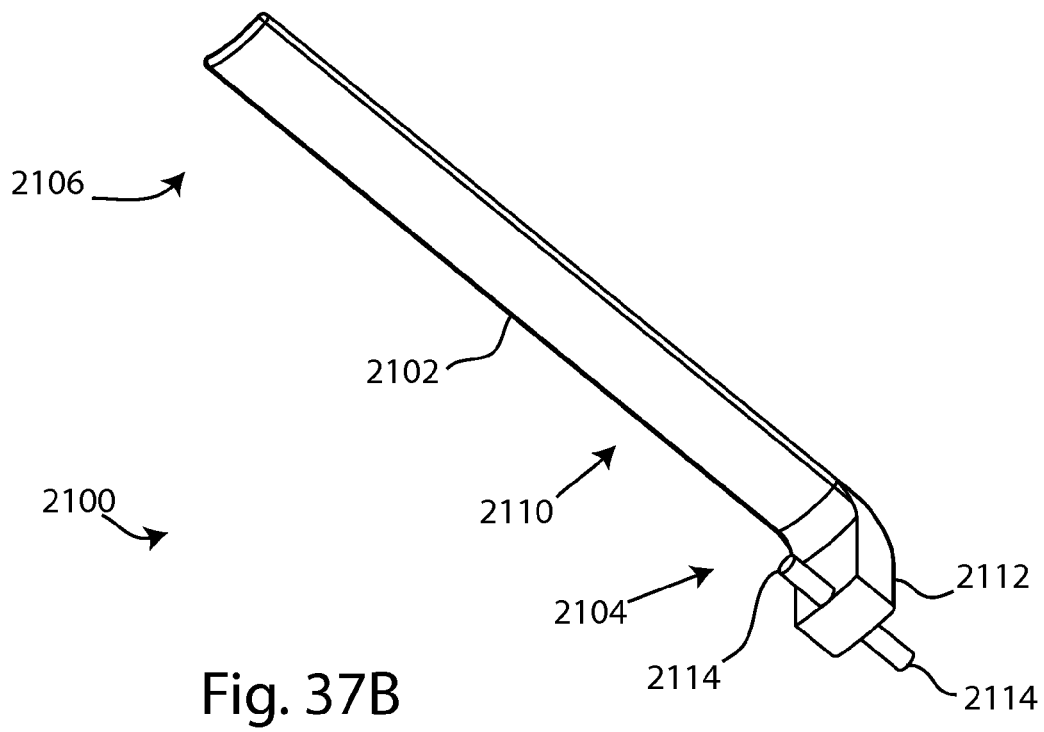
FIG. 37B is another perspective view of the arm of FIG. 37A from another direction.
Figure 38:
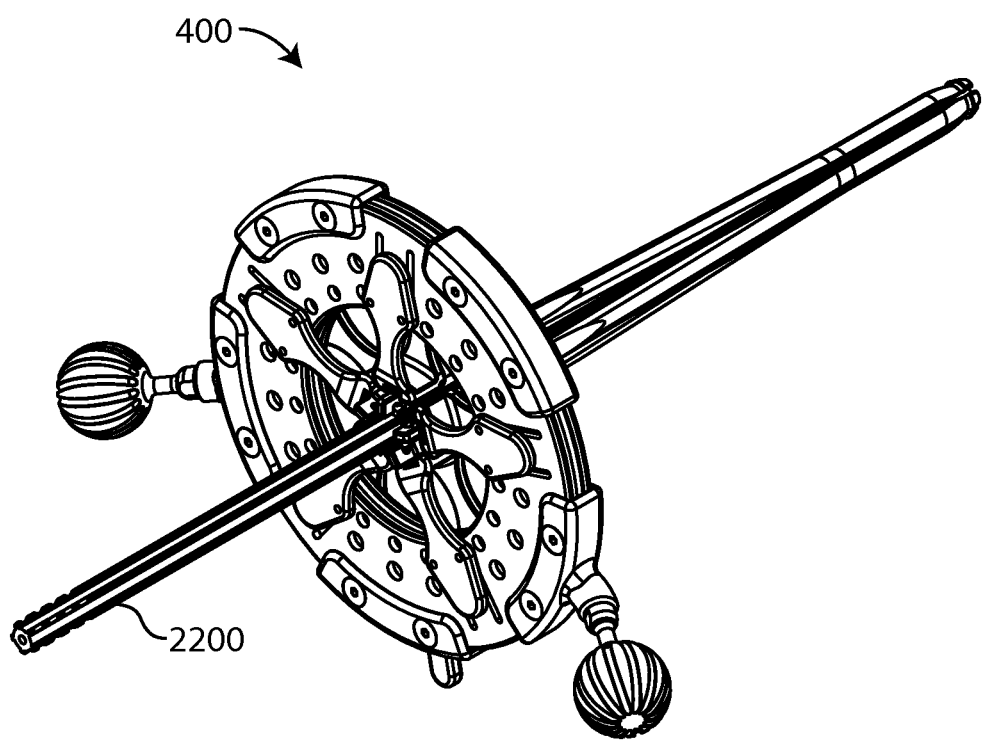
FIG. 38 is a perspective view of the tissue dilation device of FIG. 16 operatively assembled with a retainer.

FIGS. 37A-37B illustrate an arm 2100, or blade, with an elongated shaft 2102 extending between a base 2104 and a tip 2106. Shaft 2102 has a concave side 2108 and an opposite convex side 2110. Base 2104 includes a dogleg portion 2112, or L-shaped portion, which protrudes laterally from shaft 2102. A pair of bosses 2114 protrude from the dogleg portion 2112 generally parallel to the shaft 2102. In another embodiment, the bosses 2114 may be replaced by a pin secured in a hole in the L-shaped portion 2112.

Figure 34:
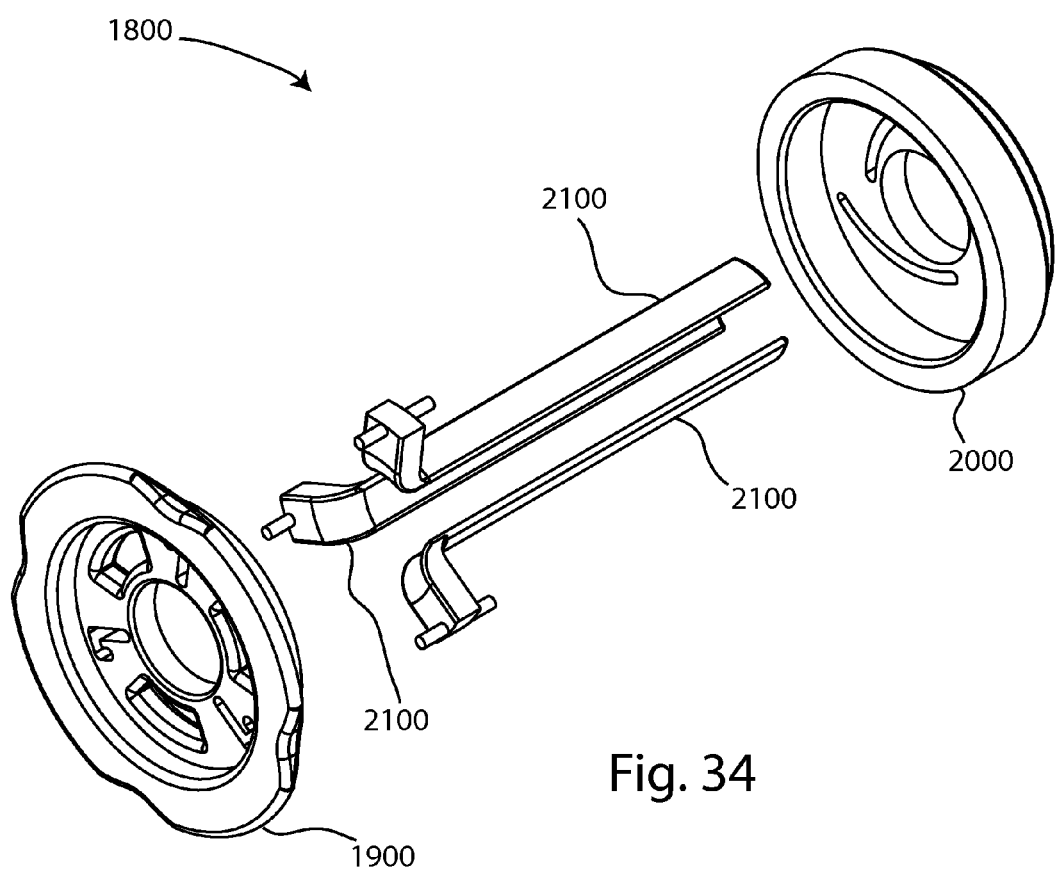
FIG. 34 is an exploded perspective view of the tissue dilation device of FIG. 31A.

Referring to FIG. 34, dilation device 1800 may be assembled by inserting a boss 2114 of an arm 2100 into a slot 2008 of the drive disk 2000 so that the dogleg portion 2112 is on the concave side 2004 and the shaft 2102 passes through the central aperture 2002. The remaining two arms 2100 may be assembled to the drive disk 2000 in a similar fashion. Stationary disk 1900 may be oriented so that the convex side 1916 faces the concave side 2004 and a boss 2114 is in each slot 1904. Stationary disk 1900 may be axially secured to drive disk 2000 while retaining freedom to rotate relative to drive disk 2000, at least within angular limits. For example, stationary disk 1900 may be connected to drive disk 2000 by a retaining ring (not shown).

Referring to FIGS. 38-40B, dilation device 400 is shown operatively assembled to a modified dilator 2200. Compared to dilators 1600, 1660, 1670, 1680, 1690 of FIG. 28, dilator 2200 has been modified to positively interact with arms 1400 to aid in holding the dilation device 400 closed during insertion into tissue or a natural passageway.

Figure 40A:
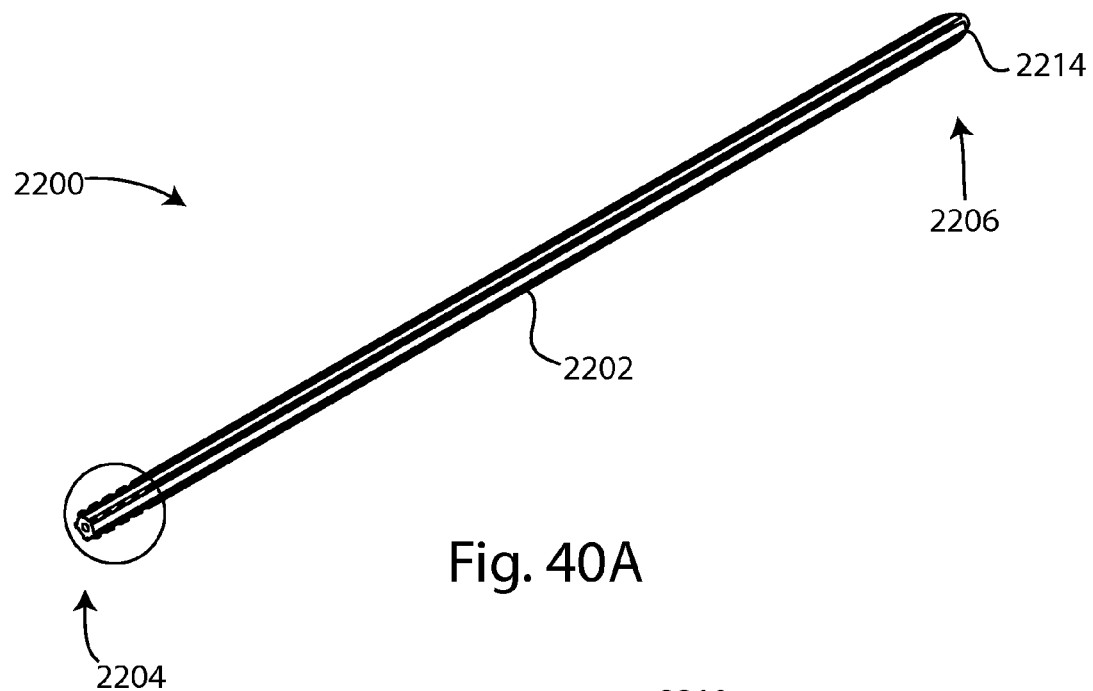
FIG. 40A is a perspective view of the retainer of FIG. 38.
Figure 40B:
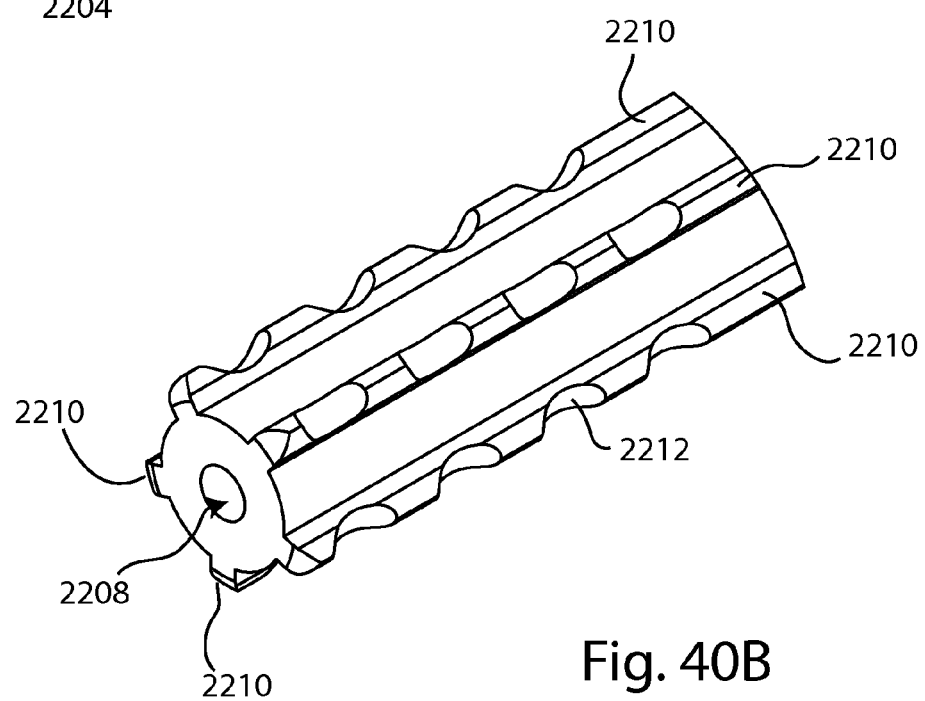
FIG. 40B is an enlarged detail view of a portion of the retainer of FIG. 38.
Figure 41A:
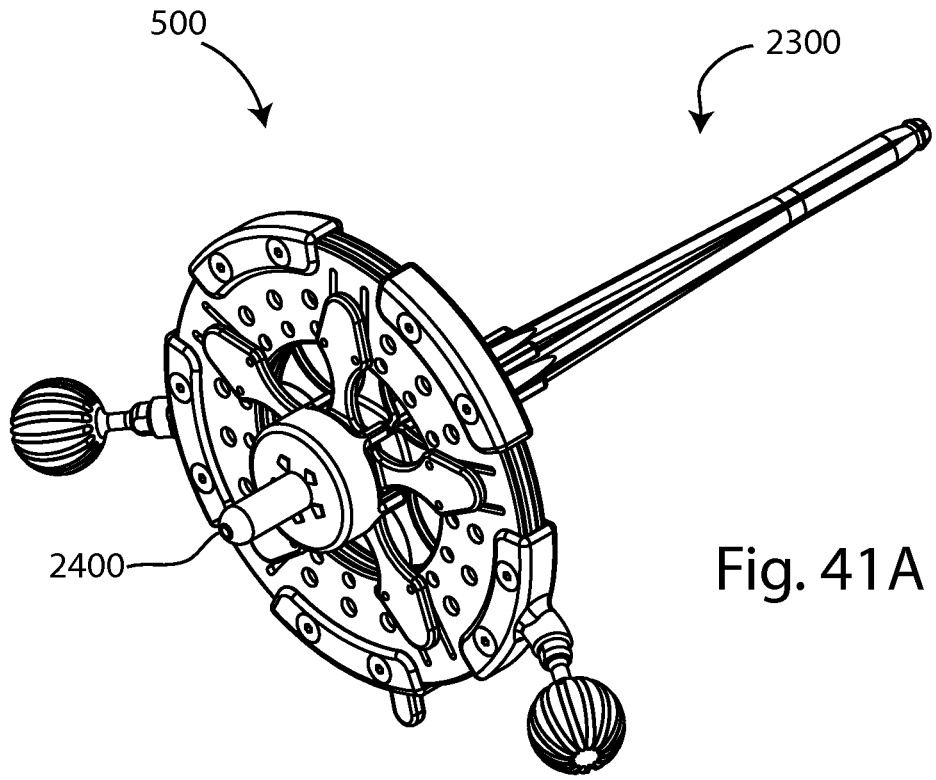
FIG. 41A is a perspective view of the hub assembly of FIG. 17 operatively assembled with a plurality of arm assemblies and a retainer.
Figure 41B:
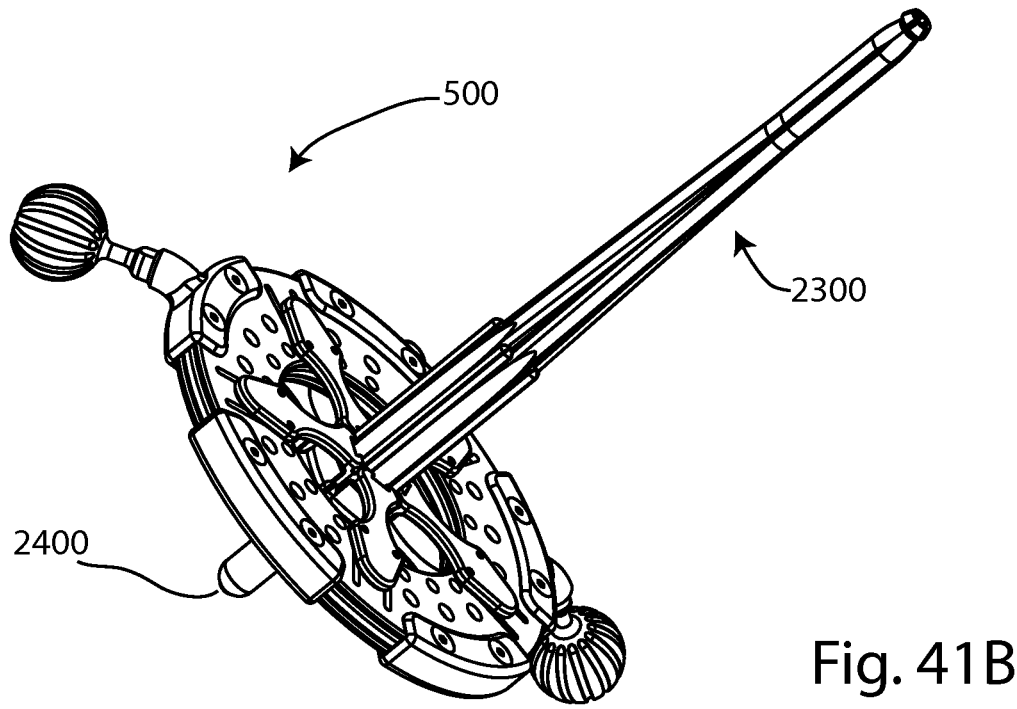
FIG. 41B is another perspective view of the hub assembly, arm assemblies, and retainer of FIG. 41A from another direction.
Figure 43:
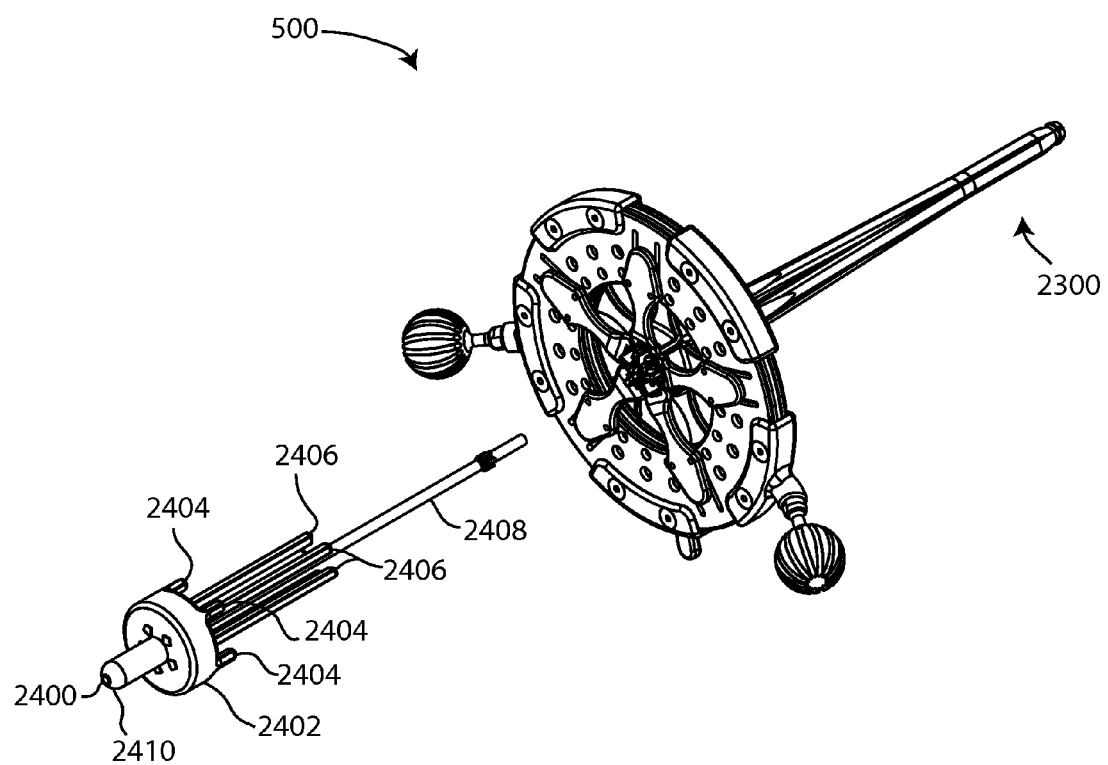
FIG. 43 is an exploded perspective view of the hub assembly, arm assemblies, and retainer of FIG. 41A.

Referring to FIGS. 40A-40B, dilator 2200 has an elongated shaft 2202 extending between a base 2204 and a tip 2206. A through hole 2208 extends the length of dilator 2200. Hole 2208 may be sized to complement a guide wire, K-wire, Beath pin, stylus, or other small diameter rod. One or more ribs 2210 extend the length of dilator 2200. As illustrated in FIG. 40B, dilator 2200 includes five evenly spaced ribs 2210. The base 2204 may be smooth or textured. For example, FIG. 28 illustrates a textured base 2204 which has a regular pattern of indentations 2212. Other textures are contemplated, such as knurling, dimples, or sandblasting. The tip 2206 includes a tapered region 2214 to reduce the outside diameter toward the end.

Figures 39A, 39B:
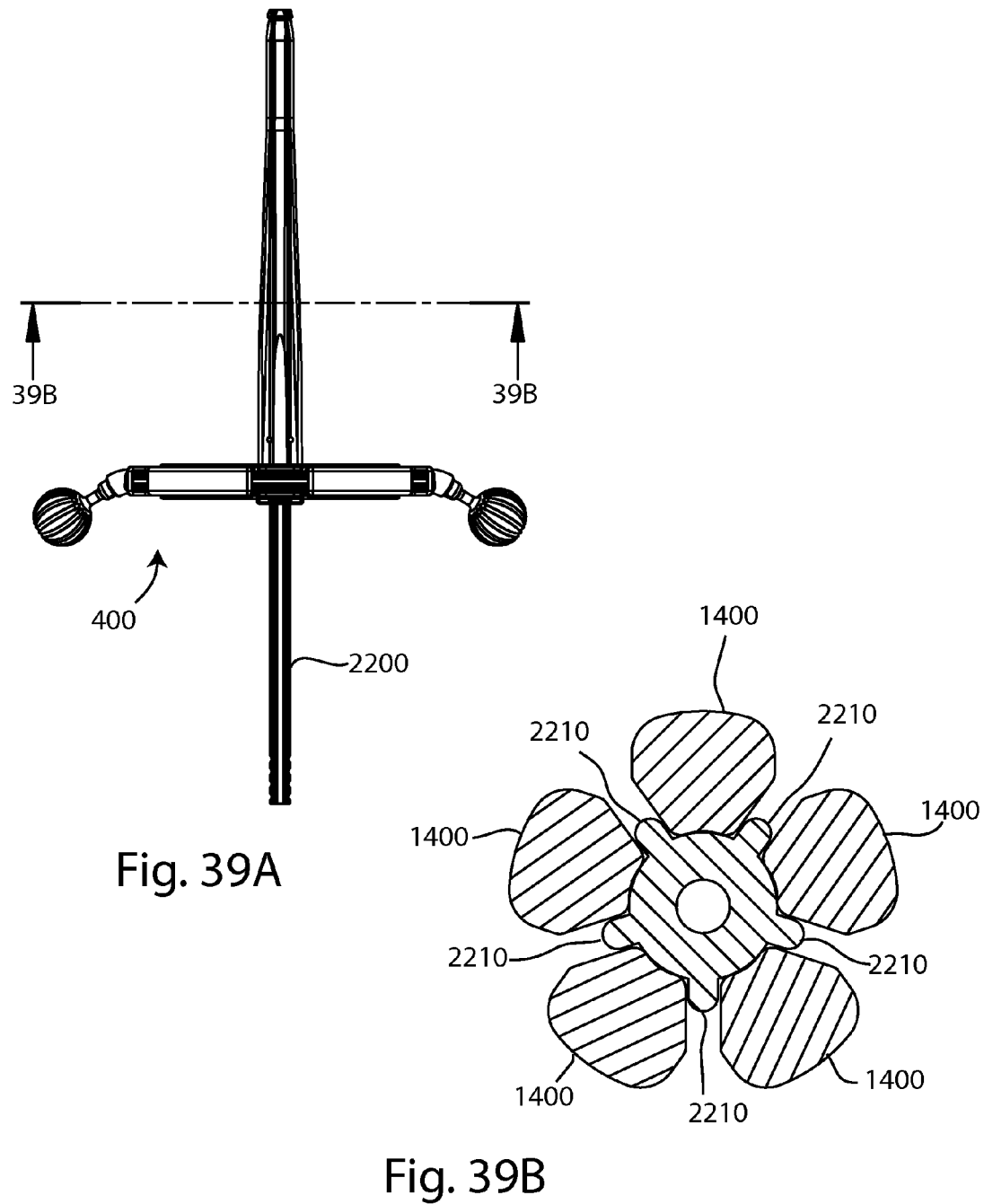
FIG. 39A is a front view of the tissue dilation device and retainer of FIG. 38.
FIG. 39B is a cross section view of the tissue dilation device and retainer of FIG. 38 taken along line 39B-39B of FIG. 39A.

FIG. 39B illustrates how the dilator 2200 positively engages the arms 1400 to hold the dilation device 400 closed during insertion. The dilator 2200 fits in the middle of the pattern of arms 1400 with the ribs 2210 between adjacent arms 1400. The ribs 2210 support the arms 1400 so that the arms 1400 remain straight during insertion. The arms 1400 are prevented from twisting or bending laterally while supported by the ribs 2210.

Referring to FIGS. 41A-45B, hub assembly 500 is shown operatively assembled to modified arm assemblies 2300 and an arm retention clip 2400. Compared to arm assembly 1300 of FIG. 24A, arm assembly 2300 has been modified to positively interact with arm retention clip 2400 to aid in holding the dilation device closed during insertion into tissue or a natural passageway. Arm retention clip 2400 may be connected to hub assembly 500 with arm assemblies 2300 before introducing the dilation device into tissue or a natural passageway, and may be removed after the dilation device is fully introduced.

Figure 44:
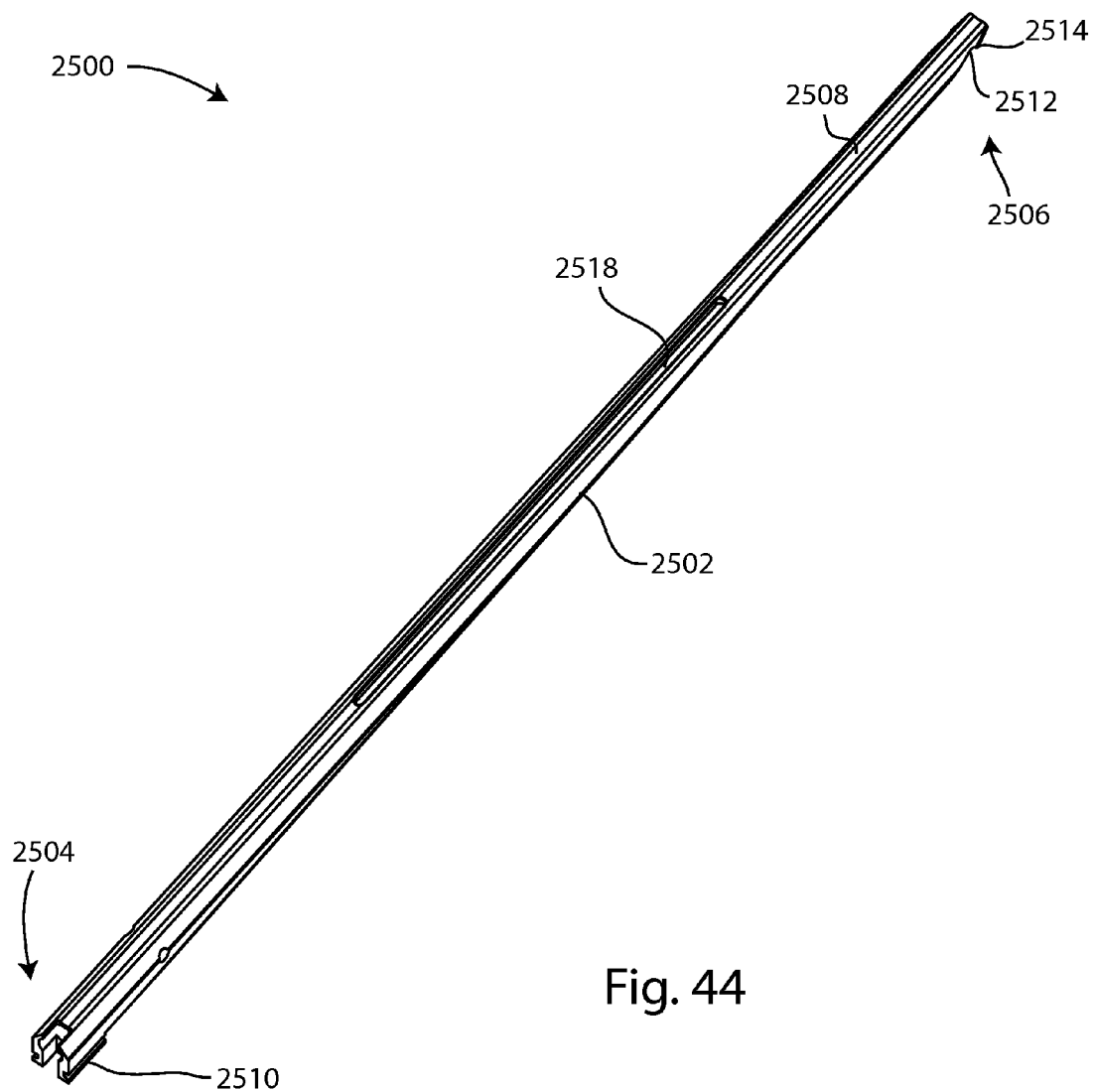
FIG. 44 is a perspective view of an arm of one of the arm assemblies of FIG. 41A.

FIG. 44 illustrates an arm 2500, or blade, with an elongated shaft 2502 extending between a base 2504 and a tip 2506. Arm 2500 may share some or all of the characteristics of arm 1400 of FIG. 26. One side of arm 2500 has a full length groove 2508 or depression, which is interrupted by a deeper groove 2518 centrally located along the shaft 2502 length. The base 2504 includes a dovetail protrusion 2510 on a side opposite the groove 2508. The dovetail protrusion 2510 may be sized and shaped to complement dovetail slot 1206 of arm clamp 1200. The tip 2506 includes a waist 2512 and an adjacent flared portion 2514. Together, the waist 2512 and flared portion 2514 form a concavely curved area on the tip 2506, which may aid in holding back or retaining tissues dissected and pushed aside by the dilation device.

Figures 45A, 45B:
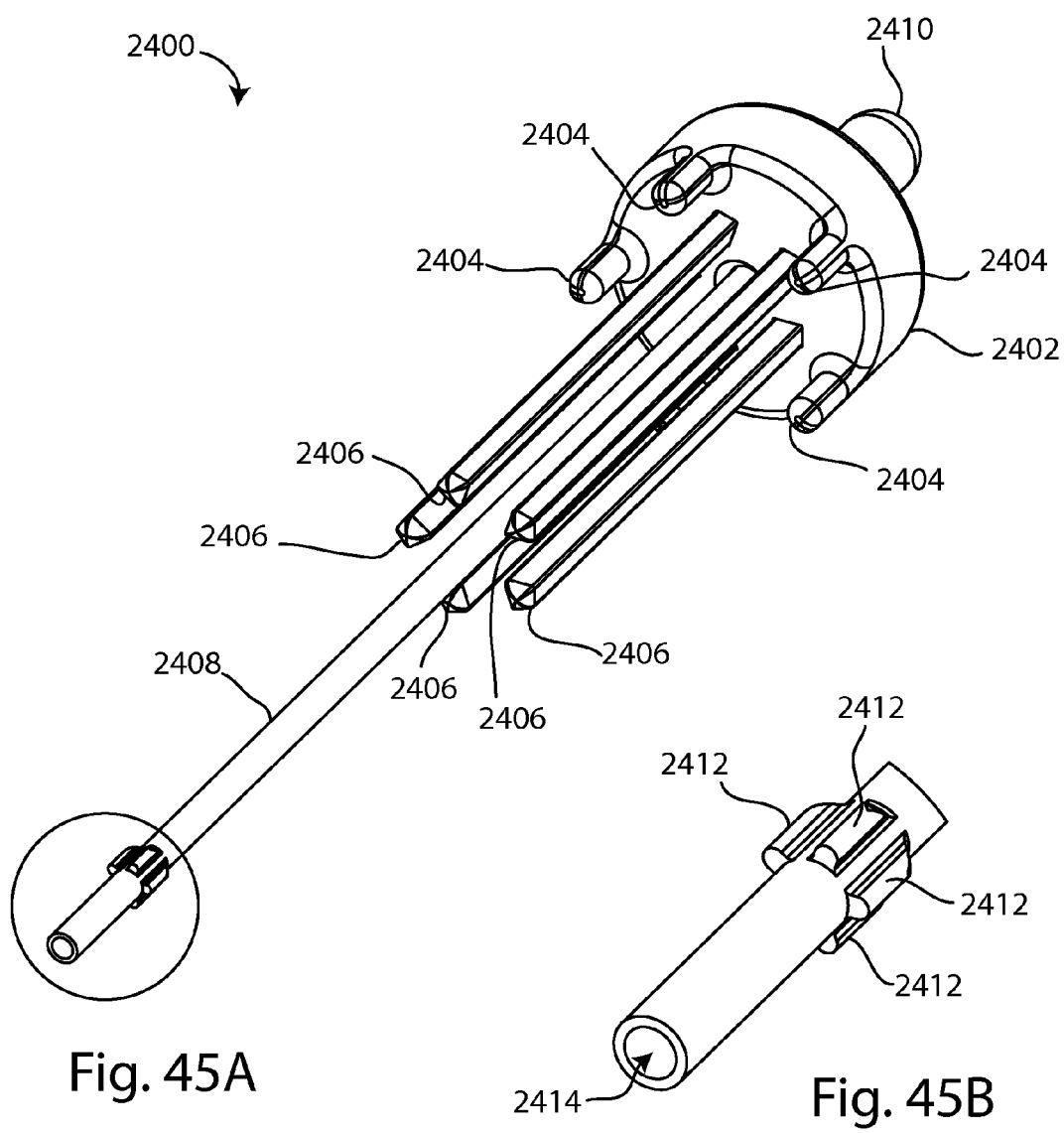
FIG. 45A is a perspective view of the retainer of FIG. 41A.
FIG. 45B is an enlarged detail view of a portion of the retainer of FIG. 41A.
Figure 47:
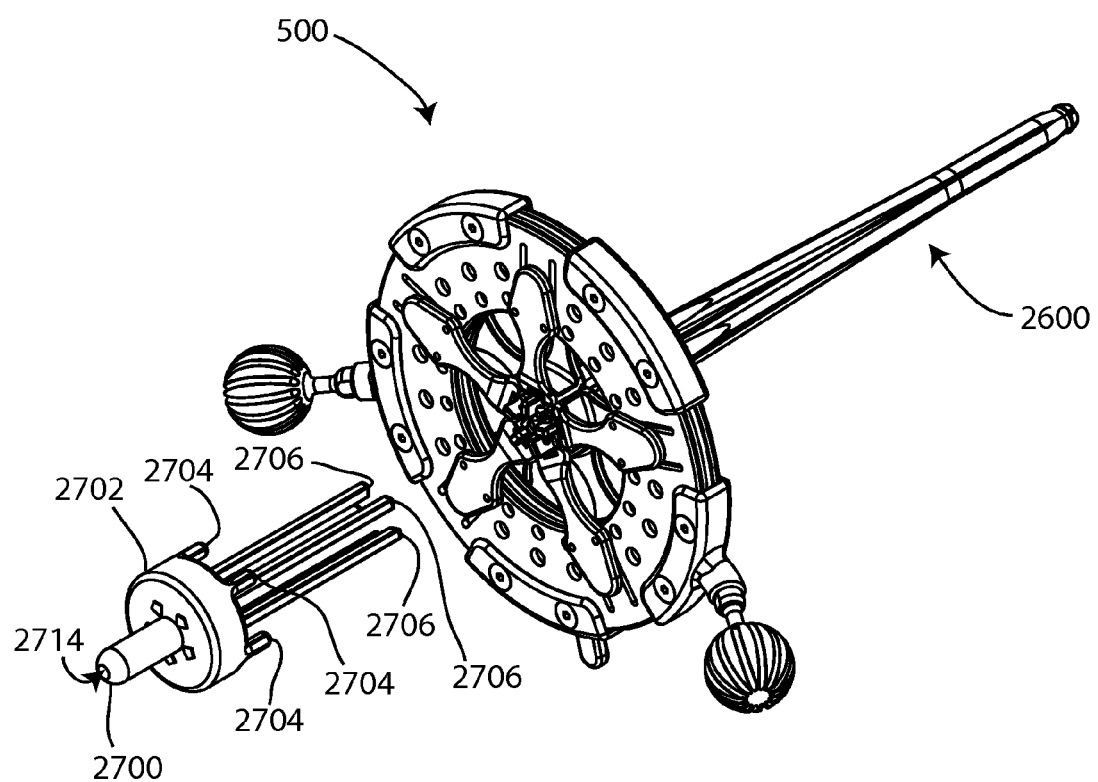
FIG. 47 is an exploded perspective view of the hub assembly, arm assemblies, and retainer of FIG. 46A.

FIGS. 45A-45B illustrate an arm retention clip 2400 which includes a body 2402, one or more short prongs 2404, one or more intermediate length prongs 2406, and a central shaft 2408, or stylus. The body may include a protrusion 2410 opposite the prongs 2404, 2406 and shaft 2408. Protrusion 2410 may serve as a handle. Shaft 2408 includes one or more laterally projecting tabs 2412 which may be positioned at a distance from the body 2402. Tabs 2412 may be sized and shaped, at least in cross section, to complement groove 2518 of arm 2500. Shaft 2408 may also include a through hole 2414, or cannulation, which may be sized to receive a guide wire, K-wire, Beath pin, stylus, or other small diameter shaft.

When clip 2400 is connected to hub assembly 500 and arm assemblies 2300, the central shaft 2408 is positioned in the middle of the pattern of arms 2500 (FIGS. 42B-42C), the prongs 2406 are positioned outside the pattern of arms 2500 and at least partially between adjacent arms 2500 (FIG. 42C), and the prongs 2404 are positioned where adjacent arm clamps 1200 touch (FIG. 42D). Furthermore, as may be appreciated from FIG. 42B, the tabs 2412 are positioned within the corresponding grooves 2518 so that the arms 2500 are supported against lateral bending and torsion deflection from within the pattern of arms. While groove 2518 and tab 2412 are shown with parallel sides, so that tab 2412 may slide laterally in and out of groove 2518, other shapes are contemplated. For example, groove 2518 and tab 2412 may have a dovetail shape so that tab 2412 may only slide in and out of groove 2518 in an axial direction. Groove 2518 and tab 2412 may be described as connecting features which cooperate to place the arms 2500 in a predetermined longitudinal alignment with the shaft 2408 when the connecting features are mutually engaged.

Referring to FIGS. 46-49, hub assembly 500 is shown operatively assembled to modified arm assemblies 2600 and an arm retention clip 2700. Compared to arm assembly 1300 of FIG. 24A, arm assembly 2600 has been modified to positively interact with arm retention clip 2700 to aid in holding the dilation device closed during insertion into tissue or a natural passageway. Arm retention clip 2700 may be connected to hub assembly 500 with arm assemblies 2600 before introducing the dilation device into tissue or a natural passageway, and may be removed after the dilation device is fully introduced.

Figures 48A, 48B:
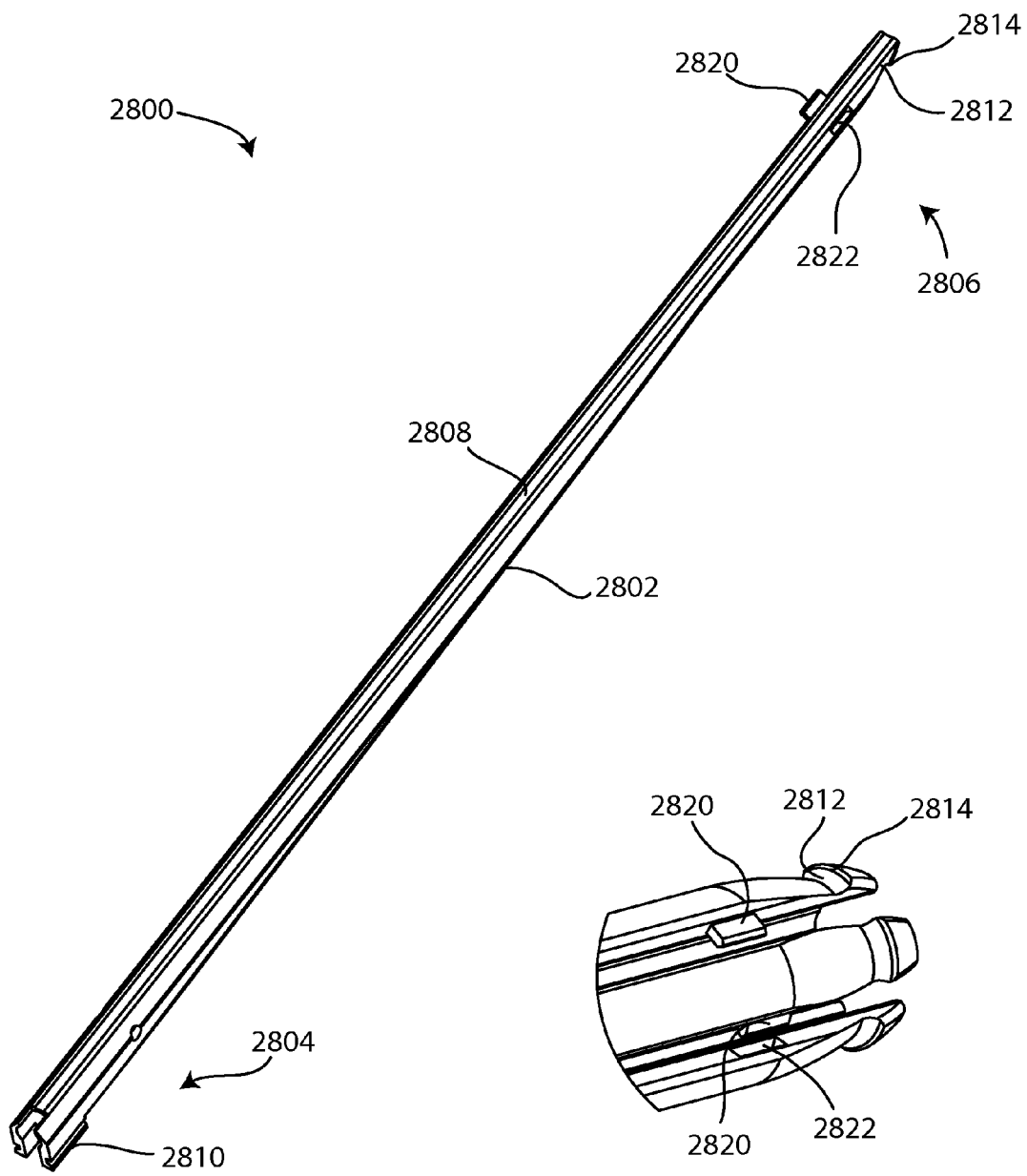
FIG. 48A is a perspective view of an arm of one of the arm assemblies of FIG. 46A.
FIG. 48B is an enlarged detail of a portion of the arm assemblies of FIG. 46A.

FIG. 48A illustrates an arm 2800, or blade, with an elongated shaft 2802 extending between a base 2804 and a tip 2806. Arm 2800 may share some or all of the characteristics of arm 1400 of FIG. 26. One side of arm 2800 has a full length groove 2808 or depression. The base 2804 includes a dovetail protrusion 2810 on a side opposite the groove 2808. The dovetail protrusion 2810 may be sized and shaped to complement dovetail slot 1206 of arm clamp 1200. The tip 2806 includes a waist 2812 and an adjacent flared portion 2814. Together, the waist 2812 and flared portion 2814 form a concavely curved area on the tip 2806, which may aid in holding back or retaining tissues dissected and pushed aside by the dilation device 400. A lateral side of the tip 2806 includes a protruding tab 2820. An opposite lateral side of the tip 2806 includes a recessed slot 2822 or socket. Slot 2822 is sized and positioned to receive a tab 2820 of an adjacent arm 2800, as may be appreciated in FIG. 48B, which shows an enlarged detail view of a pattern of arms 2800 in a partially open configuration. Tab 2820 and slot 2822 may be described as connecting features which cooperate to hold arms 2800 in a predetermined longitudinal alignment. Tab 2820 and slot 2822 may also be described as complementary engagement features which cooperate on adjacent arms to place the arms in contacting longitudinal alignment with one another along their lateral sides when the arms are in the closed configuration.

Figure 49:
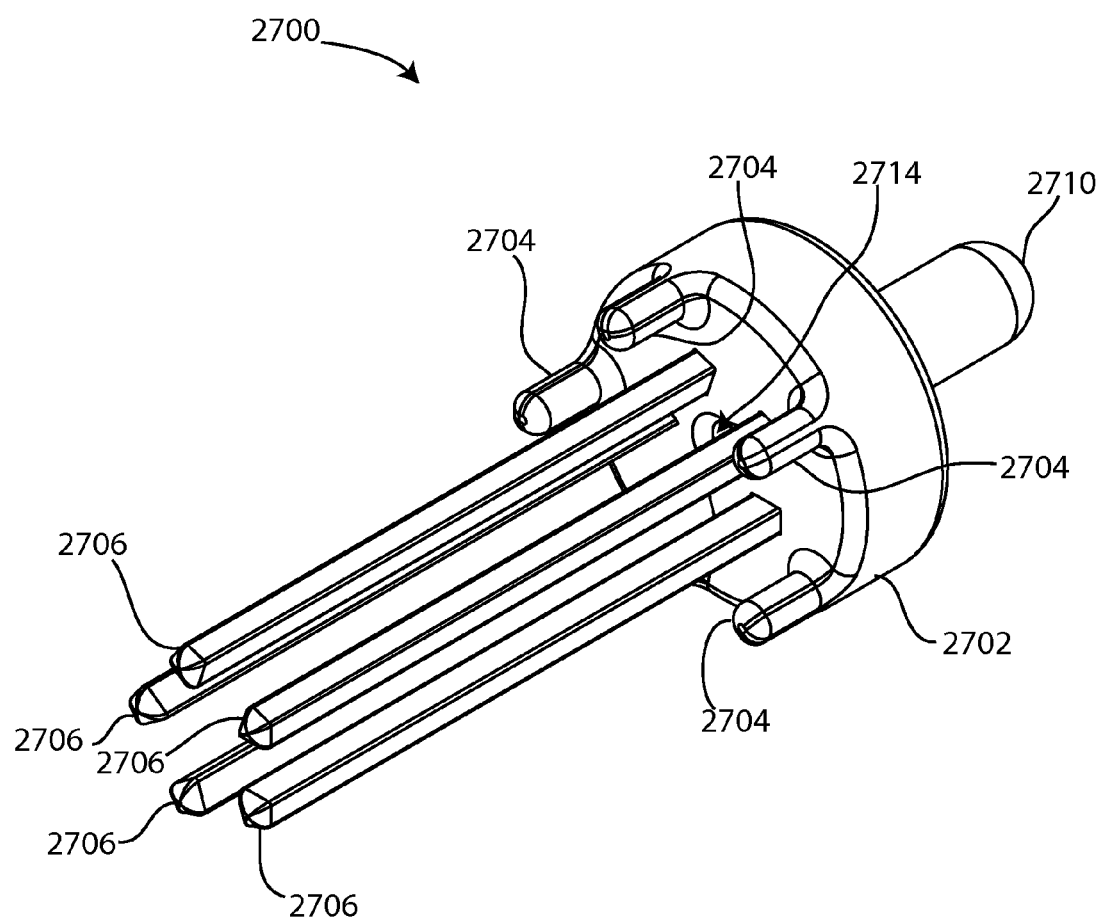
FIG. 49 is a perspective view of the retainer of FIG. 46A.

FIG. 49 illustrates an arm retention clip 2700 which includes a body 2702, one or more short prongs 2704, and one or more intermediate length prongs 2706. The body may include a protrusion 2710 opposite the prongs 2704, 2706. Protrusion 2710 may serve as a handle. Clip 2700 may also include a through hole 2714, or cannulation, which may be sized to receive a guide wire, K-wire, Beath pin, stylus, or other small diameter shaft.

When clip 2700 is connected to hub assembly 500 and arm assemblies 2600, the prongs 2706 are positioned outside the pattern of arms 2500 and at least partially between adjacent arms 2500 (FIG. 46C), and the prongs 2704 are positioned where adjacent arm clamps 1200 touch (FIG. 46D). Furthermore, as may be appreciated from FIG. 46B, the tabs 2820 are positioned within the corresponding slots 2822 so that the arms 2800 are self-supported against lateral bending and torsion deflection.

Figure 50:
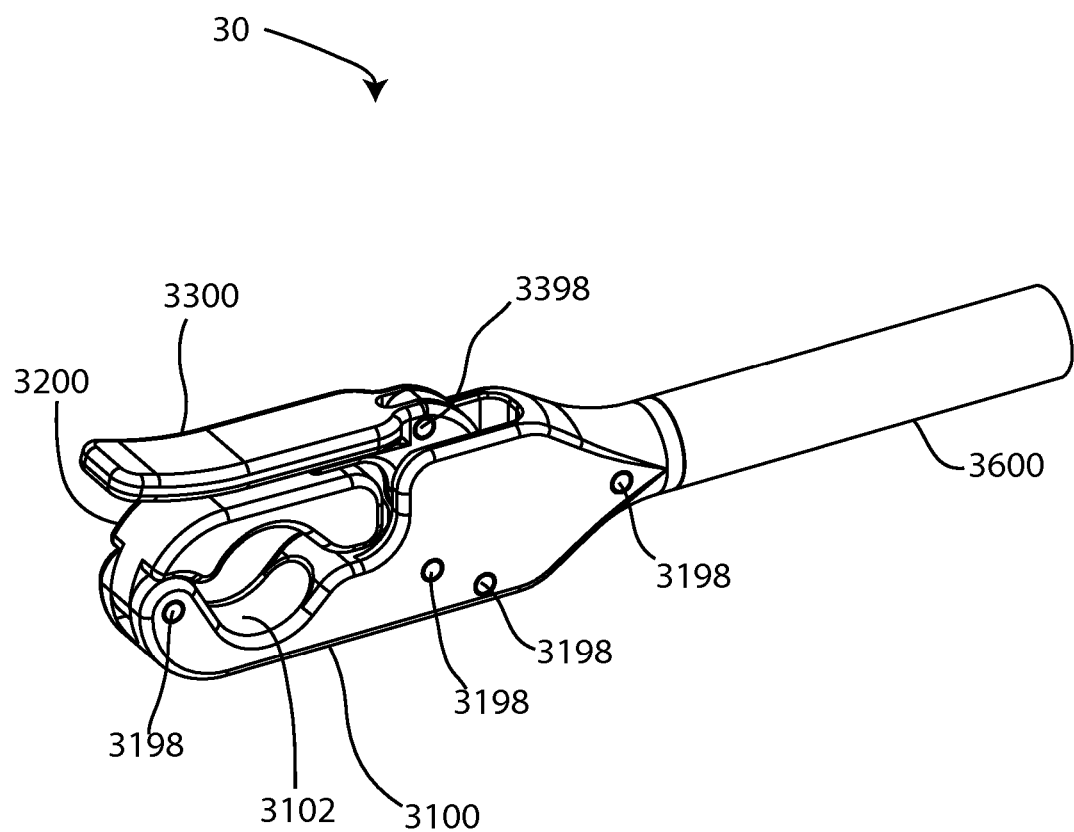
FIG. 50 is a perspective view of a clamp assembly in a closed configuration.
Figure 51:
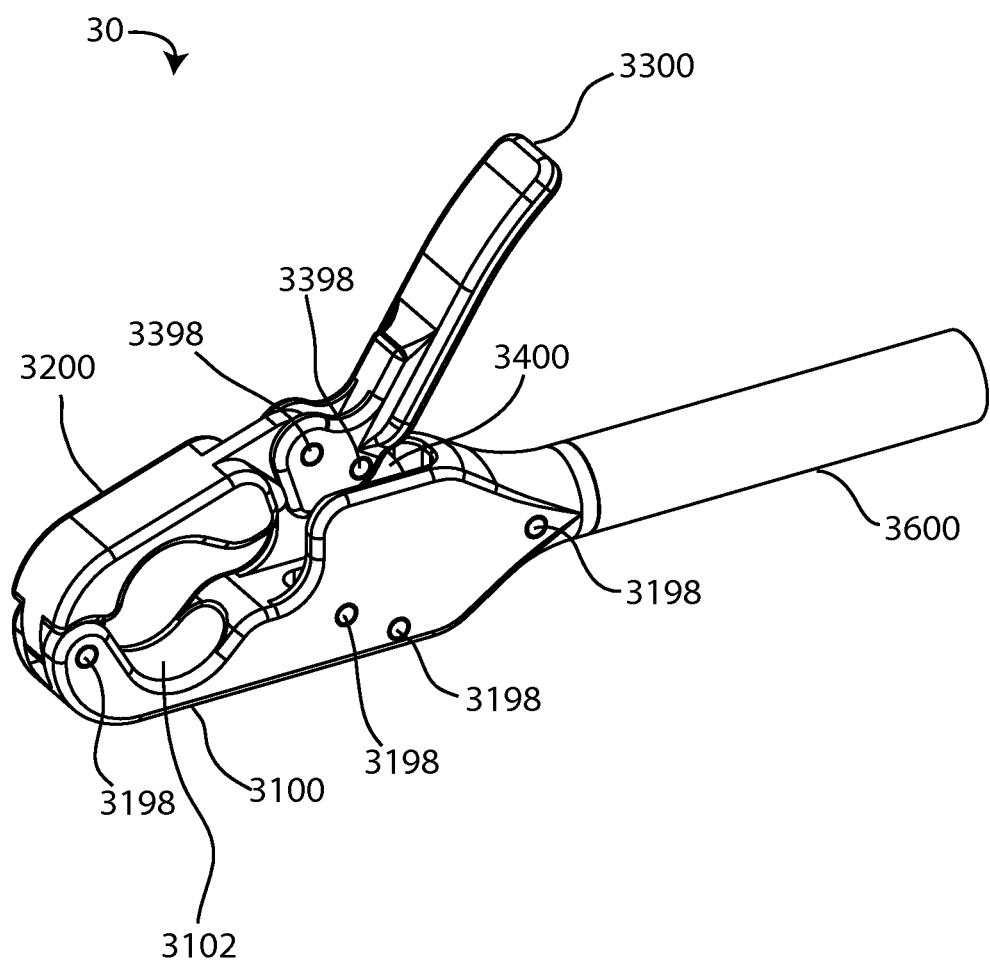
FIG. 51 is a perspective view of the clamp assembly of FIG. 50 in an open configuration.
Figure 52A:
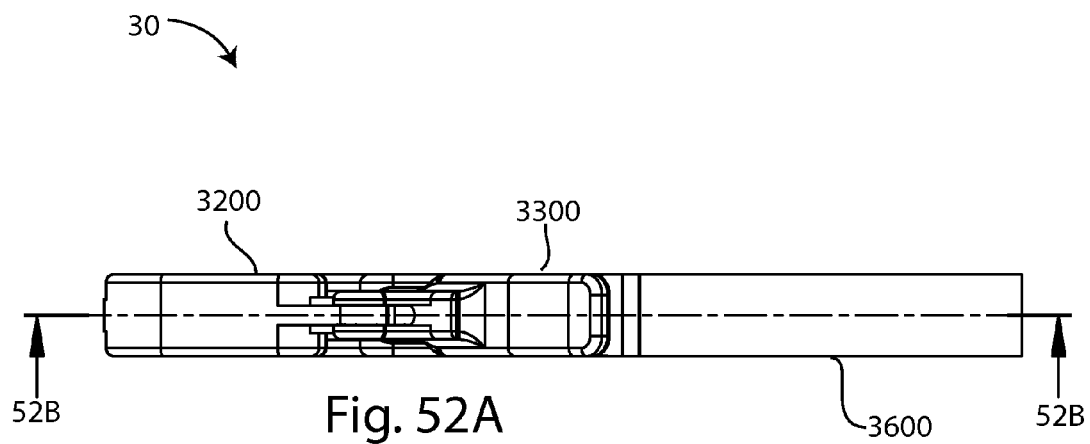
FIG. 52A is a side view of the clamp assembly of FIG. 50.
Figure 52B:
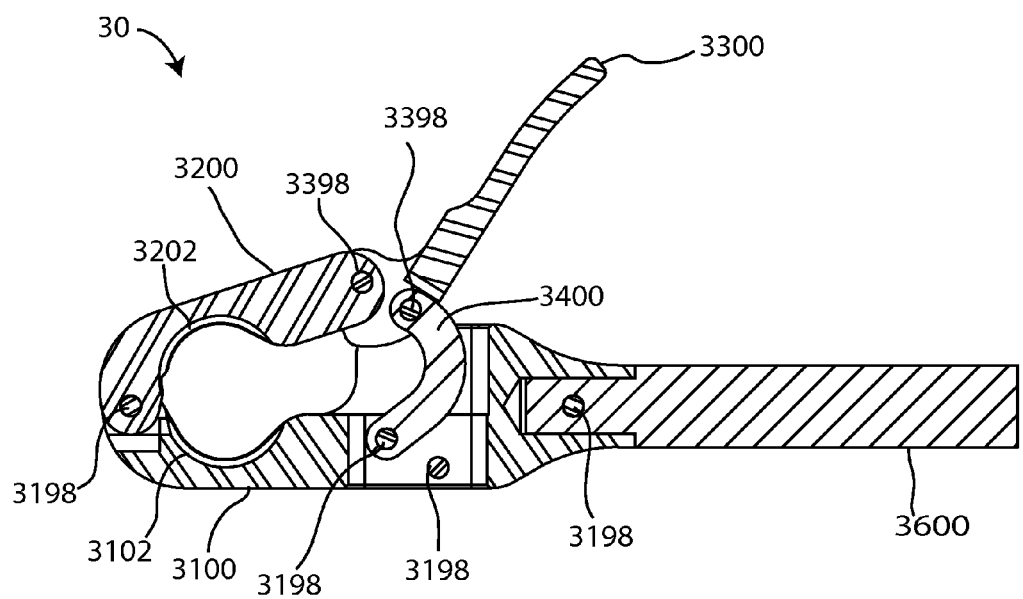
FIG. 52B is a cross section view of the clamp assembly of FIG. 50 taken along line 52B-52B of FIG. 52A.
Figure 53:
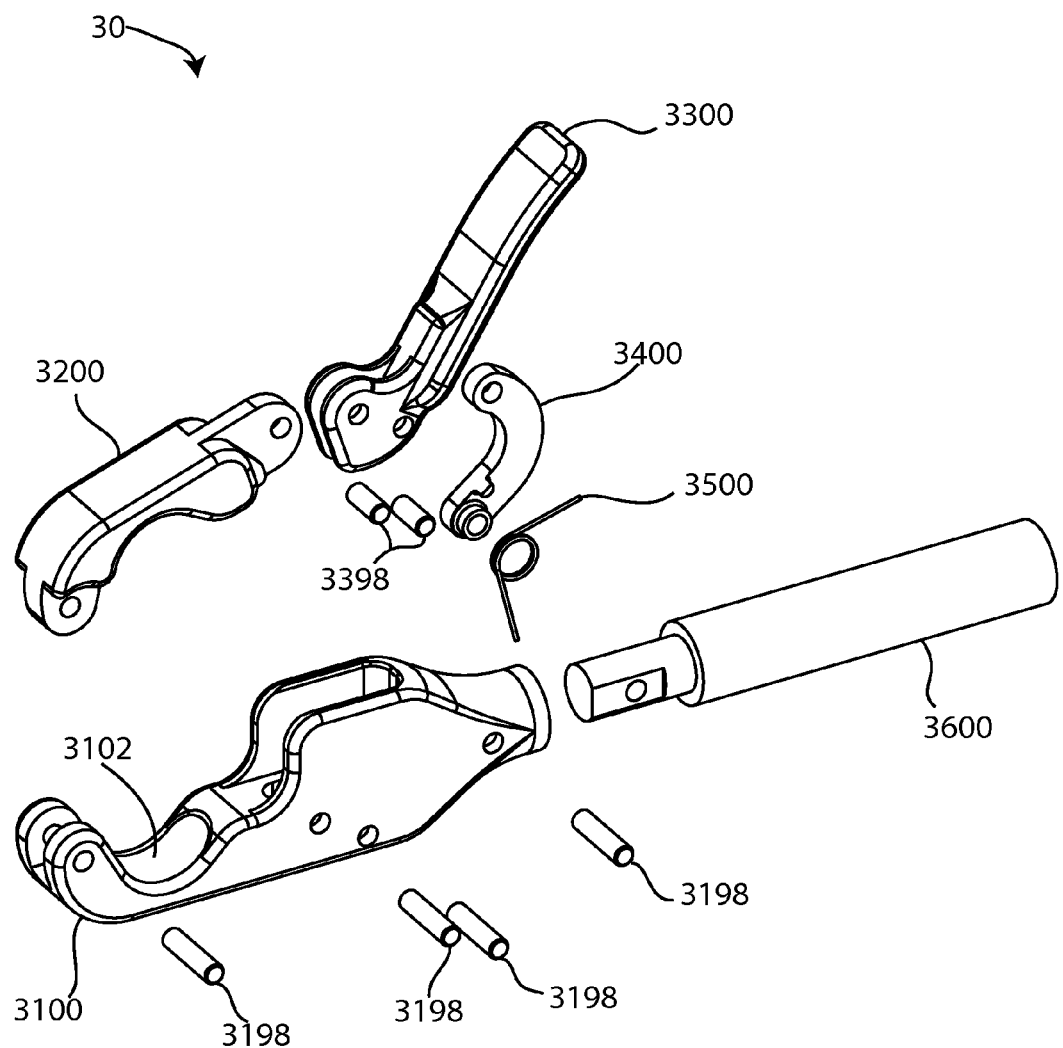
FIG. 53 is an exploded perspective view of the clamp assembly of FIG. 50.
Figure 54A:
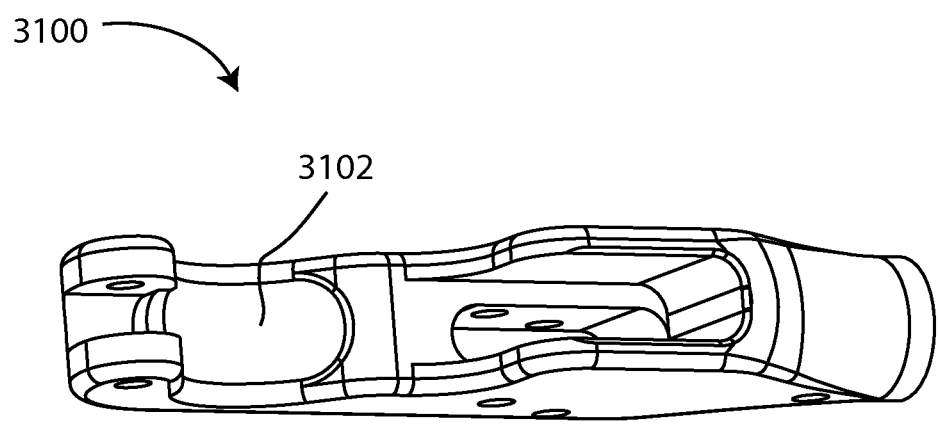
FIG. 54A is a perspective view of a stationary jaw of the clamp assembly of FIG. 50.
Figure 54B:
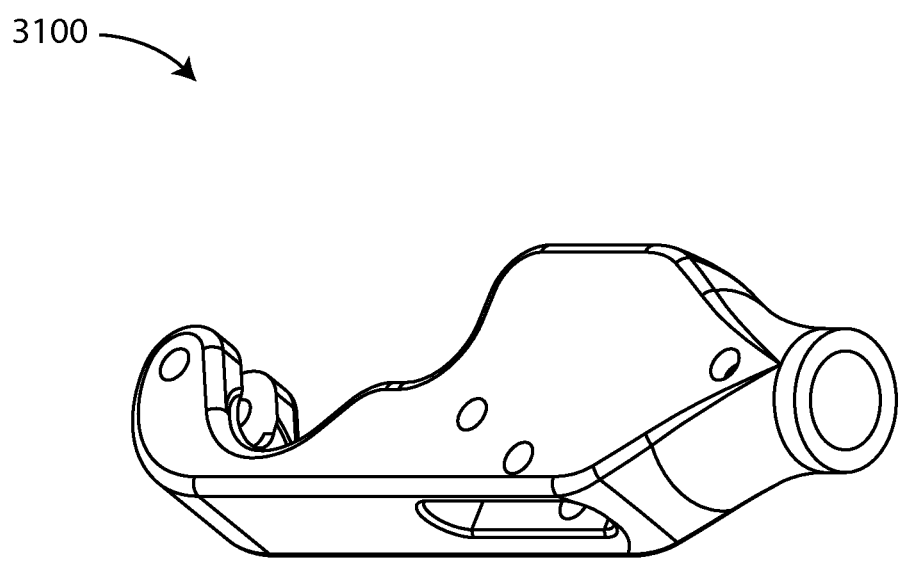
FIG. 54B is another perspective view of the stationary jaw of FIG. 54A from another direction.
Figure 55A:
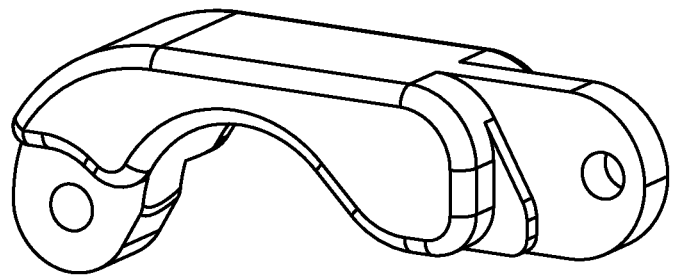
FIG. 55A is a perspective view of a movable jaw of the clamp assembly of FIG. 50.
Figure 55B:
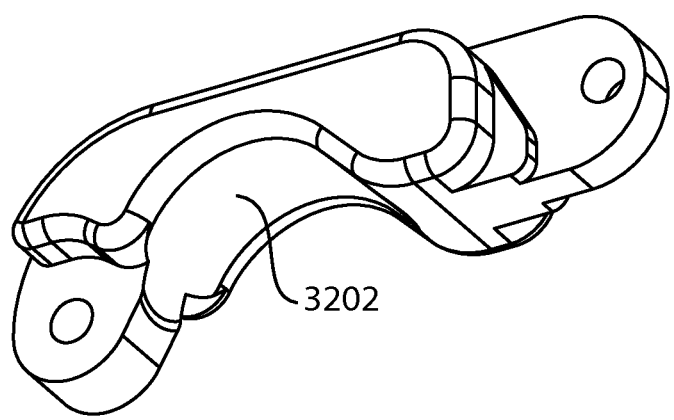
FIG. 55B is another perspective view of the movable jaw of FIG. 55A from another direction.

FIGS. 50-55B illustrate clamp 30 in greater detail. Clamp 30 may also be described as a clamp assembly since it includes several component parts in an operative arrangement. Clamp 30 includes a stationary jaw 3100, a movable jaw 3200, a lever 3300, a link 3400, an optional spring 3500, a shaft 3600, and fasteners 3198, 3398. FIG. 50 shows clamp 30 in a closed configuration. FIGS. 51-52B show clamp 30 in an open configuration. Clamp 30 may be designed to releasably lock onto spheres 36, 1102. For example, stationary jaw 3100 may include a partial spherical surface 3102 and movable jaw may include a partial spherical surface 3202. Surfaces 3102, 3202 may be sized to complement spheres 36, 1102. Surfaces 3102, 3202 may have non-spherical shapes, for example, conical or stepped cylindrical shapes. Surfaces 3102, 3202 may also include macro- or micro-texturing. Clamp 32 may share some or all of the characteristics of clamp 30.

Dilation devices 400, 1800, or hub assembly 500 with arm assemblies 2300 or 2600, may include one or more nerve retractor ports, which may be described as points of access in the device where a nerve retractor may be insinuated into the device to move a nerve out of the way.

Referring to FIGS. 56-61, methods of use will be described for dilation device 400. Similar methods of use may be applicable to dilation device 1800, or to hub assembly 500 in combination with arm assemblies 2300 or 2600.

Figure 56:
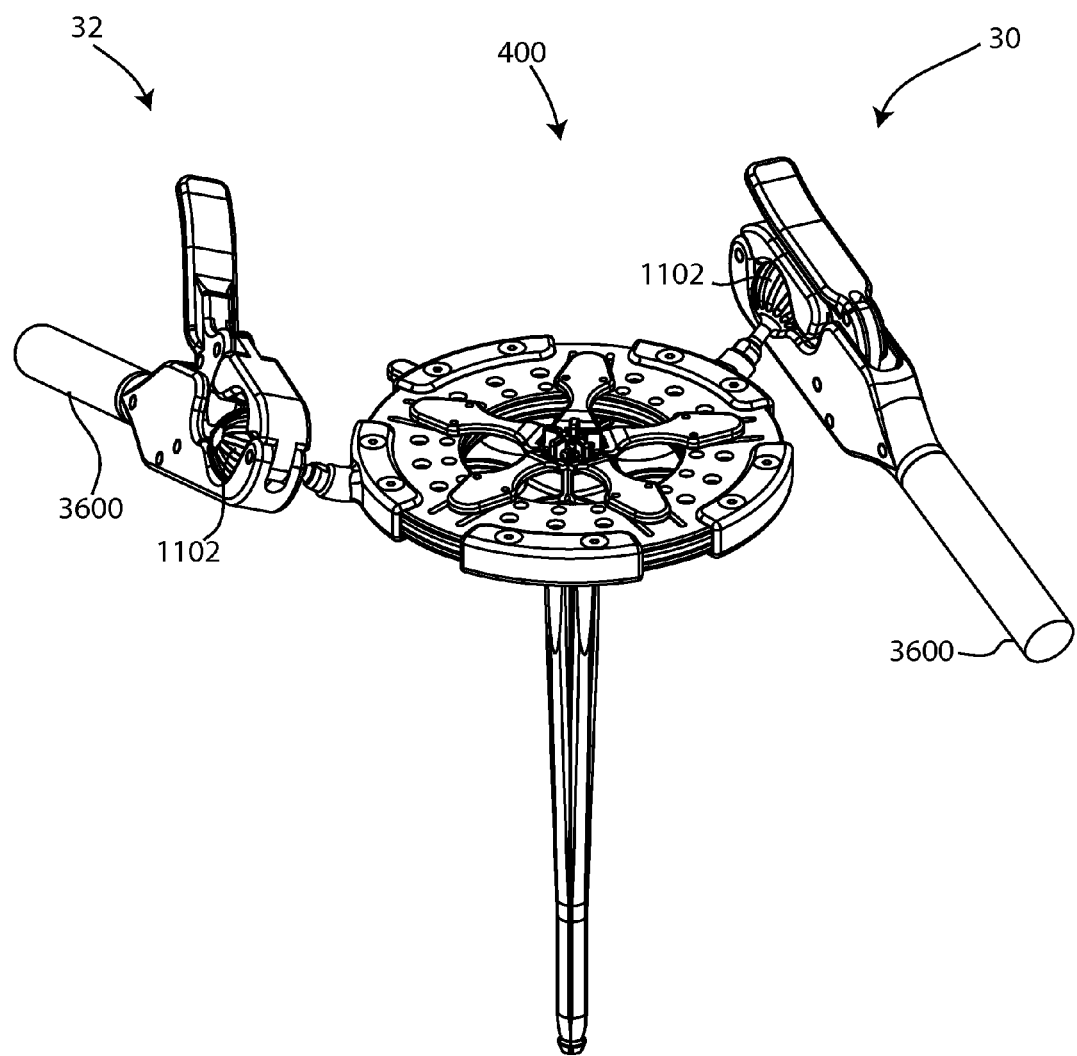
FIG. 56 is a perspective view of the tissue dilation device of FIG. 16 in a closed configuration, operatively assembled to a pair of the clamp assemblies of FIG. 50.

Referring to FIG. 56, dilation device 400 is shown in the closed configuration. Clamp 30 has been locked to a sphere 1102. Clamp 32 has been positioned on a sphere 1102, but is illustrated in the open configuration. The shafts 3600 of clamps 30, 32 may be locked to an external support (not shown), such as a surgical table mounted support system, which may provide stability and support to the hub and dilation device during surgical procedures Optionally, prior to inserting dilation device 400 through tissues or into a natural passageway, a stylus, guide wire, K-wire, Beath pin, or other small-diameter shaft or tube may be inserted through the tissues or passageway. The stylus tip position and shaft trajectory may be verified, for example, with imaging or other detection means to ensure the desired operative site is targeted. In this situation, dilation device 400 may be inserted over the stylus by sliding the stylus into a central space in the middle of the pattern of arms. Whether or not a stylus was used to locate the operative site and trajectory, an arm retention means may be employed during insertion of dilation device 400 or other dilation devices. For example, a retention band 64 may be applied around the waist 1418 of arms 1400. In another example, a dilation device may be introduced with an arm retention clip 2400 or 2700 connected to the device. In this situation, the retention clip 2400 or 2700 is removed after the dilation device is satisfactorily introduced. Some embodiments may include a lock or clip to immobilize the drive disk 700 with the dilation device 400 in the closed configuration, such as by interacting with the tab 710. Other embodiments may replace the manually operated tab 710 with a geared linkage which may make the dilation device 400 operate more smoothly.

Figure 57:
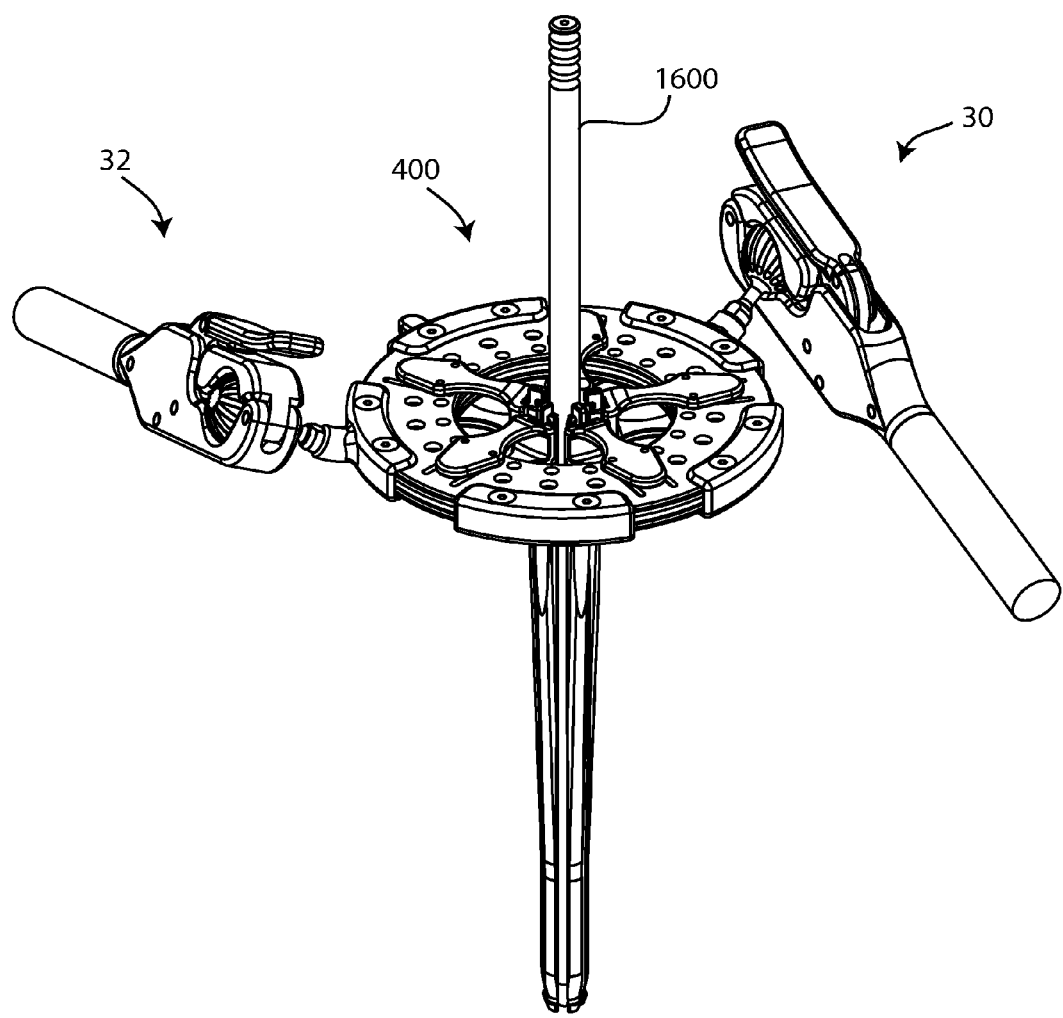
FIG. 57 is a perspective view of the tissue dilation device and clamp assemblies of FIG. 56, operatively assembled to the smallest one of the dilators of FIG. 28.

Referring to FIG. 57, dilation device 400 is shown with dilator 1600 inserted in the middle of the pattern of arms. The stylus, if used, is received in hole 1608 of dilator 1600. As the dilator 1600 is inserted into dilation device 400, the arms 1400 are pushed radially outward from the center of the pattern. The bases 1404 of the arms 1400 may be pushed radially outward before, or at the same time as, the tips 1406. In other words, the arms 1400 may be straight, or they may toe out or toe in. The surrounding tissue or passageway is pushed radially outward by the arms. No shearing, pulling, or dragging force is exerted on the tissue, at least in the direction of advancement of the dilator 1600. Thus, the potentially problematic effects of sequential dilation directly against tissue are avoided. Furthermore, since the dilator 1600 pushes against the arm assemblies 1300 instead of tissue, it may require significantly less effort, and therefore less time, to insert each dilator. Alternatively, dilation device 400 may be initially introduced with dilator 2200 inserted in the middle of the pattern of arms; an optional stylus may be used as well.

Figure 58:
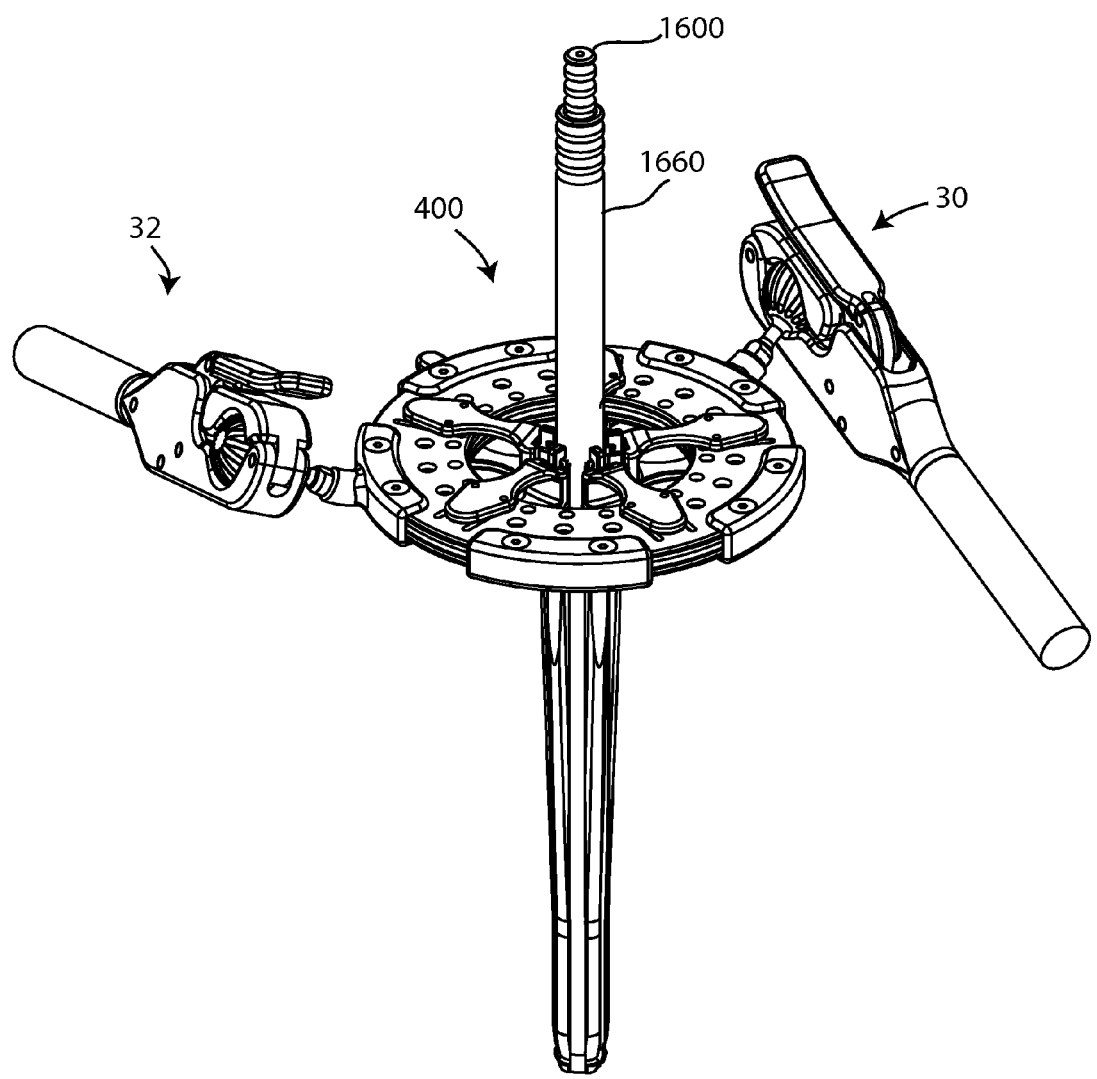
FIG. 58 is a perspective view of the tissue dilation device and clamp assemblies of FIG. 56, operatively assembled to the two smallest dilators of FIG. 28.

Referring to FIG. 58, dilation device 400 is shown after insertion of dilator 1660 over dilator 1600. As dilator 1660 is inserted into dilation device 400, the arms are pushed radially outward farther from the center of the pattern, and the surrounding tissue is urged radially outward as a result.

Additional dilators may be sequentially inserted into the dilation device 400 to increase the diameter of the working passageway. However, it may be possible to perform at least a portion of a surgical procedure through a relatively small-diameter cannula such as cannula 1700 in order to minimize insult to the surrounding tissues, at least by reducing the length of time those tissues are maximally dilated. Cannula 1700 may be introduced into the dilation device over dilator 1660, taking care to align the grooves 1714 with the lateral enlargements 1512. As cannula 1700 is inserted into dilation device 400, the arms are pushed radially outward farther from the center of the pattern, and the surrounding tissue is urged radially outward as a result. Thus cannula 1700 may function as a dilator. After cannula 1700 is inserted, it is prevented from expulsion by the action of the lateral enlargements 1512 in the windows 1716. Cannula 1700 may be further stabilized by inserting fasteners 1798 through holes 1710 and into the structures surrounding the operative site. Fasteners 1798 may be hex-headed tip-threaded pins, as shown, which may thread into bone. After cannula 1700 is adequately stabilized, the stylus (if used) and dilators 1600, 1660 may be removed to open up the interior of the cannula 1700 for the passage of instruments or implants.

Figure 59:
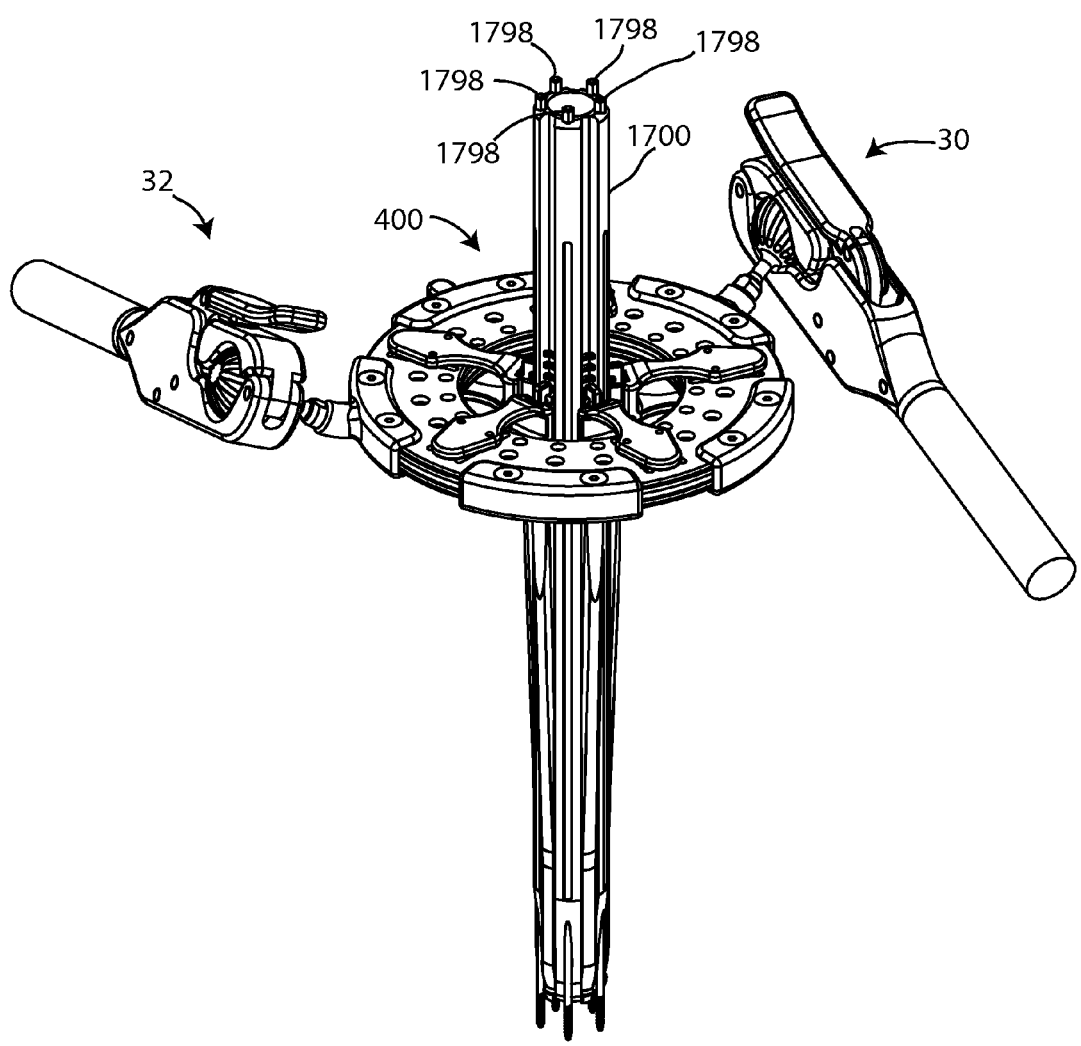
FIG. 59 is a perspective view of the tissue dilation device and clamp assemblies of FIG. 56, operatively assembled to the smallest one of the cannulas of FIG. 29 and a plurality of long pins.

Referring to FIG. 59, dilation device 400 is shown with cannula 1700 inserted in the middle of the pattern of arms and fixed in place with pins 1798. Cannula 1700 may provide an adequate working space for instruments or implants. For example, cannula 1700 may be an appropriate size for the passage of minimally invasive discectomy instruments. Alternatively, dilator 1660 may function as a cannula.

Dilator 1670 may be inserted over cannula 1700 to further dilate the tissues. As dilator 1670 is introduced between cannula 1700 and the arm assemblies 1300, the lateral enlargements 1512 may be automatically pushed out of the windows 1716, disengaging the cannula 1700 from the dilation device 400. Should even more dilation be required, dilators 1680, 1690 may be used sequentially over dilator 1670.

Figure 60:
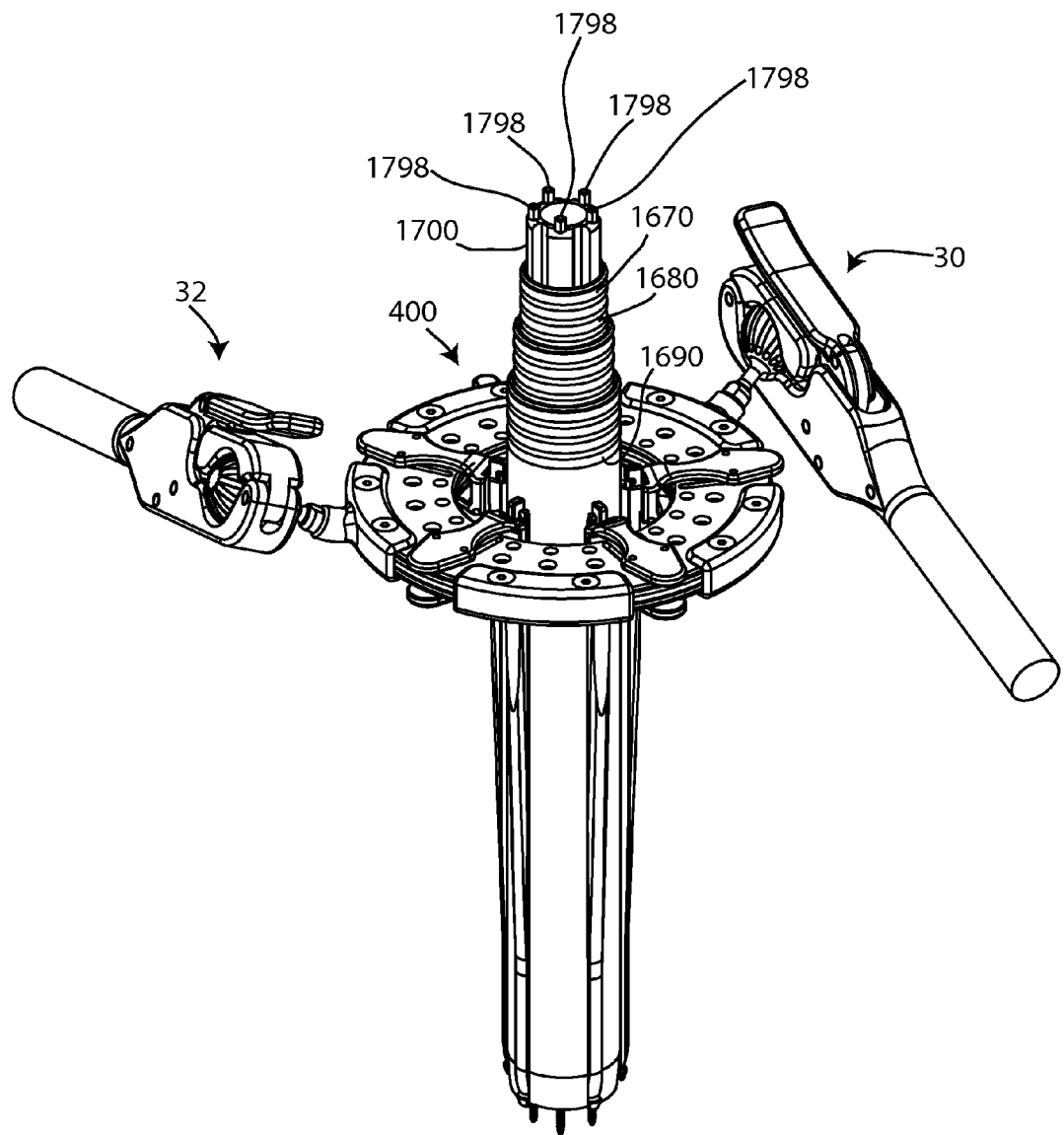
FIG. 60 is a perspective view of the tissue dilation device, clamp assemblies, cannula, and pins of FIG. 59, operatively assembled to the three largest dilators of FIG. 28.

Referring to FIG. 60, dilation device 400 is shown with cannula 1700 still fixed in place with pins 1798, and with dilators 1670, 1680, 1690 nested over cannula 1700.

Cannula 1790 may be introduced into the dilation device over dilator 1690, taking care to align the cannula grooves 1714 with the lateral enlargements 1512. As cannula 1790 is introduced into the dilation device 400, the arms are pushed farther laterally. Thus cannula 1790 may function as a dilator. After cannula 1790 is inserted, it is prevented from expulsion by the action of the lateral enlargements 1512 in the windows 1716. Cannula 1790 may be further stabilized by inserting fasteners 1798 through holes 1710 and into the structures surrounding the operative site. After cannula 1790 is adequately stabilized, the cannula 1700 and dilators 1660, 1670, 1680 may be removed to open up the interior of the cannula 1790 for the passage of instruments or implants. Alternatively, cannula 1770 may be introduced after dilator 1670, or cannula 1780 may be introduced after dilator 1680. In still other alternatives, dilators 1670, 1680, 1690 may function as cannulas.

Figure 61:
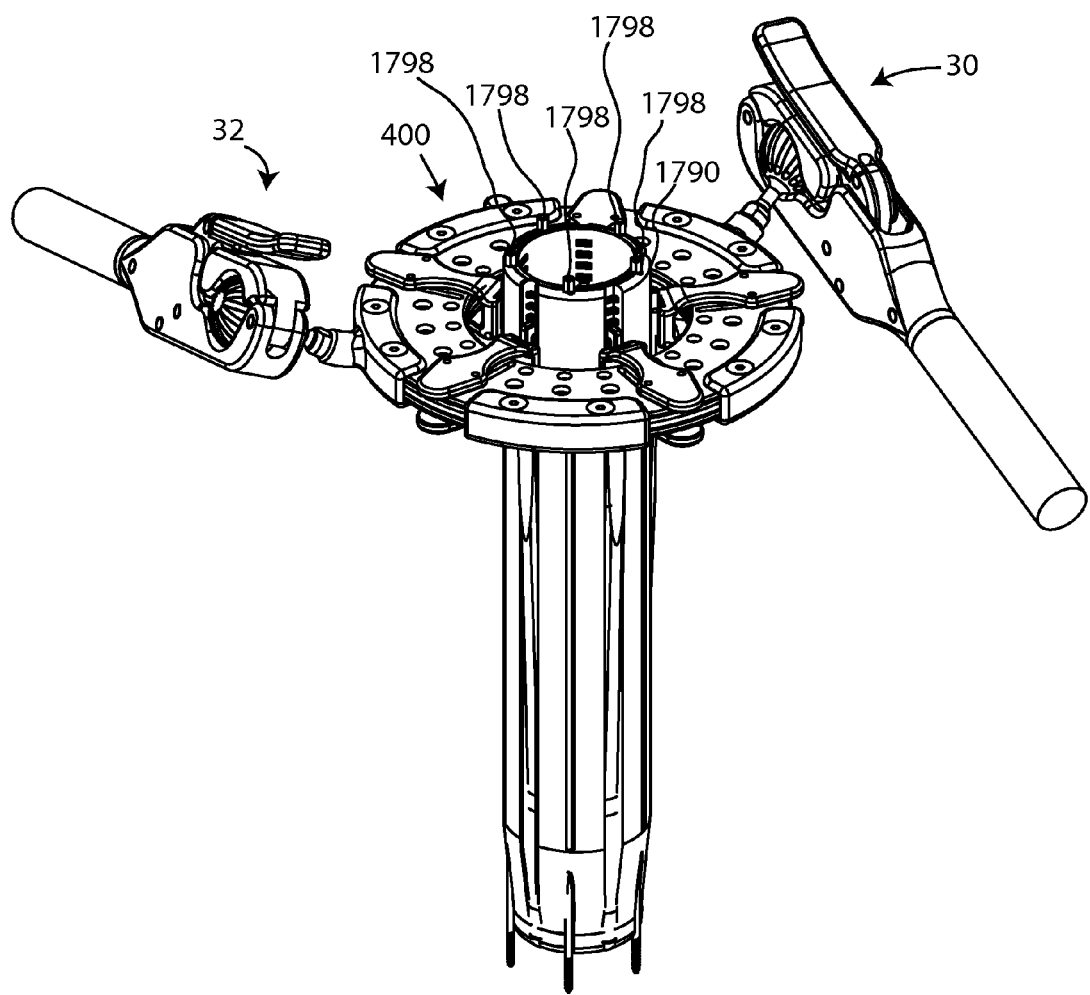
FIG. 61 is a perspective view of the tissue dilation device and clamp assemblies of FIG. 56, operatively assembled to the largest one of the cannulas of FIG. 29 and a plurality of long pins.

Referring to FIG. 61, dilation device 400 is shown with cannula 1790 inserted in the middle of the pattern of arms and fixed in place with pins 1798. Cannula 1790 may provide an adequate working space for instruments or implants. For example, cannula 1790 may be an appropriate size for the passage of a spinal implant, such as a total disc implant or fusion cage.

FIGS. 62-67 illustrate steps in a method of use for dilation device 400 in the spine. Similar methods of use may be applicable to dilation device 1800, or to hub assembly 500 in combination with arm assemblies 2300 or 2600.

Figure 62:
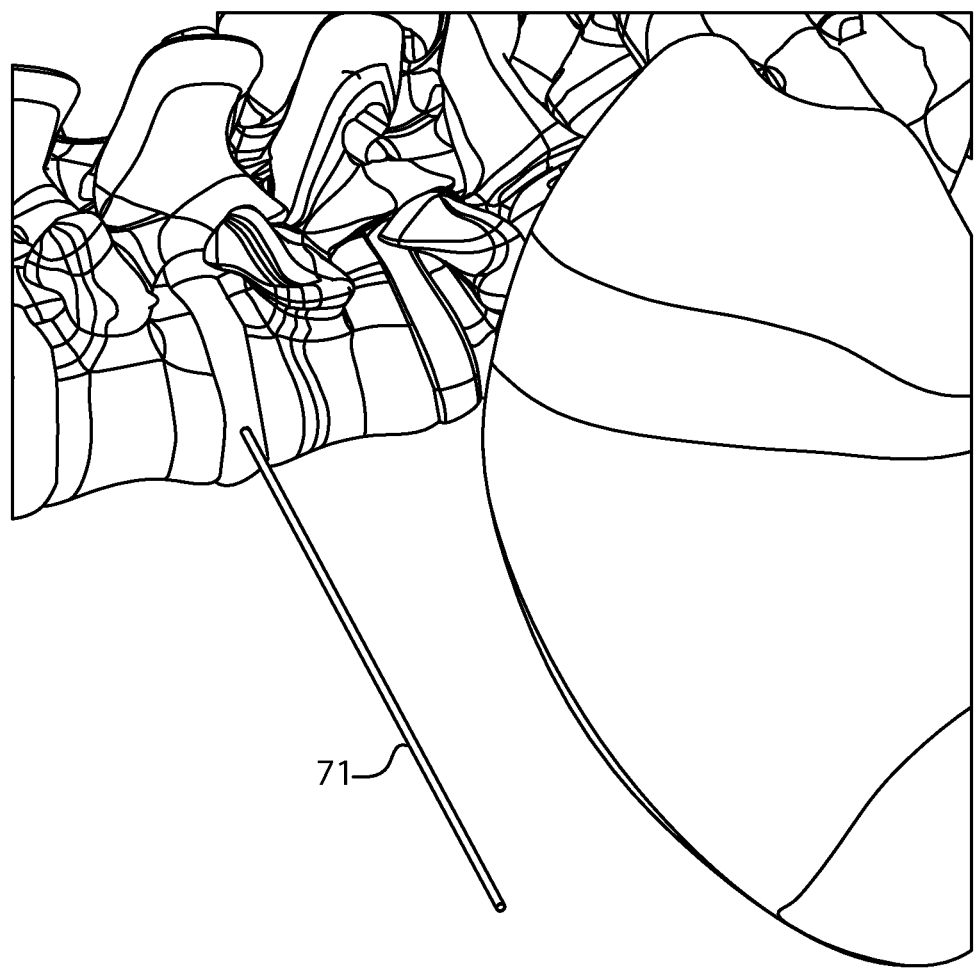
FIG. 62 is a perspective view of a portion of a stylized human lumbar spine and pelvis, with a stylus positioned and oriented for a direct lateral approach to an intervertebral disc.
Figure 63:
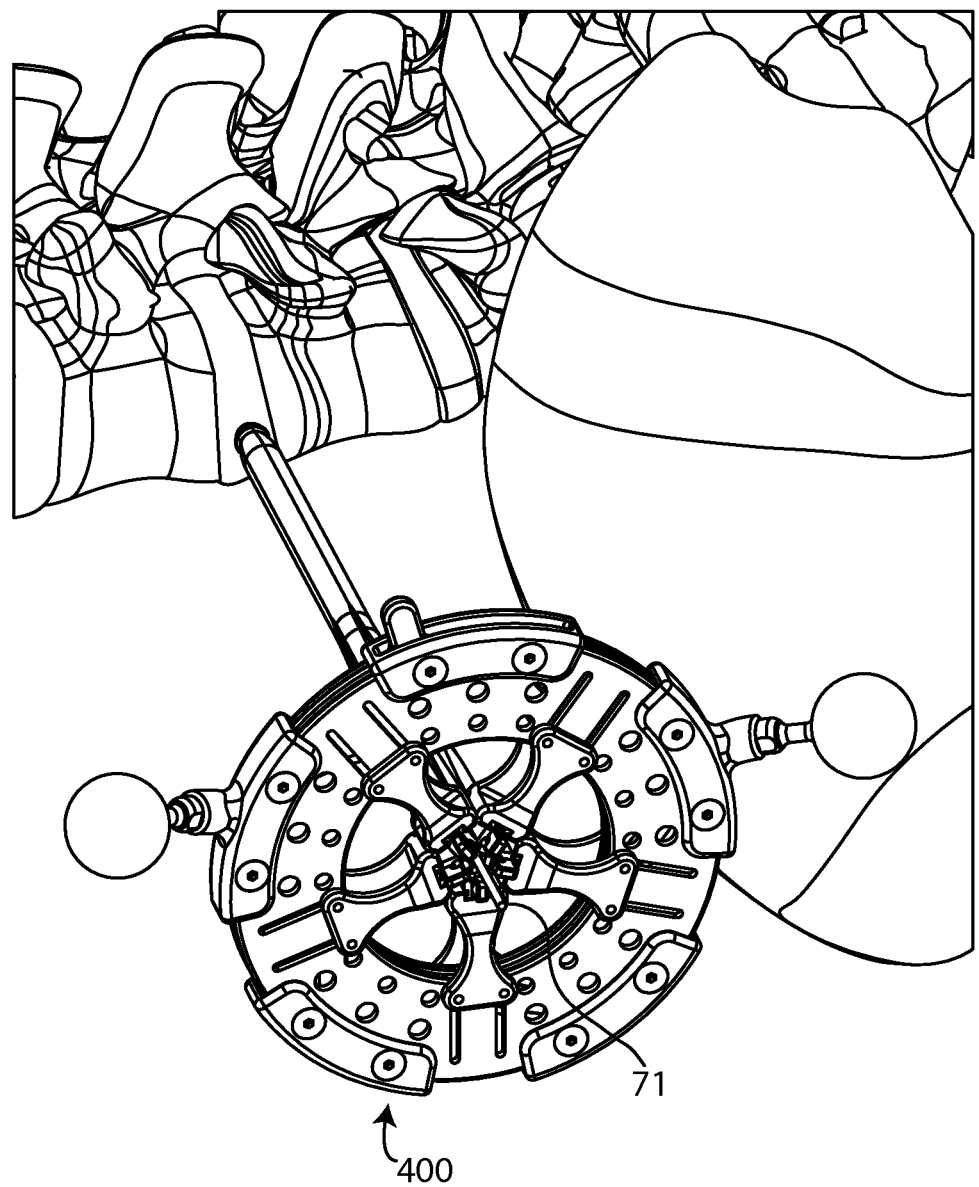
FIG. 63 is a perspective view of the spine, pelvis, and stylus of FIG. 62, operatively assembled to the tissue dilation device of FIG. 16.

In FIG. 62, a stylus 71 has been introduced to a lumbar intervertebral disc through a direct lateral approach. In FIG.

Figure 64:
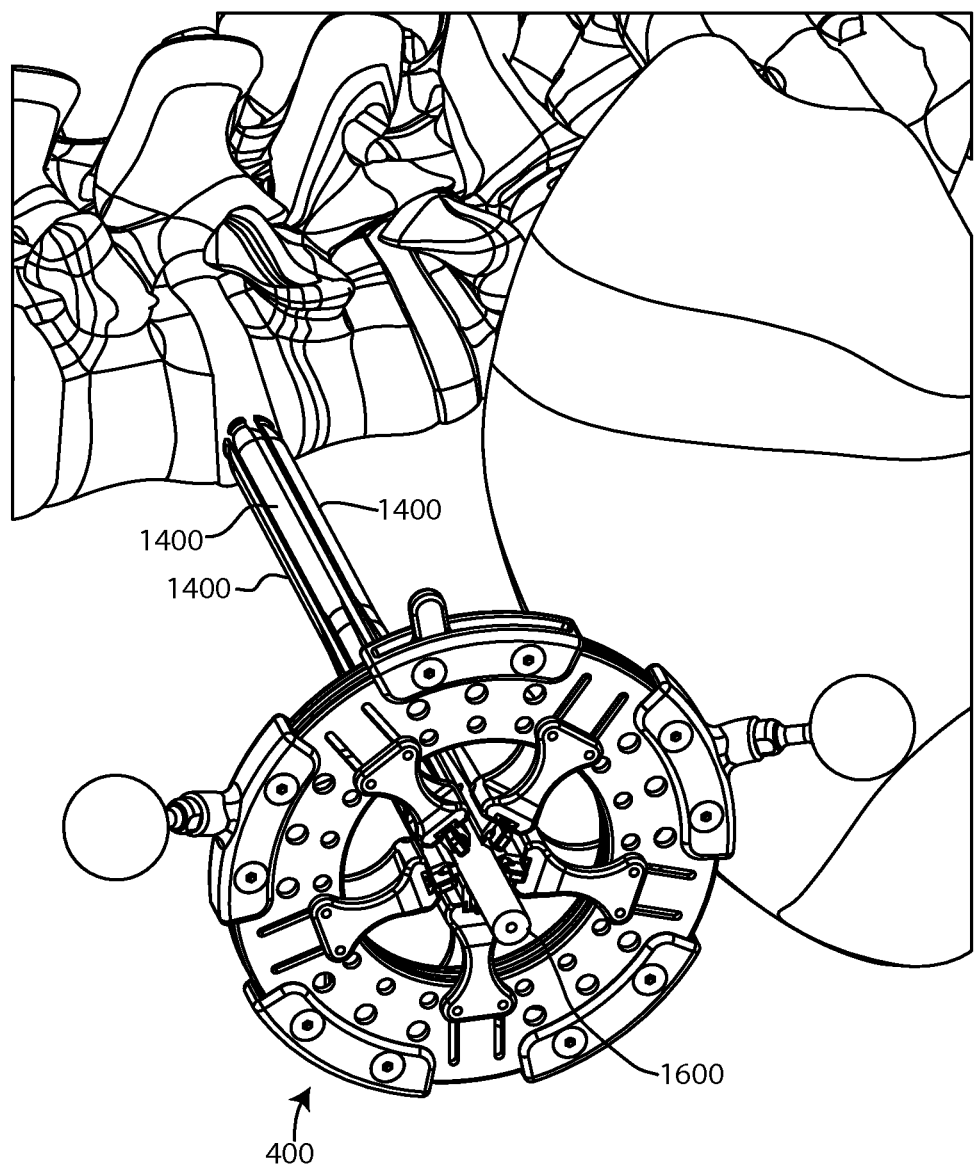
FIG. 64 is a perspective view of the spine, pelvis, stylus, and tissue dilation device of FIG. 63, operatively assembled to the smallest dilator of FIG. 28.
Figure 65:
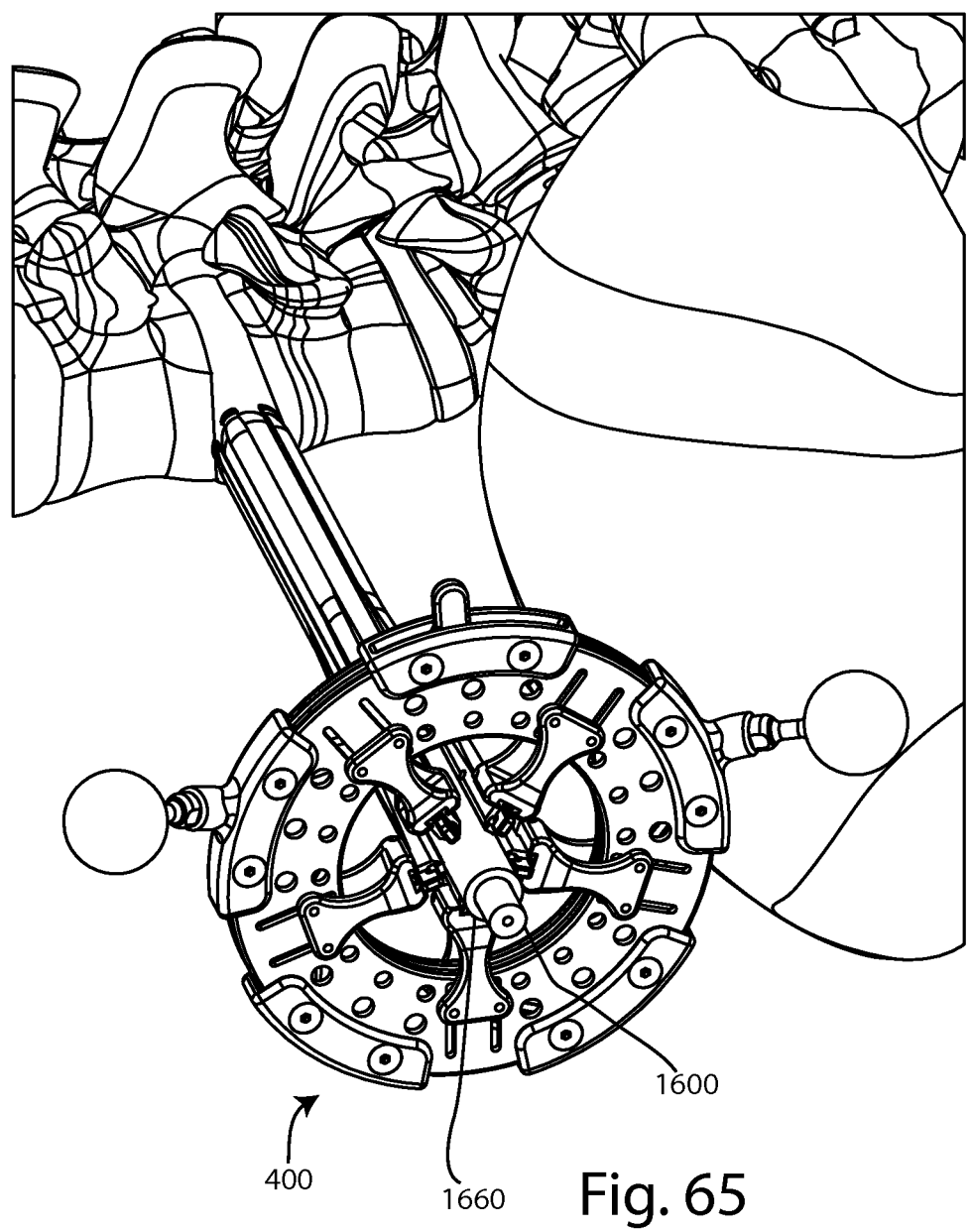
FIG. 65 is a perspective view of the spine, pelvis, stylus, and tissue dilation device of FIG. 63, operatively assembled to the two smallest dilators of FIG. 28.
Figure 66:
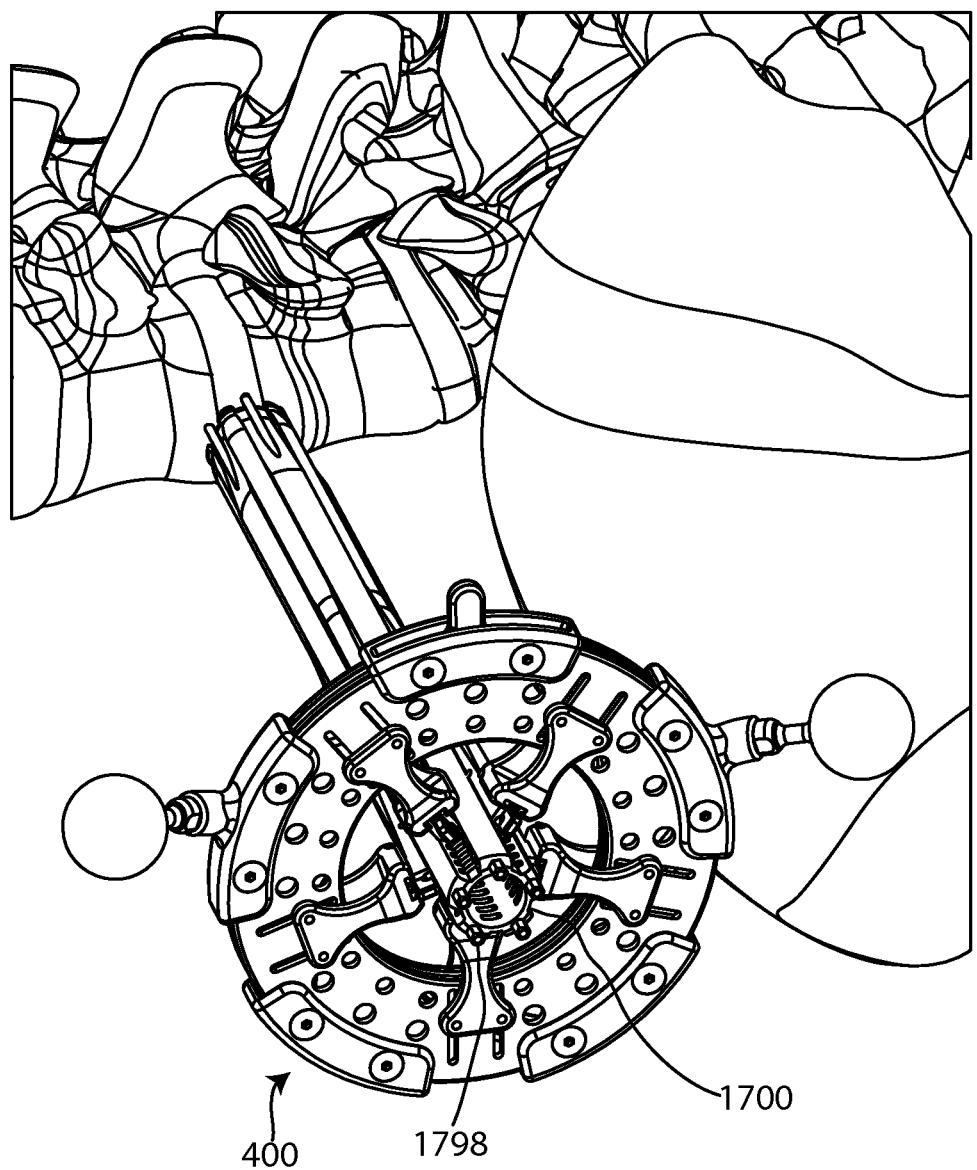
FIG. 66 is a perspective view of the spine, pelvis, and tissue dilation device of FIG. 63, operatively assembled to the smallest cannula of FIG. 29 and a plurality of long pins.
Figure 67:
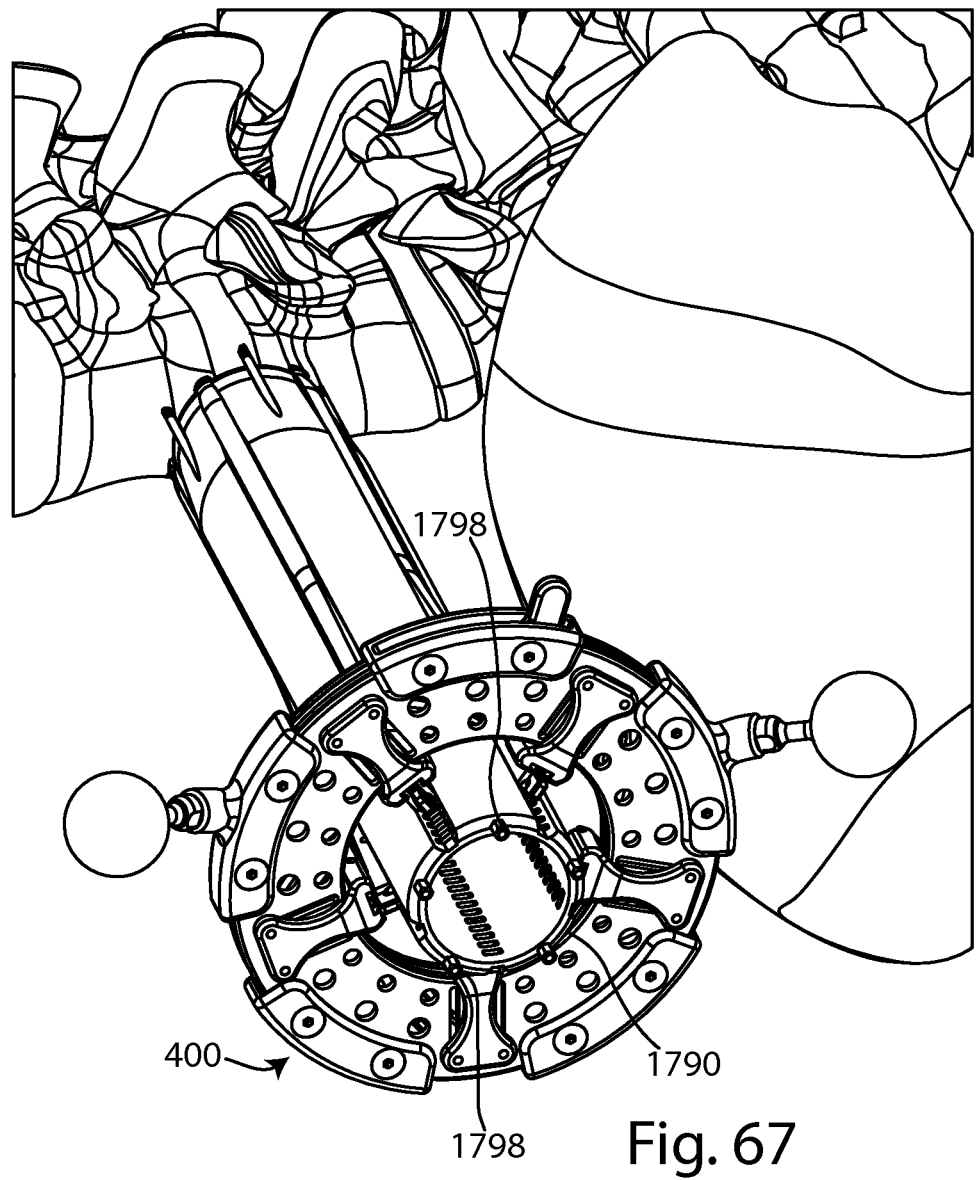
FIG. 67 is a perspective view of the spine, pelvis, and tissue dilation device of FIG. 63, operatively assembled to the largest cannula of FIG. 29 and a plurality of long pins.

63, a dilation device 400 has been introduced over the stylus 71. Dilation device 400 may be stabilized with clamps 30, 32 (not shown). Alternatively, the circular nature of the hub assembly 500 of dilation device 400 provides opportunities for it to be used in the practice of targeting the initial stylus to the intervertebral space. In FIG. 64, dilator 1600 has been introduced over stylus 71 and within the pattern of arms 1400. In FIG. 65, dilator 1660 has been introduced over dilator 1600. In FIG. 66, cannula 1700 has been introduced and stabilized with fasteners 1798, and stylus 71 and dilators 1600, 1660 have been removed. A discectomy procedure may be performed with minimally invasive instruments working through cannula 1700. In FIG. 67, cannula 1790 has been introduced and stabilized with fasteners 1798, and cannula 1700 and dilators 1670, 1680, 1690 have been removed. A spinal implant may be inserted with minimally invasive instruments working through cannula 1790. At the conclusion of the surgical procedure, cannula 1790 may be released from dilation device 400 by moving tab 710 sideways to expand the pattern of arms, thus disengaging lateral enlargements 1512 from windows 1716.

One way to view the teachings set forth above is to characterize certain structures as connecting means for placing each arm in a predetermined longitudinal alignment with the stylus. In the various embodiments set forth above the connecting means can be said to be elements 79 and 97 as shown in FIGS. 4A, 5A and 5B; elements 182 and 204 as shown in FIGS. 8 and 9; elements 1400 and 2210 as shown in FIGS. 38-40B; elements 2518 and 2412 as shown in FIGS. 41A-45B; and elements 2820, 2822, and 2700 as shown in FIGS. 46A-49. Other connecting means are contemplated, including but not limited to pegs and corresponding holes which are round, oval, rectangular, or multi-sided; or other complementary protrusion and slot combinations. The receiving hole may be open on both ends or may be a recess or cavity with an opening on one side shaped to receive the peg. In an alternative embodiment, the pegs may be located on the arms, and the receiving hole or cavity on the stylus or stylus tip.

Certain aspects of the teaching set forth above can be characterized as lateral engagement means for placing the arms in contacting longitudinal alignment with one another along their first and second lateral edges. The structure for the lateral engagement means is found in FIGS. 5C and 5D in elements 108; in FIGS. 7-9 in elements 216, 218, 224 and 226; in FIGS. 41A-45B in elements 2518 and 2412; and in FIGS. 46A-49 in elements 2820, 2822, and 2700. Other lateral engagement means are contemplated, including but not limited to tongue-in-groove features, corresponding tab and slot features, or press-fit features. Such features may be disengaged by removal of a pin, suture or wire such as release wire 226, or may have a friction fit in which the features are detached from one another by sufficient expansive force provided by expansion of the dilating member.

Some aspects of the teaching set forth above can be characterized as a means for dilation. In the various embodiments set forth above the means for dilation can be said to be element 110 in FIGS. 3, 4A, and 4B; elements 240 and 242 in FIGS. 8-11; element 300 in FIGS. 14 and 15; elements 1600, 1660, 1670, 1680, and 1690 in FIG. 28; elements 1700, 1770, 1780, and 1790 in FIG. 29; and element 2100 in FIGS. 37A-37B. Other dilation means contemplated include expansion instruments such as retractors and other mechanical expanders.

Some aspects of the teaching set forth above can be characterized as a means for circumferentially surrounding at least a portion of the dilating member. In the various embodiments set forth above the means for circumferentially surrounding at least a portion of the dilating member can be said to be elements 130 and 140 in FIGS. 1-4B and FIGS. 6A-6B, element 246 in FIG. 11, element 290 in FIGS. 12-14, element 1400 in FIG. 26, element 2500 in FIG. 44, and element 2800 in FIG. 48A.

The present invention may be embodied in other specific forms without departing from its spirit or essential characteristics. It is appreciated that various features of the above-described examples can be mixed and matched to form a variety of other alternatives. For example, the dilating member may comprise a balloon, and/or a cannula. Embodiments may variously include connecting features between the stylus and the plurality of arms, and engagement features between individual arms. It is also appreciated that this system is not limited to creating a passage through a muscle; it may be used to create a passage through any soft tissues, or to dilate and hold open a naturally occurring passage. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A system for opening a passageway in a mammalian body, wherein the system comprises:
   a dilation device comprising a plurality of arms arranged in a pattern,
   a stationary disk defining a plurality of slots;
   a drive disk stacked with the stationary disk, wherein the drive disk defines a plurality of slots, wherein the drive disk is configured to at least partially rotate about a longitudinal axis passing through a center of the pattern;
   a plurality of arm clamps, wherein,
      each arm is engaged with one of the arm clamps;
      each arm clamp defines at least one channel configured to receive at least the stationary disk and the drive disk; and
      each arm clamp along with the arm is radially movable relative to the center of the pattern along the slots defined in the stationary disk and the drive disk; and
   a retention element connectable to the dilation device, wherein the plurality of arms of the dilation device are held in a closed configuration when the retention element is connected to the dilation device, said retention element comprising a plurality of prongs configured to extend through the drive disk and to interact with the plurality of arms to retain the arms in a closed configuration during introduction of the dilation device into the body;
   wherein the dilation device transforms from a closed configuration to an open configuration in response to movement of the arm clamps away from the center, wherein the arms are in contacting longitudinal alignment and close to the center of the pattern in the closed configuration, wherein the arms are separated and far from the center of the pattern in the open configuration.

2. The system of claim 1, further comprising dilator, wherein the dilator is insertable in the middle of the pattern of arms, wherein the insertion of the dilator pushes the arms radially away from the center of the pattern.

3. The system of claim 2, wherein the system comprises:
   a cannula, wherein the cannula comprises an inside diameter;
   wherein the dilator comprises an outside diameter, wherein the outside diameter is smaller than the inside diameter of the cannula; and wherein the cannula is insertable in the middle of the pattern of arms over the dilator.

4. The system of claim 3, wherein the system comprises:
a plurality of nesting dilators; and
a plurality of cannulas;
wherein each cannula is insertable in the middle of the pattern of arms over a corresponding one of the dilators.

5. The system of claim 3, wherein the dilation device comprises a lock, wherein the lock automatically permits the cannula to move in the insertion direction and automatically prevents the cannula from moving in the removal direction.

6. The system of claim 5, wherein moving the arms radially farther from the center of the pattern releases the lock to permit the cannula to move in the removal direction.

7. The system of claim 1,
wherein the dilation device is transformable from the closed configuration to the open configuration when the retention element is disconnected from the dilation device.

8. The system of claim 7, wherein the retention element at least partially encircles the arms when the retention element is connected to the dilation device.

9. The system of claim 8, wherein the prongs are positioned outside the pattern of arms when the retention element is connected to the dilation device, wherein the retention element is disconnected from the dilation device by sliding the retention element axially along the arms.

10. The system of claim 9, wherein the retention element comprises a central shaft, wherein the shaft comprises a plurality of laterally extending tabs, wherein a first side of each arm faces the center of the pattern, wherein each arm comprises a slot on the first side, wherein each tab engages a corresponding slot when the retention element is connected to the dilation device.

11. The system of claim 7, wherein a first side of each arm faces the center, wherein the retention element connects to a corresponding connection feature on the first side of each arm.

12. The system of claim 1, wherein the arms are configured to be disengaged from the arm clamps.

13. A system for opening a passageway in a mammalian body, wherein the system comprises:
a dilation device comprising a plurality of arms arranged in a pattern, wherein each arm is radially movable relative to a center of the pattern and laterally movable relative to adjacent arms in the pattern;
a stationary disk defining a plurality of slots;
a drive disk defining a plurality of slots, wherein the drive disk is configured to at least partially rotate about a longitudinal axis passing through the center of the pattern, wherein the arms are radially movable relative to the center of the pattern along the slots defined in the stationary disk and the drive disk;
a cannula insertable in the middle of the pattern of arms; and
a lock, wherein,
the lock automatically permits the cannula to move in the insertion direction;
the lock automatically prevents the cannula from moving in the removal direction; and
rotation of the drive disk resulting in radial movement of the arms away from the center of the pattern automatically permits the cannula to move in the removal direction;

wherein the dilation device transforms from a closed configuration to an open configuration, wherein the arms are in contacting longitudinal alignment and close to the center of the pattern in the closed configuration, wherein each arm is radially displaced from the center of the pattern and laterally displaced from adjacent arms in the open configuration.

14. The system of claim 13, wherein the cannula comprises a plurality of peripheral longitudinal holes configured to engage with the lock such that the engagement prevents the cannula from moving in the removal direction, wherein the rotation of the drive disk resulting in the radial movement of the arms away from the center of the pattern disengages the lock from the longitudinal holes, thereby permitting the cannula to move in the removal direction.

15. The system of claim 13, wherein at least a portion of the cannula is a conductor of light.

16. The system of claim 13, further comprising a retention element connectable to the dilation device, wherein the cannula is insertable in the middle of the pattern of arms after the retention element is disconnected from the dilation device.

17. A system for opening a passageway in a mammalian body, wherein the system comprises:
a dilation device comprising a plurality of arms arranged in a pattern, wherein the pattern of arms synchronously expands and contracts relative to a center of the pattern;
a stationary disk defining a plurality of slots;
a drive disk defining a plurality of slots, wherein the drive disk is configured to at least partially rotate about a longitudinal axis passing through the center of the pattern,
wherein the arms are radially movable relative to the center of the pattern along the slots defined in the stationary disk and the drive disk;
a retention element connectable to the dilation device, wherein,
the dilation device is held in a closed configuration when the retention element is connected to the dilation device, wherein the arms are in contacting longitudinal alignment and close to the center of the pattern in the closed configuration;
the dilation device is transformable from the closed configuration to an open configuration when the retention element is disconnected from the dilation device, wherein the arms are separated and far from the center of the pattern in the open configuration, wherein the retention element is disconnected from the dilation device by sliding the retention element axially along the arms, wherein the retention element comprises a body and a plurality of prongs extending from the body, wherein the prongs prevent rotation of the drive disk when the retention element is connected to the dilation device.

18. The system of claim 17, wherein the prongs are positioned outside the pattern of arms when the retention element is connected to the dilation device.

19. The system of claim 17, wherein the retention element comprises a central shaft, wherein the shaft comprises a plurality of laterally extending tabs, wherein a first side of each arm faces the center of the pattern, wherein each arm comprises a slot on the first side, wherein each tab engages a corresponding slot provided in the arms when the retention element is connected to the dilation device.

* * * * *